United States Patent
Hanaoka et al.

[11] Patent Number: 6,090,961
[45] Date of Patent: Jul. 18, 2000

[54] METHOD FOR PRODUCING TITANIUM COMPLEX

[75] Inventors: Hidenori Hanaoka, Osaka; Yoshiaki Oda, Toyonaka; Hiroshi Sohda, Takatsuki, all of Japan

[73] Assignee: Sumitomo Chemical Company, Limited, Osaka, Japan

[21] Appl. No.: 09/348,312

[22] Filed: Jul. 7, 1999

[30] Foreign Application Priority Data

Jul. 9, 1998 [JP] Japan .................... 10-194620
Sep. 10, 1998 [JP] Japan .................... 10-257006
Sep. 10, 1998 [JP] Japan .................... 10-257007

[51] Int. Cl.[7] ............... C07F 17/00; C07F 7/00
[52] U.S. Cl. ............... 556/11; 556/12; 556/52; 556/53; 526/160; 526/943; 502/103; 502/117
[58] Field of Search ............... 556/11, 12, 52, 556/53; 502/103, 117; 526/160, 943

[56] References Cited

U.S. PATENT DOCUMENTS 5,703,257 12/1997 Rosen et al. .................... 556/7

FOREIGN PATENT DOCUMENTS

08429390 A1 5/1998 European Pat. Off. .

*Primary Examiner*—Porfirio Nazario-Gonzalez

[57] ABSTRACT

There is disclosed a method for producing an alkoxytitanium complex of formula (I),

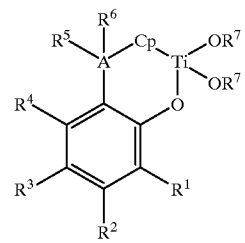

wherein Cp is a group having cyclopentadiene-type anion skeleton, A represents a carbon atom or silicon atom, $R^1$, $R^2$, $R^3$, $R^4$, $R^5$ and $R^6$ each independently represent a hydrogen atom, an alkyl group having 1 to 10 carbon atoms which optionally may be substituted and the like, and $R^7$ each independently represents an alkyl group having 1 to 10 carbon atoms which may be substituted and the like.

5 Claims, No Drawings

METHOD FOR PRODUCING TITANIUM COMPLEX

1. Field of the Invention

The present invention methods for producing an alkoxytitanium complex, aryloxytitanium complex and aminotitanium complex.

2. Description of the Related Art

Complexes of Group IV transition metals such as titanium, zirconium and the like are useful metal complexes used as Lewis acids in valuable reactions in organic synthesis such as transesterification reaction, Diels-Alder reaction.

Alkoxytitanium complexes, aryloxytitanium complexes and aminotitanium complexes are promising metal complexes (JP9-87313A), and development of production methods has been desired.

SUMMARY OF THE INVENTION

An object of the present invention is to provide industrially advantageous methods for producing an alkoxytitanium complex, aryloxytitanium complex and aminotitanium complex.

The present inventors have been intensively studied to accomplish the above-described object, and as a result, found industrially advantageous methods for producing an alkoxytitanium complex, aryloxytitanium complex and aminotitanium complex having catalytic activity as Lewis acids in valuable reactions in organic synthesis, completing the present invention.

The present invention provides:

1. A method for producing an alkoxytitanium complex represented by the general formula (I),

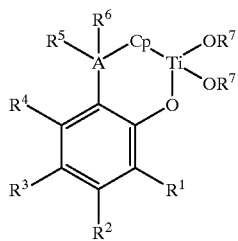

wherein Cp is a group having cyclopentadiene-type anion skeleton,

A represents a carbon atom or silicon atom, $R^1$, $R^2$, $R^3$ and $R^4$ each independently represent:
   a hydrogen atom;
   a halogen atom;
   an alkyl group having 1 to 10 carbon atoms which may be substituted by fluorine,
   an alkoxy group having 1 to 10 carbon atoms which may be substituted by fluorine;
   an aryl group having 6 to 20 carbon atoms which may be substituted by fluorine;
   an aryloxy group having 6 to 20 carbon atoms which may be substituted by fluorine;
   an aralkyl group having 7 to 20 carbon atoms which may be substituted by fluorine;
   an aralkyloxy group having 7 to 20 carbon atoms which may be substituted by fluorine;
   a hydrocarbon-substituted silyl group having 1 to 20 carbon atoms; or
   a hydrocarbon-substituted amino group having 1 to 20 carbon atoms, $R^5$ and $R^6$ each independently represent:
   a hydrogen atom;
   an alkyl group having 1 to 10 carbon atoms which optionally may be substituted by fluorine;
   an alkoxy group having 1 to 10 carbon atoms which may be substituted by fluorine;
   an aryl group having 6 to 20 carbon atoms which may be substituted by fluorine,
   an aryloxy group having 6 to 20 carbon atoms which may be substituted by fluorine,
   an aralkyl group having 7 to 20 carbon atoms which may be substituted by fluorine;
   an aralkyloxy group having 7 to 20 carbon atoms which may be substituted by fluorine;
   a hydrocarbon-substituted silyl group having 1 to 20 carbon atoms; or
   a hydrocarbon-substituted amino group having 1 to 20 carbon atoms; and $R^7$ is the same or different and each independently represent:
   an alkyl group having 1 to 10 carbon atoms which may be substituted; or
   an aralkyl group having 7 to 20 carbon atoms which may be substituted; or
   $R^7$ groups may bond each other to form a ring, which comprises reacting:
   a halogenated titanium complex represented by the general formula (II)

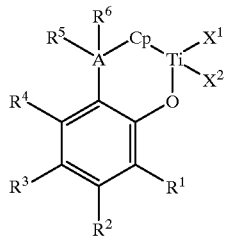

wherein, Cp, A, $R^1$, $R^2$, $R^3$, $R^4$, $R^5$ and $R^6$ are the same as defined above, and $X^1$ and $X^2$ each independently represent a halogen atom;

with an alkali metal alkoxide of the formula (III);

$R^7OM$ wherein $R^7$ is the same as defined above and M represents an alkali metal.

2. The method according to Item 1, which comprises: reacting a halogenated titanium complex of the formula (II) with an alcohol of the formula (III'):

$R^7OH$ wherein $R^7$ is the same as defined above.

3. The production method according as defined in item 2 above, wherein the reaction is conducted in the co-existence of an amine;

4. A method for producing an aryloxytitanium complex represented by the general formula (IV):

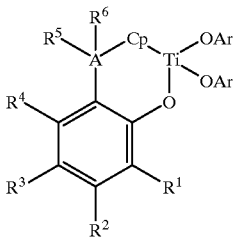

wherein Cp, A, $R^1$, $R^2$, $R^3$, $R^4$, $R^5$ and $R^6$ have respectively the same meanings as defined above; and Ar is the same or different and each represents an aryl group having 6 to 20 carbon atoms which may be substituted, or Ars may bond mutually to form a ring, which comprises reacting a halogenated titanium complex represented by the general formula (II) as defined in item 1 above with an alkali metal aryloxide represented by the general formula (V):

ArOM    (V)

wherein M represents an alkali metal atom, and Ar is the same as defined above; and 5. A method for producing an aminotitanium complex represented by the general formula (VI):

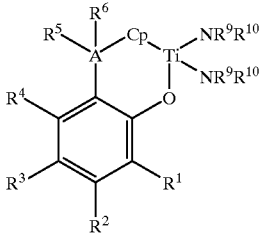

wherein Cp, A, $R^1$, $R^2$, $R^3$, $R^4$, $R^5$ and $R^6$ have respectively the same meanings as defined above, and $R^9$ and $R^{10}$ each independently represent an alkyl group having 1 to 10 carbon atoms which may be substituted, an aralkyl group having 7 to 20 carbon atoms which may be substituted or a silyl group having 1 to 20 carbon atoms which may be substituted, or $R^9$ and $R^{10}$ may bond each other to form a ring, which comprises reacting a halogenated titanium complex represented by the general formula (II) as define above with an alkali metal amide represented by the general formula (VII):

$R^9R^{10}NM$ wherein M represents an alkali metal atom, and $R^9$ and $R^{10}$ are the same as defined above.

DESCRIPTION OF THE PREFERRED EMBODIMENTS

The present invention will be described in detail below.

Examples of the group having cyclopentadiene-type anion skeleton represented as a substituent Cp in the alkoxytitanium complex (I), the aryloxytitanium complex (IV) and the aminotitanium complex (VI) include: an optionally substituted cyclopentadienyl group, an optionally substituted indenyl group and an optionally substituted fluorenyl group.

The optionally substituted cyclopentadienyl group may be substituted with at least one group selected from: a C1–C10 alkyl group, a phenyl group, a naphthyl group, a silyl group substituted with three groups selected from C1–C4 alkyl group and a phenyl group, and two adjacent C1–C10 alkyl groups may bond together at their terminals to form a tetramethylene group.

The optionally substituted indenyl group may be substituted with at lest one group selected from: a C1–C10 alkyl group, a phenyl group and a naphthyl group.

The optionally substituted fluorenyl group may be substituted with at lest one group group selected from: a C1–C12 alkyl group, a phenyl group and a naphthyl group.

Examples of the optionally substituted cyclopentadienyl groups include: a η5-cyclopentadienyl group, η5-methylcyclopentadienyl group, η5-dimethylcyclopentadienyl group, η5-trimethylcyclopentadienyl group, η5-tetramethylcyclopentadienyl group, η5-ethylcyclopentadienyl group, η5-n-propylcyclopentadienyl group, η5-isopropylcyclopentadienyl group, η5-n-butylcyclopentadienyl group, η5-sec-butylcyclopentadienyl group, η5-tert-butylcyclopentadienyl group, η5-n-pentylcyclopentadienyl group, η5-neopentylcyclopentadienyl group, η5-n-hexylcyclopentadienyl group, η5-n-octylcyclopentadienyl group, η5-tetrahydroindenyl group, η5-octahydrofluorenyl group, η5-phenylcyclopentadienyl group, η5-naphthylcyclopentadienyl group, η5-trimethylsilylcyclopentadienyl group, η5-triethylsilylcyclopentadienyl group, η5-triphenylsilylcyclopentadienyl group, η5-tert-butyldimethylsilylcyclopentadienyl group and the like;

Examples of the optionally substituted indenyl groups include: a η5-indenyl group, η5-methylindenyl group, η5-dimethylindenyl group, η5-ethylindenyl group, η5-n-propylindenyl group, η5-isopropylindenyl group, η5-n-butylindenyl group, η5-sec-butylindenyl group, η5-tert-butylindenyl group, η5-n-pentylindenyl group, η5-neopentylindenyl group, η5-n-hexylindenyl group, η5-n-octylindenyl group, η5-n-decylindenyl group, η5-phenylindenyl group, η5-methylphenylindenyl group, η5-naphthylindenyl group and the like, Examples of the optionally substituted fluorenyl group include: a η5-fluorenyl group, η5-methylfluorenyl group, η5-dimethylfluorenyl group, η5-ethylfluorenyl group, η5-diethylfluorenyl group, η5-n-propylfluorenyl group, η5-di-n-propylfluorenyl group, η5-isopropylfluorenyl group, η5-diisopropylfluorenyl group, η5-n-butylfluorenyl group, η5-sec-butylfluorenyl group, η5-tert-butylfluorenyl group, η5-di-n-butylfluorenyl group, η5-di-sec-butylfluorenyl group, η5-di-tert-butylfluorenyl group, η5-n-pentylfluorenyl group, η5-neopentylfluorenyl group, η5-n-hexylfluorenyl group, η5-n-octylfluorenyl group, η5-n-decylfluorenyl group, η5-n-dodecylfluorenyl group, η5-phenylfluorenyl group, η5-di-phenylfluorenyl group, η5-methylphenylfluorenyl group, η5-naphthylfluorenyl group and the like, and preferably examples thereof include a η5-cyclopentadienyl group, η5-methylcyclopentadienyl group, η5-tert-butylcyclopentadienyl group, η5-tetramethylcyclopentadienyl group, η5-indenyl group, η5-fluorenyl group and the like.

Examples of the halogen in the substituents $R^1$, $R^2$, $R^3$ and $R^4$ include fluorine, chlorine, bromine and iodine atoms and the like.

Examples of the alkyl group having 1 to 10 carbon atoms which may be substituted by fluorine in the substituents $R^1$, $R^2$, $R^3$, $R^4$, $R^5$ and $R^6$ include a methyl group, ethyl group, n-propyl group, isopropyl group, n-butyl group, sec-butyl group, tert-butyl group, n-pentyl group, neopentyl group, amyl group, n-hexyl group, n-octyl group, n-decyl group, fluoromethyl group, difluoromethyl group, trifluoromethyl group, fluoroethyl group, difluoroethyl group, trifluoroethyl group, tetrafluoroethyl group, pentafluoroethyl group, perfluoropropyl group, perfluorobutyl group, perfluoropentyl group, perfluorohexyl group, perfluorooctyl group, perfluorodecyl group and the like, and preferable examples thereof include a methyl group, ethyl group, isopropyl group, tert-butyl group and amyl group.

Examples of the alkoxy group having 1 to 10 carbon atoms which may be substituted by fluorine in the substituents $R^1$, $R^2$, $R^3$, $R^4$, $R^5$ and $R^6$ include a methoxy group, ethoxy group, n-propoxy group, isopropoxy group, n-butoxy group, sec-butoxy group, tert-butoxy group, n-pentoxy group, neopentoxy group, n-hexoxy group, n-octoxy group, n-dexoxy group, and fluorine atom-substituted alkoxy groups thereof, and preferable examples thereof include a methoxy group, ethoxy group and tert-butoxy group.

Examples of the aryl group having 6 to 20 carbon atoms which may be substituted by fluorine in the substituents $R^1$, $R^2$, $R^3$, $R^4$, $R^5$ and $R^6$ include a phenyl group, 2-tolyl group, 3-tolyl group, 4-tolyl group, 2,3-xylyl group, 2,4-xylyl group, 2,5-xylyl group, 2,6-xylyl group, 3,4-xylyl group, 3,5-xylyl group, 2,3,4-trimethylphenyl group, 2,3,5-trimethylphenyl group, 2,3,6-trimethylphenyl group, 2,4,6-trimethylphenyl group, 3,4,5-trimethylphenyl group, 2,3,4,5-tetramethylphenyl group, 2,3,4,6-tetramethylphenyl group, 2,3,5,6-tetramethylphenyl group, pentamethylphenyl group, ethylphenyl group, n-propylphenyl group, isopropylphenyl group, n-butylphenyl group, sec-butylphenyl group, tert-butylphenyl group, n-pentylphenyl group, neopentylphenyl group, n-hexylphenyl group, n-octylphenyl group, n-decylphenyl group, n-dodecylphenyl group, n-tetradecylphenyl group, naphthyl group, anthracenyl group and fluorine atom- substituted aryl groups thereof. Among them, a phenyl group is preferred.

Examples of the aryloxy group having 6 to 20 carbon atoms which may be substituted by fluorine in the substituents $R^1$, $R^2$, $R^3$, $R^4$, $R^5$ and $R^6$ include a phenoxy group, 2-methylphenoxy group, 3-methylphenoxy group, 4-methylphenoxy group, 2,3-dimethylphenoxy group, 2,4-dimethylphenoxy group, 2,5-dimethylphenoxy group, 2,6-dimethylphenoxy group, 3,4-dimethylphenoxy group, 3,5-dimethylphenoxy group, 2,3,4-trimethylphenoxy group, 2,3,5-trimethylphenoxy group, 2,3,6-trimethylphenoxy group, 2,4,5-trimethylphenoxy group, 2,4,6-trimethylphenoxy group, 3,4,5-trimethylphenoxy group, 2,3,4,5-tetramethylphenoxy group, 2,3,4,6-tetramethylphenoxy group, 2,3,5,6-tetramethylphenoxy group, pentamethylphenoxy group, ethylphenoxy group, n-propylphenoxy group, isopropylphenoxy group, n-butylphenoxy group, sec-butylphenoxy group, tert-butylphenoxy group, n-hexylphenoxy group, n-octylphenoxy group, n-decylphenoxy group, n-tetradecylphenoxy group, naphtoxy group, anthracenoxy group and fluorine-substituted aryloxy groups thereof.

Examples of the aralkyl group having 7 to 20 carbon atoms which may be substituted by fluorine in the substituents $R^1$, $R^2$, $R^3$, $R^4$, $R^5$ and $R^6$ include a benzyl group, (2-methylphenyl)methyl group, (3-methylphenyl)methyl group, (4-methylphenyl)methyl group, (2,3-dimethylphenyl)methyl group, (2,4-dimethylphenyl)methyl group, (2,5-dimethylphenyl)methyl group, (2,6-dimethylphenyl)methyl group, (3,4-dimethylphenyl)methyl group, (2,3,4-trimethylphenyl)methyl group, (2,3,5-trimethylphenyl)methyl group, (2,3,6-trimethylphenyl)methyl group, (3,4,5-trimethylphenyl)methyl group, (2,4,6-trimethylphenyl)methyl group, (2,3,4,5-tetramethylphenyl)methyl group, (2,3,4,6-tetramethylphenyl)methyl group, (2,3,5,6-tetramethylphenyl)methyl group, (pentamethylphenyl)methyl group, (ethylphenyl)methyl group, (n-propylphenyl)methyl group, (isopropylphenyl)methyl group, (n-butylphenyl)methyl group, (sec-butylphenyl)methyl group, (tert-butylphenyl)methyl group, (n-pentylphenyl)methyl group, (neopentylphenyl)methyl group, (n-hexylphenyl)methyl group, (n-octylphenyl)methyl group, (n-decylphenyl)methylgroup, (n-dodecylphenyl)methylgroup, (n-tetradecylphenyl)methyl group, naphthylmethyl group, anthracenylmethyl group and fluorine atom-substituted aralkyl groups thereof, and a benzyl group is preferable.

Examples of the aralkyloxy group having 7 to 20 carbon atoms which may be substituted by fluorine in the substituents $R^1$, $R^2$, $R^3$, $R^4$, $R^5$ and $R^6$ include a benzyloxy group, (2-methylphenyl)methoxy group, (3-methylphenyl)methoxy group, (4-methylphenyl)methoxy group, (2,3-dimethylphenyl)methoxy group, (2,4-dimethylphenyl)methoxy group, (2,5-dimethylphenyl)methoxy group, (2,6-dimethylphenyl)methoxy group, (3,4-dimethylphenyl)methoxy group, (2,3,4-trimethylphenyl)methoxy group, (2,3,5-trimethylphenyl)methoxy group, (2,3,6-trimethylphenyl) meth oxy group, (3,4,5-trimethylphenyl)methoxy group, (2,4,6-trimethylphenyl)methoxy group, (2,3,4,5-tetramethylphenyl)methoxy group, (2,3,4,6-tetramethylphenyl)methoxy group, (2,3,5,6-tetramethylphenyl)methoxy group, (pentamethylphenyl)methoxy group, (ethylphenyl)methoxy group, (n-propylphenyl)methoxy group, (isopropylphenyl)methoxy group, (n-butylphenyl)methoxy group, (sec-butylphenyl)methoxy group, (tert-butylphenyl)methoxy group, (n-pentylphenyl)methoxy group, (neopentylphenyl)methoxy group, (n-hexylphenyl)methoxy group, (n-octylphenyl)methoxy group, (n-decylphenyl)methoxy group, (n-dodecylphenyl)methoxy group, (n-tetradecylphenyl)methoxy group, naphthylmethoxy group, anthracenylmethoxy group and fluorine atom-substituted aralkyloxy groups thereof, and a benzyloxy group is preferable.

The hydrocarbon-substituted silyl group having 1 to 20 carbon atoms in the substituents $R^1$, $R^2$, $R^3$, $R^4$, $R^5$ and $R^6$ is a silyl group substituted by a hydrocarbon having 1 to 20 carbon atoms, and examples of the hydrocarbon group include alkyl groups having 1 to 10 carbon atoms such as a methyl group, ethyl group, n-propyl group, isopropyl group, n-butyl group, sec-butyl group, tert-butyl group, n-pentyl group, neopentyl group, amyl group, n-hexyl group, cyclohexyl group, n-octyl group, n-decyl group and the like, aryl groups having 1 to 20 carbon atoms such as a phenyl group, tolyl group, xylyl group, naphthyl group, anthracenyl group, and the like.

Examples of such a hydrocarbon-substituted silyl group having 1 to 20 carbon atoms include mono-substituted silyl groups such as a methylsilyl group, ethylsilyl group, phenylsilyl group and the like, di-substituted silyl groups such as a dimethylsilyl group, diethylsilyl group, diphenylsilyl group and the like, tri-substituted silyl groups such as a trimethylsilyl group, triethylsilyl group, tri-n-propylsilyl group, tri-isopropylsilyl group, tri-n-butylsilyl group, tri-sec-butylsilyl group, tri-tert-butylsilyl group, tri-isobutylsilyl group, tert-butyldimethylsilyl group, tri-n-pentylsilyl group, tri-n-hexylsilyl group, tricyclohexylsilyl group, triphenylsilyl group, and the like, and preferable examples thereof include a trimethylsilyl group, tert-butyldimethylsilyl group, and triphenylsilyl group. Any of these substituted silyl groups may have substitution by a fluorine atom on a hydrocarbon group thereof.

The hydrocarbon-substituted amino group having 1 to 20 carbon atoms in the substituents $R^1$, $R^2$, $R^3$, $R^4$, $R^5$ and $R^6$ is an amino group substituted by two hydrocarbon groups, and examples of the hydrocarbon group include alkyl groups having 1 to 10 carbon atoms such as a methyl group, ethyl group, n-propyl group, isopropyl group, n-butyl group, sec-butyl group, tert-butyl group, n-pentyl group, neopentyl group, amyl group, n-hexyl group, cyclohexyl group, n-octyl group, n-decyl group and the like, aryl groups having 1 to 20 carbon atoms such as a phenyl group, tolyl group, xylyl group, naphthyl group, anthracenyl group, and the like. Examples of such a hydrocarbon-substituted amino group having 1 to 20 carbon atoms include a dimethylamino group, diethylamino group, di-n-propylamino group, diisopropylamino group, di-n-butyl amino group, di-sec-butylamino group, di-tert-butylamino group, di-isobutylamino group, tert-butylisopropylamino group, di-n-hexylamino group, di-n-octylaminogroup, di-n-decylamino group, diphenylamino group and the like, and a dimethylamino group and a diethylamino group are preferably listed.

Examples of the alkyl group having 1 to 10 carbon atoms which may be substituted in the substituents $R^7$ include alkyl groups such as a methyl group, ethyl group, n-propyl group, isopropyl group, n-butyl group, sec-butyl group, tert-butyl group, n-pentyl group, neopentyl group, amyl group, n-hexyl group, n-octyl group, n-decyl group and the like, halogenated alkyl groups such as a chloromethyl group, dichloromethyl group, trichloromethyl group, bromomethyl group, dibromomethyl group, tribromomethyl group, fluoromethyl group, difluoromethyl group, trifluoromethyl group, fluoroethyl group, difluoroethyl group, trifluoroethyl group, tetrafluoroethyl group, pentafluoroethyl group, perfluoropropyl group, hexafluoroisopropyl group, perfluorobutyl group, perfluoropentyl group, perfluorohexyl group, perfluorooctyl group, perfluorodecyl group and the like, and alkoxyalkyl groups such as a methoxymethyl group, ethoxymethyl group, n-propoxymethyl group, isopropoxymethyl group, phenoxymethyl group, methoxyethyl group, ethoxyethyl group, n-propoxyethyl group, isopropoxyethyl group, phenoxyethyl group and the like, and preferably examples thereof include a methyl group, ethyl group, isopropyl group, hexafluoroisopropyl group and methoxyethyl group.

Examples of the aralkyl group having 7 to 20 carbon atoms whichmaybe substituted in the substituent $R^7$ include a benzyl group, (2-methylphenyl)methyl group, (3-methylphenyl)methyl group, (4-methylphenyl)methyl group, (2,3-dimethylphenyl)methyl group, (2,4-dimethylphenyl)methyl group, (2,5-dimethylphenyl)methyl group, (2,6-dimethylphenyl)methyl group, (3,4-dimethylphenyl)methyl group, (2,3,4-trimethylphenyl)methyl group, (2,3,5-trimethylphenyl)methyl group, (2,3,6-trimethylphenyl)methyl group, (3,4,5-trimethylphenyl)methyl group, (2,4,6-trimethylphenyl)methyl group, (2,3,4,5-tetramethylphenyl)methyl group, (2,3,4,6-tetramethylphenyl)methyl group, (2,3,5,6-tetramethylphenyl)methyl group, (pentamethylphenyl)methyl group, (ethylphenyl)methyl group, (n-propylphenyl)methyl group, (isopropylphenyl)methyl group, (n-butylphenyl)methyl group, (sec-butylphenyl)methyl group, (tert-butylphenyl)methyl group, (n-pentylphenyl)methyl group, (neopentylphenyl)methyl group, (n-hexylphenyl)methyl group, (n-octylphenyl)methyl group, (n-decylphenyl)methylgroup, (n-dodecylphenyl)methylgroup, (n-tetradecylphenyl)methyl group, naphthylmethyl group, anthracenylmethyl group, 1-phenylethyl group, 1-(1-naphthyl)ethyl group, 1-(2-naphthyl)ethyl group; haloaralkyl groups obtained by substitution by halogen such as a fluorine atom, chlorine atom, iodine atom or the like on the above-described groups; alkoxyaralkyl groups obtained by optional substitution by a methoxy group, ethoxy group, n-propoxy group, isopropoxy group, n-butoxy group, sec-butoxy group, tert-butoxy group and the like of a halogen atom on the above-described haloaralkyl groups; and a cyanoaralkyl group, nitroaralkyl group and the like. Among them, a benzyl group is preferred.

Two $R^7$ groups may bond mutually to form a ring, and examples thereof include 1,2-dioxy groups such as an ethylenedioxy group, methylethylenedioxy group, 1,1-dimethylethylenedioxy group, 1,2-dimethylethylenedioxy group, 1,1,2-trimethylethylenedioxy group, tetramethylethylenedioxy group, phenylethylenedioxy group, 1,1-diphenylethylenedioxy group, 1,2-diphenylethylenedioxy group, 1,1,2-triphenylethylenedioxy group, tetraphenylethylenedioxy group, cyclobutane-1,2-dioxy group, cyclopentane-1,2-dioxy group, cyclohexane-1,2-dioxy group, cycloheptane-1,2-dioxy group, cyclooctane-1,2-dioxy group and the like, 1,3-dioxy groups such as a propylene-1,3-dioxy group, 1-methylpropylene-1,3-dioxy group, 2-methylpropylene-1,3-dioxy group, 1,1-dimethylpropylene-1,3-dioxy group, 1,2-dimethylpropylene-1,3-dioxy group, 1,3-dimethylpropylene-1,3-dioxy group, 2,2-dimethylpropylene-1,3-dioxy group, 1,1,2-trimethylpropylenedioxy group, 1,1,3-trimethylpropylenedioxy group, 1,2,2-trimethylpropylenedioxy group, 1,2,3-trimethylpropylenedioxy group, 1,1,2,2-tetramethylpropylenedioxy group, 1,1,2,3-tetrapethylpropylenedioxy group, 1,2,2,3-tetramethylpropylenedioxy group, 1,1,2,3-tetramethylpropylenedioxy group, 1,1,2,2,3-tetramethylpropylenedioxy group, 1,1,2,3,3-pentamethylpropylenedioxy group, 1,1,2,2,3,3-hexamethylpropylenedioxy group, 1-phenylpropylene-1,3-dioxy group, 2-phenylpropylene-1,3-dioxy group, 1,1-diphenylpropylene-1,3-dioxy group, 1,2-diphenylpropylene-1,3-dioxy group, 1,3-diphenylpropylene-1,3-dioxy group, 2,2-diphenylpropylene-1,3-dioxy group, 1,1,2-triphenylpropylenedioxy group, 1,1,3-triphenylpropylenedioxy group, 1,2,2-triphenylpropylenedioxy group, 1,2,3-triphenylpropylenedioxy group, 1,1,2,2-tetraphenylpropylenedioxy group, 1,1,2,3-tetraphenylpropylenedioxy group, 1,1,3,3-tetraphenylpropylenedioxy group, 1,2,2,3-tetraphenylpropylenedioxy group, 1,1,2,2,3-tetraphenylpropylenedioxy group, 1,1,2,3,3-pentaphenylpropylenedioxy group, 1,1,2,2,3,3-pentaphenylpropylenedioxy group, 1,1,2,2,3,3-hexaphenylpropylenedioxy group and the like, and also stereo and optical isomers thereof.

Examples of the aryl group having 6 to 20 carbon atoms which may be substituted, represented by Ar, in the alkali metal aryloxides (V) and the aryloxytitanium complex (IV) include a phenyl group, 2-methylphenyl group, 3-methylphenyl group, 4-methylphenyl group, 2,3-dimethylphenyl group, 2,4-dimethylphenyl group, 2,5-dimethylphenyl group, 2,6-dimethylphenyl group, 3,4-dimethylphenyl group, 2,3,4-trimethylphenyl group, 2,3,5-trimethylphenyl group, 2,3,6-trimethylphenyl group, 3,4,5-trimethylphenyl group, 2,4,6-trimethylphenyl group, 2,3,4,5-tetramethylphenyl group, 2,3,4,6-tetramethylphenyl group, 2,3,5,6-tetramethylphenyl group, pentamethylphenyl group, ethylphenyl group, n-propylphenyl group, isopropylphenyl group, n-butylphenyl group, sec-butylphenyl group, tert-butylphenyl group, n-pentylphenyl group, neopentylphenyl group, n-hexylphenyl group, n-octylphenyl group, n-decylphenyl group, n-dodecylphenyl group, n-tetradecylphenyl group, naphthyl group, anthracenyl group; haloaryl groups obtained by substitution by halogen such as a fluorine atom, chlorine atom, iodine atom or the like on the above-described groups; alkoxyaryl groups obtained by optional substitution by a methoxy group, ethoxy group, n-propoxy group, isopropoxy group, n-butoxy group, sec-butoxy group, tert-butoxy group and the like of a halogen atom on the above-described haloaralkyl groups; and a cyanoaryl group, nitroaryl group and the like, and preferable examples thereof include a phenyl group, 4-methylphenyl group and 2,4,6-trimethylphenyl group.

The substituents Ars may bond each other to form a ring, and examples thereof include biaryl groups and cross-linked biaryl groups such as a 1,1'-biphenyl-2,2'-diyl group, 1,1'-biphenyl-4,4'-dimethyl-2,2'-diyl group, 1,1'-biphenyl-6,6'-dimethyl-2,2'-diyl group, 1,1'-biphenyl-3,3'-di-tert-butyl-2,2'-diyl group, 1,1'-binaphthyl-2,2'-diyl group, 1,1'-binaphthyl-3,3'-bis(trimethylsilyl)-2,2'-diyl group, 1,1'-thiobiphenyl-2,2'-diyl group, 1,1'-thiobiphenyl-5,5'-dimethyl-2,2'-diyl group, 1,1'-thiobiphenyl-3,3'-di-tert-butyl-5,5'-dimethyl-2,2'-diyl group, 1,1'-methylenebiphenyl-2,2'-diyl group, 1,1'-methylenebiphenyl-5,5'-dimethyl-2,2'-diyl group, 1,1'-methylenebiphenyl-3,3'-di-tert-butyl-5,5'-dimethyl-2,2'-diyl group, 1,1'-phenylphosphinobiphenyl-2,2'-diyl group, 1,1'-phenylphosphinobiphenyl-5,5'-dimethyl-2,2'-diyl group, 1,1'-phenylphosphinobiphenyl-3,3'-di-tert-butyl-5,5'-dimethyl-2,2'-diyl group and the like, and preferable are 1,1'-biphenyl-2,2'-diyl group and 1,1'-binaphthyl-2,2'-diyl group.

Examples of the alkyl group having 1 to 10 carbon atoms which may be substituted in the substituents $R^9$ and $R^{10}$ in the alkali metal amides (VII) and the aminotitanium complex (VI) include alkyl groups such as a methyl group, ethyl group, n-propyl group, isopropyl group, n-butyl group, sec-butyl group, tert-butyl group, n-pentyl group, neopentyl group, amyl group, n-hexyl group, n-octyl group, n-decyl group and the like, halogenated alkyl groups such as a chloromethyl group, dichloromethyl group, trichloromethyl group, bromomethyl group, dibromomethyl group, tribromomethyl group, fluoromethyl group, difluoromethyl group, trifluoromethyl group, fluoroethyl group, difluoroethyl group, trifluoroethyl group, tetrafluoroethyl group, pentafluoroethyl group, perfluoropropyl group, hexafluoroisopropyl group, perfluorobutyl group, perfluoropentyl group, perfluorohexyl group, perfluorooctyl group, perfluorodecyl group and the like, and alkoxyalkyl groups such as a methoxymethyl group, ethoxymethyl group, n-propoxymethyl group, isopropoxymethyl group, phenoxymethyl group, methoxyethyl group, ethoxyethyl group, n-propoxyethyl group, isopropoxyethyl group, phenoxyethyl group and the like, and preferably examples thereof include a methyl group, ethyl group, isopropyl group, and methoxyethyl group.

Examples of the aralkyl group having 7 to 20 carbon atoms which may be substituted in the substituents $R^7$ include a benzyl group, (2-methylphenyl)methyl group, (3-methylphenyl)methyl group, (4-methylphenyl)methyl group, (2,3-dimethylphenyl)methyl group, (2,4-dimethylphenyl)methyl group, (2,5-dimethylphenyl)methyl group, (2,6-dimethylphenyl)methyl group, (3,4-dimethylphenyl)methyl group, (2,3,4-trimethylphenyl)methyl group, (2,3,5-trimethylphenyl)methyl group, (2,3,6-trimethylphenyl)methyl group, (3,4,5-trimethylphenyl)methyl group, (2,4,6-trimethylphenyl)methyl group, (2,3,4,5-tetramethylphenyl)methyl group, (2,3,4,6-tetramethylphenyl)methyl group, (2,3,5,6-tetramethylphenyl)methyl group, (pentamethylphenyl)methyl group, (ethylphenyl)methyl group, (n-propylphenyl)methyl group, (isopropylphenyl)methyl group, (n-butylphenyl)methyl group, (sec-butylphenyl)methyl group, (tert-butylphenyl)methyl group, (n-pentylphenyl)methyl group, (neopentylphenyl)methyl group, (n-hexylphenyl)methyl group, (n-octylphenyl)methyl group, (n-decylphenyl)methyl group, (n-dodecylphenyl)methyl group, (n-tetradecylphenyl)methyl group, naphthylmethyl group, anthracenylmethyl group, 1-phenylethyl group, 1-(1-naphthyl)ethyl group, 1-(2-naphthyl)ethyl group; haloalkyl groups obtained by substitution by halogen such as a fluorine atom, chlorine atom, iodine atom or the like on the above-described groups; alkoxyaralkyl groups obtained by optional substitution by a methoxy group, ethoxy group, n-propoxy group, isopropoxy group, n-butoxy group, sec-butoxy group, tert-butoxy group and the like of a halogen atom on the above-described haloaralkyl groups; and a cyanoaralkyl group, nitroaralkyl group and the like. Among them, a benzyl group is preferred.

The hydrocarbon-substituted silyl group having 1 to 20 carbon atoms which may be substituted in the substituents $R^9$ and $R^{10}$ is a silyl group substituted by a hydrocarbon group having 1 to 20 carbon atoms, and examples of the hydrocarbon group include alkyl groups having 1 to 10 carbon atoms such as a methyl group, ethyl group, n-propyl group, isopropyl group, n-butyl group, sec-butyl group, tert-butyl group, n-pentyl group, neopentyl group, amyl group, n-hexyl group, cyclohexyl group, n-octyl group, n-decyl group and the like, aryl groups having 1 to 20 carbon atoms such as a phenyl group, tolyl group, xylyl group, naphthyl group, anthracenyl group, and the like. Examples of such a hydrocarbon-substituted silyl group having 1 to 20 carbon atoms include mono-substituted silyl groups such as a methylsilyl group, ethylsilyl group, phenylsilyl group and the like, di-substituted silyl groups such as a dimethylsilyl group, diethylsilyl group, diphenylsilyl group and the like, tri-substituted silyl groups such as a trimethylsilyl group, triethylsilyl group, tri-n-propylsilyl group, tri-isopropylsilyl group, tri-n-butylsilyl group, tri-sec-butylsilyl group, tri-tert-butylsilyl group, tri-isobutylsilyl group, tert-butyldimethylsilyl group, tri-n-pentylsilyl group, tri-n-hexylsilyl group, tricyclohexylsilyl group, triphenylsilyl group, and the like, and preferable examples thereof include a trimethylsilyl group, tert-butyldimethylsilyl group, and triphenylsilyl group.

Examples of the alkoxytitanium complex (I) in which A represents a carbon atom obtained according to the present invention include (η5-cyclopentadienyl)(2-phenoxy)methanetitanium dimethoxide, (η5-cyclopentadienyl)(3,4-dimethyl-2-phenoxy)methanetitanium dimethoxide, (η5-cyclopentadienyl)(3-tert-butyl-5-methyl-2-phenoxy)

methanetitanium dimethoxide, (η5-cyclopentadienyl)(3-tert-butyl-5-methoxy-2-phenoxy)methanetitanium dimethoxide, (η5-cyclopentadienyl)(3-tert-butyl-2-phenoxy)methanetitanium dimethoxide, (η5-cyclopentadienyl)(3-tert-butyl-5-chloro-2-phenoxy) methanetitanium dimethoxide, (η5-cyclopentadienyl)(3-phenyl-2-phenoxy)methanetitanium dimethoxide, (η5-cyclopentadienyl)(3-tert-butyldimethylsilyl-5-methyl-2-phenoxy)methanetitanium dimethoxide, (η5-cyclopentadienyl)(3-trimethylsilyl-5-methyl-2-phenoxy) methanetitanium dimethoxide, (η5-cyclopentadienyl)(2-phenoxy) dimethylmethanetitanium dimethoxide, (η5-cyclopentadienyl)(3,4-dimethyl-2-phenoxy) dimethylmethanetitanium dimethoxide, (η5-cyclopentadienyl)(3-tert-butyl-5-methyl-2-phenoxy) dimethylmethanetitanium dimethoxide, (η5-cyclopentadienyl)(3-tert-butyl-5-methoxy-2-phenoxy) dimethylmethanetitanium dimethoxide, (η5-cyclopentadienyl)(3-tert-butyl-2-phenoxy) dimethylmethanetitanium dimethoxide, (η5-cyclopentadienyl)(3-tert-butyl-5-chloro-2-phenoxy) dimethylmethanetitanium dimethoxide, (η5-cyclopentadienyl)(3-phenyl-2-phenoxy) dimethylmethanetitanium dimethoxide, (η5-cyclopentadienyl)(3-tert-butyldimethylsilyl-5-methyl-2-phenoxy)dimethylmethanetitanium dimethoxide, (η5-cyclopentadienyl)(3-trimethylsilyl-5-methyl-2-phenoxy)dimethylmethanetitanium dimethoxide, (η5-cyclopentadienyl)(2-phenoxy) diphenylmethanetitanium dimethoxide, (η5-cyclopentadienyl)(3,4-dimethyl-2-phenoxy) diphenylmethanetitanium dimethoxide, (η5-cyclopentadienyl)(3-tert-butyl-5-methyl-2-phenoxy) diphenylmethanetitanium dimethoxide, (η5-cyclopentadienyl)(3-tert-butyl-5-methoxy-2-phenoxy) diphenylmethanetitanium dimethoxide, (η5-cyclopentadienyl)(3-tert-butyl-2-phenoxy) diphenylmethanetitanium dimethoxide, (η5-cyclopentadienyl)(3-tert-butyl-5-chloro-2-phenoxy) diphenylmethanetitanium dimethoxide, (η5-cyclopentadienyl)(3-phenyl-2-phenoxy) diphenylmethanetitanium dimethoxide, (η5-cyclopentadienyl)(3-tert-butyldimethylsilyl-5-methyl-2-phenoxy)diphenylmethanetitanium dimethoxide, (η5-cyclopentadienyl)(3-trimethylsilyl-5-methyl-2-phenoxy)diphenylmethanetitanium dimethoxide, (η5-2,3,4,5-tetramethylcyclopentadienyl)(2-phenoxy) methanetitanium dimethoxide, (η5-2,3,4,5-tetramethylcyclopentadienyl)(3,4-dimethyl-2-phenoxy)methanetitanium dimethoxide, (η5-2,3,4,5-tetramethylcyclopentadienyl)(3-tert-butyl-5-methyl-2-phenoxy)methanetitanium dimethoxide, (η5-2,3,4,5-tetramethylcyclopentadienyl)(3-tert-butyl-5-methoxy-2-phenoxy)methanetitanium dimethoxide, (η5- 2,3,4,5-tetramethylcyclopentadienyl)(3-tert-butyl-2-phenoxy)methanetitanium dimethoxide, (η5-2,3,4,5-tetramethylcyclopentadienyl)(3-tert-butyl-5-chloro-2-phenoxy)methanetitanium dimethoxide, (η5-2,3,4,5-tetramethylcyclopentadienyl)(3-phenyl-2-phenoxy) methanetitanium dimethoxide, (η5-2,3,4,5-tetramethylcyclopentadienyl)(3-tert-butyldimethylsilyl-5-methyl-2-phenoxy) methanetitanium dimethoxide, (η5-2,3,4,5-tetramethylcyclopentadienyl)(3-trimethylsilyl-5-methyl-2-phenoxy)methanetitanium dimethoxide, (η5-2,3,4,5-tetramethylcyclopentadienyl)(2-phenoxy) dimethylmethanetitanium dimethoxide, (η5-2,3,4,5-tetramethylcyclopentadienyl)(3,4-dimethyl-2-phenoxy)dimethylmethanetitanium dimethoxide, (η5-2,3,4,5-tetramethylcyclopentadienyl)(3-tert-butyl-5-methyl-2-phenoxy) dimethylmethanetitanium dimethoxide, (η5-2,3,4,5-tetramethylcyclopentadienyl)(3-tert-butyl-5-methoxy-2-phenoxy) dimethylmethanetitanium dimethoxide, (η5-2,3,4,5-tetramethylcyclopentadienyl)(3-tert-butyl-2-phenoxy) dimethylmethanetitanium dimethoxide, (η5-2,3,4,5-tetramethylcyclopentadienyl)(3-tert-butyl-5-chloro-2-phenoxy)dimethylmethanetitanium dimethoxide, (η5-2,3,4,5-tetramethylcyclopentadienyl)(3-phenyl-2-phenoxy)dimethylmethanetitanium dimethoxide, (η5-2,3,4,5-tetramethylcyclopentadienyl)(3-tert-butyldimethylsilyl-5-methyl-2-phenoxy) dimethylmethanetitanium dimethoxide, (η5-2,3,4,5-tetramethylcyclopentadienyl)(3-trimethylsilyl-5-methyl-2-phenoxy)dimethylmethanetitanium dimethoxide, (η5-2,3,4,5-tetramethylcyclopentadienyl)(2-phenoxy) diphenylmethanetitanium dimethoxide, (η5-2,3,4,5-tetramethylcyclopentadienyl)(3,4-dimethyl-2-phenoxy)diphenylmethanetitanium dimethoxide, (η5-2,3,4,5-tetramethylcyclopentadienyl)(3-tert-butyl-5-methyl-2-phenoxy)diphenylmethanetitanium dimethoxide, (η5-2,3,4,5-tetramethylcyclopentadienyl)(3-tert-butyl-5-methoxy-2-phenoxy)diphenylmethanetitanium dimethoxide, (η5-2,3,4,5-tetramethylcyclopentadienyl)(3-tert-butyl-2-phenoxy)diphenylmethanetitanium dimethoxide, (η5-2,3,4,5-tetramethylcyclopentadienyl)(3-tert-butyl-5-chloro-2-phenoxy)diphenylmethanetitanium dimethoxide, (η5-2,3,4,5-tetramethylcyclopentadienyl)(3-phenyl-2-phenoxy) diphenylmethanetitanium dimethoxide, (η5-2,3,4,5-tetramethylcyclopentadienyl)(3-tert-butyldimethylsilyl-5-methyl-2-phenoxy) diphenylmethanetitanium dimethoxide, (η5-2,3,4,5-tetramethylcyclopentadienyl)(3-trimethylsilyl-5-methyl-2-phenoxy)diphenylmethanetitanium dimethoxide, (η5-3-methyllcyclopentadienyl)(2-phenoxy) methanetitanium dimethoxide, (η5-3-methylcyclopentadienyl)(3,4-dimethyl-2-phenoxy) methanetitanium dimethoxide, (η5-3-methylcyclopentadienyl)(3-tert-butyl-5-methyl-2-phenoxy)methanetitanium dimethoxide, (η5-3-methylcyclopentadienyl)(3-tert-butyl-5-methoxy-2-phenoxy)methanetitanium dimethoxide, (η5-3-methylcyclopentadienyl)(3-tert-butyl-2-phenoxy) methanetitanium dimethoxide, (η5-3-methylcyclopentadienyl)(3-tert-butyl-5-chloro-2-phenoxy)methanetitanium dimethoxide, (η5-3-methylcyclopentadienyl)(3-phenyl-2-phenoxy) methanetitanium dimethoxide, (η5-3-methylcyclopentadienyl)(3-tert-butyldimethylsilyl-5-methyl-2-phenoxy)methanetitanium dimethoxide, (η5-3-methylcyclopentadienyl)(3-trimethylsilyl-5-methyl-2-phenoxy)methanetitanium dimethoxide, (η5-3-methylcyclopentadienyl)(2-phenoxy) dimethylmethanetitanium dimethoxide, (η5-3-methylcyclopentadienyl)(3,4-dimethyl-2-phenoxy) dimethylmethanetitanium dimethoxide, (η5-3-methylcyclopentadienyl)(3-tert-butyl-5-methyl-2-phenoxy)dimethylmethanetitanium dimethoxide, (η5-3-methylcyclopentadienyl)(3-tert-butyl-5-methoxy-2- phenoxy)dimethylmethanetitanium dimethoxide, (η5-3-methylcyclopentadienyl)(3-tert-butyl-2-phenoxy) dimethylmethanetitanium dimethoxide, (η5-3-methylcyclopentadienyl)(3-tert-butyl-5-chloro-2-phenoxy)dimethylmethanetitanium dimethoxide, (η5-3-methylcyclopentadienyl)(3-phenyl-2-phenoxy) dimethylmethanetitanium dimethoxide, (η5-3-methylcyclopentadienyl)(3-tert-butyldimethylsilyl-5-methyl-2-phenoxy)dimethylmethanetitanium dimethoxide, (η5-3-methylcyclopentadienyl)(3-trimethylsilyl-5-methyl-2-phenoxy) dimethylmethanetitanium dimethoxide, (η5-3-methylcyclopentadienyl)(2-phenoxy) diphenylmathanetitanium dimethoxide, (η5-3-methylcyclopentadienyl)(3,4-dimethyl-2-phenoxy) diphenylmathanetitanium dimethoxide, (η5-3-methylcyclopentadienyl)(3-tert-butyl-5-methyl-2-phenoxy)diphenylmathanetitanium dimethoxide, (η5-3-methylcyclopentadienyl)(3-tert-butyl-5-methoxy-2-phenoxy)diphenylmathanetitanium dimethoxide, (η5-3-methylcyclopentadienyl)(3-tert-butyl-2-phenoxy) diphenylmathanetitanium dimethoxide, (η5-3-methylcyclopentadienyl)(3-tert-butyl-5-chloro-2-phenoxy)diphenylmathanetitanium dimethoxide, (η5-3-methylcyclopentadienyl)(3-phenyl-2-phenoxy) diphenylmathanetitanium dimethoxide, (η5-3-methylcyclopentadienyl)(3-tert-butyldimethylsilyl-5-methyl-2-phenoxy)diphenylmathanetitanium dimethoxide, (η5-3-methylcyclopentadienyl)(3-trimethylsilyl-5-methyl-2-phenoxy) diphenylmathanetitanium dimethoxide, (η5-3-tert-butylcyclopentadienyl)(2-phenoxy) methanetitanium dimethoxide, (η5-3-tert-butylcyclopentadienyl)(3,4-dimethyl-2-phenoxy) methanetitanium dimethoxide, (η5-3-tert-butylcyclopentadienyl)(3-tert-butyl-5-methyl-2-phenoxy)methanetitanium dimethoxide, (η5-3-tert-butylcyclopentadienyl)(3-tert-butyl-5-methoxy-2-phenoxy)methanetitanium dimethoxide, (η5-3-tert-butylcyclopentadienyl)(3-tert-butyl-2-phenoxy) methanetitanium dimethoxide, (η5-3-tert-butylcyclopentadienyl)(3-tert-butyl-5-chloro-2-phenoxy)methanetitanium dimethoxide, (η5-3-tert-butylcyclopentadienyl)(3-phenyl-2-phenoxy) methanetitanium dimethoxide, (η5-3-tert-butylcyclopentadienyl)(3-tert-butyldimethylsilyl-5-methyl-2-phenoxy)methanetitanium dimethoxide, (η5-3-tert-butylcyclopentadienyl)(3-trimethylsilyl-5-methyl-2-phenoxy)methanetitanium dimethoxide, (η5-3-tert-butylcyclopentadienyl)(2-phenoxy) dimethylmethanetitanium dimethoxide, (η5-3-tert-butylcyclopentadienyl)(3,4-dimethyl-2-phenoxy) dimethylmethanetitanium dimethoxide, (η5-3-tert-butylcyclopentadienyl)(3-tert-butyl-5-methyl-2-phenoxy)dimethylmethanetitanium dimethoxide, (η5-3-tert-butylcyclopentadienyl)(3-tert-butyl-5-methoxy-2-phenoxy)dimethylmethanetitanium dimethoxide, (η5-3-tert-butylcyclopentadienyl)(3-tert-butyl-2-phenoxy)dimethylmethanetitanium dimethoxide, (η5-3-tert-butylcyclopentadienyl)(3-tert-butyl-5-chloro-2-phenoxy)dimethylmethanetitanium dimethoxide, (η5-3-tert-butylcyclopentadienyl)(3-phenyl-2-phenoxy) dimethylmethanetitanium dimethoxide, (η5-3-tert-butylcyclopentadienyl)(3-tert-butyldimethylsilyl-5-methyl-2-phenoxy)dimethylmethanetitanium dimethoxide, (η5-3-tert-butylcyclopentadienyl)(3-trimethylsilyl-5-methyl-2-phenoxy) dimethylmethanetitanium dimethoxide, (η5-3-tert-butylcyclopentadienyl)(2-phenoxy) diphenylmethanetitanium dimethoxide, (η5-3-tert-butylcyclopentadienyl)(3,4-dimethyl-2-phenoxy) diphenylmethanetitanium dimethoxide, (η5-3-tert-butylcyclopentadienyl)(3-tert-butyl-5-methyl-2-phenoxy)diphenylmethanetitanium dimethoxide, (η5-3-tert-butylcyclopentadienyl)(3-tert-butyl-5-methoxy-2-phenoxy)diphenylmethanetitanium dimethoxide, (η5-3-tert-butylcyclopentadienyl)(3-tert-butyl-2-phenoxy)diphenylmethanetitanium dimethoxide, (η5-3-tert-butylcyclopentadienyl)(3-tert-butyl-5-chloro-2-phenoxy)diphenylmethanetitanium dimethoxide, (η5-3-tert-butylcyclopentadienyl)(3-phenyl-2-phenoxy) diphenylmethanetitanium dimethoxide, (η5-3-tert-butylcyclopentadienyl)(3-tert-butyldimethylsilyl-5-methyl-2-phenoxy)diphenylmethanetitanium dimethoxide, (η5-3-tert-butylcyclopentadienyl)(3-trimethylsilyl-5-methyl-2-phenoxy) diphenylmethanetitanium dimethoxide, (η5-cyclopentadienyl)(2-phenoxy)methanetitanium (ethylene dioxide), (η5-cyclopentadienyl)(3,4-dimethyl-2-phenoxy)methanetitanium(ethylene dioxide), (η5-cyclopentadienyl)(3-tert-butyl-5-methyl-2-phenoxy)methanetitanium(ethylene dioxide), (η5-cyclopentadienyl)(3-tert-butyl-5-methoxy-2-phenoxy) methanetitanium(ethylene dioxide), (η5-cyclopentadienyl)(3-tert-butyl-2-phenoxy) methanetitanium(ethylene dioxide), (η5-cyclopentadienyl)(3-tert-butyl-5-chloro-2-phenoxy) methanetitanium(ethylene dioxide), (η5-cyclopentadienyl)(3-phenyl-2-phenoxy) methanetitanium(ethylene dioxide), (η5-cyclopentadienyl)(3-tert-butyldimethylsilyl-5-methyl-2-phenoxy)methanetitanium(ethylene dioxide), (η5-cyclopentadienyl)(3-trimethylsilyl-5-methyl-2-phenoxy)methanetitanium(ethylene dioxide), (η5-cyclopentadienyl)(2-phenoxy) dimethylmethanetitanium(ethylene dioxide), (η5-cyclopentadienyl)(3,4-dimethyl-2-phenoxy) dimethylmethanetitanium(ethylene dioxide), (η5-cyclopentadienyl)(3-tert-butyl-5-methyl-2-phenoxy) dimethylmethanetitanium(ethylene dioxide), (η5-cyclopentadienyl)(3-tert-butyl-5-methoxy-2-phenoxy) dimethylmethanetitanium(ethylene dioxide), (η5-cyclopentadienyl)(3-tert-butyl-2-phenoxy) dimethylmethanetitanium(ethylene dioxide), (η5-cyclopentadienyl)(3-tert-butyl-5-chloro-2-phenoxy) dimethylmethanetitanium(ethylene dioxide), (η5-cyclopentadienyl)(3-phenyl-2-phenoxy) dimethylmethanetitanium(ethylene dioxide), (η5-cyclopentadienyl)(3-tert-butyldimethylsilyl-5-methyl-2-phenoxy)dimethylmethanetitanium(ethylene dioxide), (η5-cyclopentadienyl)(3-trimethylsilyl-5-methyl-2-phenoxy)dimethylmethanetitanium(ethylene dioxide), (η5-cyclopentadienyl)(2-phenoxy) diphenylmethanetitanium(ethylene dioxide), (η5-cyclopentadienyl)(3,4-dimethyl-2-phenoxy) diphenylmethanetitanium(ethylene dioxide), (η5-cyclopentadienyl)(3-tert-butyl-5-methyl-2-phenoxy) diphenylmethanetitanium(ethylene dioxide), (η5-cyclopentadienyl)(3-tert-butyl-5-methoxy-2-phenoxy) diphenylmethanetitanium(ethylene dioxide), (η5-cyclopentadienyl)(3-tert-butyl-2-phenoxy) diphenylmethanetitanium(ethylene dioxide), (η5-cyclopentadienyl)(3-tert-butyl-5-chloro-2-phenoxy) diphenylmethanetitanium(ethylene dioxide), (η5- cyclopentadienyl)(3-phenyl-2-phenoxy) diphenylmethanetitanium(ethylene dioxide), (η5-cyclopentadienyl)(3-tert-butyldimethylsilyl-5-methyl-2-phenoxy)diphenylmethanetitanium(ethylene dioxide), (η5-cyclopentadienyl)(3-trimethylsilyl-5-methyl-2-phenoxy)diphenylmethanetitanium(ethylene dioxide), (η5-2,3,4,5-tetramethylcyclopentadienyl)(2-phenoxy) methanetitanium(ethylene dioxide), (η5-2,3,4,5-tetramethylcyclopentadienyl)(3,4-dimethyl-2-phenoxy)methanetitanium(ethylene dioxide), (η5-2,3,4,5-tetramethylcyclopentadienyl)(3-tert-butyl-5-methyl-2-phenoxy)methanetitanium(ethylene dioxide), (η5-2,3,4,5-tetramethylcyclopentadienyl)(3-tert-butyl-5-methoxy-2-phenoxy)methanetitanium(ethylene dioxide), (η5-2,3,4,5-tetramethylcyclopentadienyl)(3-tert-butyl-2-phenoxy)methanetitanium(ethylene dioxide), (η5-2,3,4,5-tetramethylcyclopentadienyl)(3-tert-butyl-5-chloro-2-phenoxy)methanetitanium(ethylene dioxide), (η5-2,3,4,5-tetramethylcyclopentadienyl)(3-phenyl-2-phenoxy)methanetitanium(ethylene dioxide), (η5-2,3,4,5-tetramethylcyclopentadienyl)(3-tert-butyldimethylsilyl-5-methyl-2-phenoxy)methanetitanium(ethylene dioxide), (η5-2,3,4,5-tetramethylcyclopentadienyl)(3-trimethylsilyl-5-methyl-2-phenoxy)methanetitanium(ethylene dioxide), (η5-2,3,4,5-tetramethylcyclopentadienyl)(2-phenoxy) dimethylmethanetitanium(ethylene dioxide), (η5-2,3,4,5-tetramethylcyclopentadienyl)(3,4-dimethyl-2-phenoxy)dimethylmethanetitanium(ethylene dioxide), (η5-2,3,4,5-tetramethylcyclopentadienyl)(3-tert-butyl-5-methyl-2-phenoxy)dimethylmethanetitanium(ethylene dioxide), (η5-2,3,4,5-tetramethylcyclopentadienyl)(3-tert-butyl-5-methoxy-2-phenoxy)dimethylmethanetitanium(ethylene dioxide), (η5-2,3,4,5-tetramethylcyclopentadienyl)(3-tert-butyl-2-phenoxy)dimethylmethanetitanium(ethylene dioxide), (η5-2,3,4,5-tetramethylcyclopentadienyl)(3-tert-butyl-5-chloro-2-phenoxy)dimethylmethanetitanium(ethylene dioxide), (η5-2,3,4,5-tetramethylcyclopentadienyl)(3-phenyl-2-phenoxy)dimethylmethanetitanium(ethylene dioxide), (η5-2,3,4,5-tetramethylcyclopentadienyl)(3-tert-butyldimethylsilyl-5-methyl-2-phenoxy)dimethylmethanetitanium(ethylene dioxide), (η5-2,3,4,5-tetramethylcyclopentadienyl)(3-trimethylsilyl-5-methyl-2-phenoxy)dimethylmethanetitanium(ethylene dioxide), (η5-2,3,4,5-tetramethylcyclopentadienyl)( 2-phenoxy) diphenylmethanetitanium(ethylene dioxide), (η5-2,3,4,5-tetramethylcyclopentadienyl)(3,4-dimethyl-2-phenoxy)diphenylmethanetitanium(ethylene dioxide), (η5-2,3,4,5-tetramethylcyclopentadienyl)(3-tert-butyl-5-methyl-2-phenoxy)diphenylmethanetitanium (ethylene dioxide), (η5-2,3,4,5-tetramethylcyclopentadienyl)(3-tert-butyl-5-methoxy-2-phenoxy)diphenylmethanetitanium(ethylene dioxide), (η5-2,3,4,5-tetramethylcyclopentadienyl)(3-tert-butyl-2-phenoxy)diphenylmethanetitanium (ethylene dioxide), (η5-2,3,4,5-tetramethylcyclopentadienyl)(3-tert-butyl-5-chloro-2-phenoxy)diphenylmethanetitanium(ethylene dioxide), (η5-2,3,4,5-tetramethylcyclopentadienyl)(3-phenyl-2-phenoxy)diphenylmethanetitanium(ethylene dioxide), (η5-2,3,4,5-tetramethylcyclopentadienyl)(3-tert-butyldimethylsilyl-5-methyl-2-phenoxy) diphenylmethanetitanium(ethylene dioxide), (η5-2,3,4,5-tetramethylcyclopentadienyl)(3-trimethylsilyl-5-methyl-2-phenoxy)diphenylmethanetitanium(ethylene dioxide), (η5-3-methylcyclopentadienyl)(2-phenoxy) methanetitanium(ethylene dioxide), (η5-3-methylcyclopentadienyl)(3,4-dimethyl-2-phenoxy) methanetitanium(ethylene dioxide), (η5-3-methylcyclopentadienyl)(3-tert-butyl-5-methyl-2-phenoxy)methanetitanium(ethylene dioxide), (η5-3-methylcyclopentadienyl)(3-tert-butyl-5-methoxy-2-phenoxy)methanetitanium(ethylene dioxide), (η5-3-methylcyclopentadienyl)(3-tert-butyl-2-phenoxy) methanetitanium(ethylene dioxide), (η5-3-methylcyclopentadienyl)(3-tert-butyl-5-chloro-2-phenoxy)methanetitanium(ethylene dioxide), (η5-3-methylcyclopentadienyl)(3-phenyl-2-phenoxy) methanetitanium(ethylene dioxide), (η5-3-methylcyclopentadienyl)(3-tert-butyldimethylsilyl-5-methyl-2-phenoxy)methanetitanium(ethylene dioxide), (η5-3-methylcyclopentadienyl)(3-trimethylsilyl-5-methyl-2-phenoxy)methanetitanium(ethylene dioxide), (η5-3-methylcyclopentadienyl)(2-phenoxy) dimethylmethanetitanium(ethylene dioxide), (η5-3-methylcyclopentadienyl)(3,4-dimethyl-2-phenoxy) dimethylmethanetitanium(ethylene dioxide), (η5-3-methylcyclopentadienyl)(3-tert-butyl-5-methyl-2-phenoxy)dimethylmethanetitanium(ethylene dioxide), (η5-3-methylcyclopentadienyl)(3-tert-butyl-5-methoxy-2-phenoxy)dimethylmethanetitanium (ethylene dioxide), (η5-3-methylcyclopentadienyl)(3-tert-butyl-2-phenoxy)dimethylmethanetitanium (ethylene dioxide), (η5-3-methylcyclopentadienyl)(3-tert-butyl-5-chloro-2-phenoxy) dimethylmethanetitanium(ethylene dioxide), (η5-3-methylcyclopentadienyl)(3-phenyl-2-phenoxy) dimethylmethanetitanium(ethylene dioxide), (η5-3-methylcyclopentadienyl)(3-tert-butyldimethylsilyl-5-methyl-2-phenoxy)dimethylmethanetitanium(ethylene dioxide), (η5-3-methylcyclopentadienyl)(3-trimethylsilyl-5-methyl-2-phenoxy) dimethylmethanetitanium(ethylene dioxide), (η5-3-methylcyclopentadienyl)(2-phenoxy) diphenylmethanetitanium(ethylene dioxide), (η5-3-methylcyclopentadienyl)(3,4-dimethyl-2-phenoxy) diphenylmethanetitanium(ethylene dioxide), (η5-3-methylcyclopentadienyl)(3-tert-butyl-5-methyl-2-phenoxy)diphenylmethanetitanium(ethylene dioxide), (η5-3-methylcyclopentadienyl)(3-tert-butyl-5-methoxy-2-phenoxy)diphenylmethanetitanium (ethylene dioxide), (η5-3-methylcyclopentadienyl)(3-tert-butyl-2-phenoxy)diphenylmethanetitanium (ethylene dioxide), (η5-3-methylcyclopentadienyl)(3-tert-butyl-5-chloro-2-phenoxy) diphenylmethanetitanium(ethylene dioxide), (η5-3-methylcyclopentadienyl)(3-phenyl-2-phenoxy) diphenylmethanetitanium(ethylene dioxide), (η5-3-methylcyclopentadienyl)(3-tert-butyldimethylsilyl-5-methyl-2-phenoxy)diphenylmethanetitanium(ethylene dioxide), (η5-3-methylcyclopentadienyl)(3-trimethylsilyl-5-methyl- 2-phenoxy) diphenylmethanetitanium(ethylene dioxide), (η5-3-tert-butylcyclopentadienyl)(2-phenoxy) methanetitanium(ethylene dioxide), (η5-3-tert-butylcyclopentadienyl)(3,4-dimethyl-2-phenoxy) methanetitanium(ethylene dioxide), (η5-3-tert-butylcyclopentadienyl)(3-tert-butyl-5-methyl-2- phenoxy)methanetitanium(ethylene dioxide), (η5-3-tert-butylcyclopentadienyl)(3-tert-butyl-5-methoxy-2-phenoxy)methanetitanium(ethylene dioxide), (η5-3-tert-butylcyclopentadienyl)(3-tert-butyl-2-phenoxy) methanetitanium(ethylene dioxide), (η5-3-tert-butylcyclopentadienyl)(3-tert-butyl-5-chloro-2-phenoxy)methanetitanium(ethylene dioxide), (η5-3-tert-butylcyclopentadienyl)(3-phenyl-2-phenoxy) methanetitanium(ethylene dioxide), (η5-3-tert-butylcyclopentadienyl)(3-tert-butyldimethylsilyl-5-methyl-2-phenoxy)methanetitanium(ethylene dioxide), (η5-3-tert-butylcyclopentadienyl)(3-trimethylsilyl-5-methyl-2-phenoxy)methanetitanium(ethylene dioxide), (η5-3-tert-butylcyclopentadienyl)(2-phenoxy) dimethylmethanetitanium(ethylene dioxide), (η5-3-tert-butylcyclopentadienyl)(3,4-dimethyl-2-phenoxy) dimethylmethanetitanium(ethylene dioxide), (η5-3-tert-butylcyclopentadienyl)(3-tert-butyl-5-methyl-2-phenoxy)dimethylmethanetitanium(ethylene dioxide), (η5-3-tert-butylcyclopentadienyl)(3-tert-butyl-5-methoxy-2-phenoxy)dimethylmethanetitanium (ethylene dioxide), (η5-3-tert-butylcyclopentadienyl) (3-tert-butyl-2-phenoxy)dimethylmethanetitanium (ethylene dioxide), (η5-3-tert-butylcyclopentadienyl) (3-tert-butyl-5-chloro-2-phenoxy) dimethylmethanetitanium(ethylene dioxide), (η5-3-tert-butylcyclopentadienyl)(3-phenyl-2-phenoxy) dimethylmethanetitanium(ethylene dioxide), (η5-3-tert-butylcyclopentadienyl)(3-tert-butyldimethylsilyl-5-methyl-2-phenoxy)dimethylmethanetitanium (ethylene dioxide), (η5-3-tert-butylcyclopentadienyl) (3-trimethylsilyl-5-methyl-2-phenoxy) dimethylmethanetitanium(ethylene dioxide), (η5-3-tert-butylcyclopentadienyl)(2-phenoxy) diphenylmethanetitanium(ethylene dioxide), (η5-3-tert-butylcyclopentadienyl)(3,4-dimethyl-2-phenoxy) diphenylmethanetitanium(ethylene dioxide), (η5-3-tert-butylcyclopentadienyl)(3-tert-butyl-5-methyl-2-phenoxy)diphenylmethanetitanium(ethylene dioxide), (η5-3-tert-butylcyclopentadienyl)(3-tert-butyl-5-methoxy-2-phenoxy)diphenylmethanetitanium (ethylene dioxide), (η5-3-tert-butylcyclopentadienyl) (3-tert-butyl-2-phenoxy)diphenylmethanetitanium (ethylene dioxide), (η5-3-tert-butylcyclopentadienyl) (3-tert-butyl-5-chloro-2-phenoxy) diphenylmethanetitanium(ethylene dioxide), (η5-3-tert-butylcyclopentadienyl)(3-phenyl-2-phenoxy) diphenylmethanetitanium(ethylene dioxide), (η5-3-tert-butylcyclopentadienyl)(3-tert-butyldimethylsilyl-5-methyl-2-phenoxy)diphenylmethanetitanium (ethylene dioxide), (η5-3-tert-butylcyclopentadienyl) (3-trimethylsilyl-5-methyl-2-phenoxy) diphenylmethanetitanium(ethylene dioxide), (η5-cyclopentadienyl)(2-phenoxy)methanetitaniumbis (hexafluoro isopropoxide), (η5-cyclopentadienyl)(3,4-dimethyl-2-phenoxy)methanetitaniumbis(hexafluoro isopropoxide), (η5-cyclopentadienyl)(3-tert-butyl-5-methyl-2-phenoxy)methanetitaniumbis(hexafluoro isopropoxide), (η5-cyclopentadienyl)(3-tert-butyl-5-methoxy-2-phenoxy)methanetitaniumbis(hexafluoro isopropoxide), (η5-cyclopentadienyl)(3-tert-butyl-2-phenoxy)methanetitaniumbis(hexafluoro isopropoxide), (η5-cyclopentadienyl)(3-tert-butyl-5-chloro-2-phenoxy)methanetitaniumbis(hexafluoro isopropoxide), (η5-cyclopentadienyl)(3-phenyl-2-phenoxy)methanetitaniumbis(hexafluoro isopropoxide), (η5-cyclopentadienyl)(3-tert-butyldimethylsilyl-5-methyl-2-phenoxy) methanetitaniumbis(hexafluoro isopropoxide), (η5-cyclopentadienyl)(3-trimethylsilyl-5-methyl-2-phenoxy)methanetitaniumbis(hexafluoro isopropoxide), (η5-cyclopentadienyl)(2-phenoxy) dimethylmethanetitaniumbis(hexafluoro isopropoxide), (η5-cyclopentadienyl)(3,4-dimethyl-2-phenoxy)dimethylmethanetitaniumbis(hexafluoro isopropoxide), (η5-cyclopentadienyl)(3-tert-butyl-5-methyl-2-phenoxy)dimethylmethanetitaniumbis (hexafluoro isopropoxide), (η5-cyclopentadienyl)(3-tert-butyl-5-methoxy-2-phenoxy) dimethylmethanetitaniumbis(hexafluoro isopropoxide), (η5-cyclopentadienyl)(3-tert-butyl-2-phenoxy)dimethylmethanetitaniumbis(hexafluoro isopropoxide), (η5-cyclopentadienyl)(3-tert-butyl-5-chloro-2-phenoxy)dimethylmethanetitaniumbis (hexafluoro isopropoxide), (η5-cyclopentadienyl)(3-phenyl-2-phenoxy)dimethylmethanetitaniumbis (hexafluoro isopropoxide), (η5-cyclopentadienyl)(3-tert-butyldimethylsilyl-5-methyl-2-phenoxy) dimethylmethanetitaniumbis(hexafluoro isopropoxide), (η5-cyclopentadienyl)(3-trimethylsilyl-5-methyl-2-phenoxy)dimethylmethanetitaniumbis (hexafluoro isopropoxide), (η5-cyclopentadienyl)(2-phenoxy) diphenylmethanetitaniumbis(hexafluoro isopropoxide), (η5-cyclopentadienyl)(3,4-dimethyl-2-phenoxy) diphenylmethanetitaniumbis(hexafluoro isopropoxide), (η5-cyclopentadienyl)(3-tert-butyl- 5-methyl-2-phenoxy)diphenylmethanetitaniumbis(hexafluoro isopropoxide), (η5-cyclopentadienyl)(3-tert-butyl-5-methoxy-2-phenoxy)diphenylmethanetitaniumbis (hexafluoro isopropoxide), (η5-cyclopentadienyl)(3-tert-butyl-2-5 phenoxy)diphenylmethanetitaniumbis (hexafluoro isopropoxide), (η5-cyclopentadienyl)(3-tert-butyl-5-chloro-2-phenoxy) diphenylmethanetitaniumbis(hexafluoro isopropoxide), (η5-cyclopentadienyl)(3-phenyl-2-phenoxy) diphenylmethanetitaniumbis(hexafluoro isopropoxide), (η5-cyclopentadienyl)(3-tert-butyldimethylsilyl-5-methyl-2-phenoxy)diphenylmethanetitaniumbis (hexafluoro isopropoxide), (η5-cyclopentadienyl)(3-trimethylsilyl-5-methyl-2-phenoxy) diphenylmethanetitaniumbis(hexafluoro isopropoxide), (η5-2,3,4,5-tetramethylcyclopentadienyl)(2-phenoxy) methanetitaniumbis(hexafluoro isopropoxide), (η5-2,3,4,5-tetramethylcyclopentadienyl)(3,4-dimethyl-2-phenoxy)methanetitaniumbis(hexafluoro isopropoxide), (η5-2,3,4,5-tetramethylcyclopentadienyl)(3-tert-butyl-5-methyl-2-phenoxy)methanetitaniumbis(hexafluoro isopropoxide), (η5-2,3,4,5-tetramethylcyclopentadienyl)(3-tert-butyl-5-methoxy-2-phenoxy)methanetitaniumbis(hexafluoro isopropoxide), (η5-2,3,4,5-tetramethylcyclopentadienyl)(3-tert-butyl- 2-phenoxy) methanetitaniumbis(hexafluoro isopropoxide), (η5-2,3,4,5-tetramethylcyclopentadienyl)(3-tert-butyl-5-chloro-2-phenoxy)methanetitaniumbis(hexafluoro isopropoxide), (η5-2,3,4,5-tetramethylcyclopentadienyl)(3-phenyl-2-phenoxy) methanetitaniumbis(hexafluoro isopropoxide), (η5-2,3,4,5-tetramethylcyclopentadienyl)(3-tert-butyldimethylsilyl-5-methyl-2-phenoxy) methanetitaniumbis(hexafluoro isopropoxide), (η5-2,3, 4,5-tetramethylcyclopentadienyl)(3-trimethylsilyl-5-methyl-2-phenoxy)methanetitaniumbis(hexafluoro isopropoxide),
(η5-2,3,4,5-tetramethylcyclopentadienyl)(2-phenoxy) dimethylmethanetitaniumbis(hexafluoro isopropoxide), (η5-2,3,4,5-tetramethylcyclopentadienyl)(3,4-dimethyl-2-phenoxy)dimethylmethanetitaniumbis(hexafluoro isopropoxide), (η5-2,3,4,5-tetramethylcyclopentadienyl)(3-tert-butyl-5-methyl-2-phenoxy)dimethylmethanetitaniumbis(hexafluoro isopropoxide), (η5-2,3,4,5-tetramethylcyclopentadienyl)(3-tert-butyl-5-methoxy-2-phenoxy)dimethylmethanetitaniumbis(hexafluoro isopropoxide), (η5-2,3,4,5-tetramethylcyclopentadienyl)(3-tert-butyl-2-phenoxy)dimethylmethanetitaniumbis(hexafluoro isopropoxide), (η5-2,3,4,5-tetramethylcyclopentadienyl)(3-tert-butyl-5-chloro-2-phenoxy)dimethylmethanetitaniumbis(hexafluoro isopropoxide), (η5-2,3,4,5-tetramethylcyclopentadienyl)(3-phenyl-2-phenoxy)dimethylmethanetitaniumbis(hexafluoro isopropoxide), (η5-2,3,4,5-tetramethylcyclopentadienyl)(3-tert-butyldimethylsilyl-5-methyl-2-phenoxy)dimethylmethanetitaniumbis(hexafluoro isopropoxide), (η5-2,3,4,5-tetramethylcyclopentadienyl)(3-trimethylsilyl-5-methyl-2-phenoxy)dimethylmethanetitaniumbis (hexafluoro isopropoxide), (η5-2,3,4,5-tetramethylcyclopentadienyl)(2-phenoxy) diphenylmethanetitaniumbis(hexafluoro isopropoxide), (η5-2,3,4,5-tetramethylcyclopentadienyl)(3,4-dimethyl-2-phenoxy)diphenylmethanetitaniumbis (hexafluoro isopropoxide), (η5-2,3,4,5-tetramethylcyclopentadienyl)(3-tert-butyl-5-methyl-2-phenoxy)diphenylmethanetitaniumbis(hexafluoro isopropoxide), (η5-2,3,4,5-tetramethylcyclopentadienyl)(3-tert-butyl-5-methoxy-2-phenoxy)diphenylmethanetitaniumbis(hexafluoro isopropoxide), (η5-2,3,4,5-tetramethylcyclopentadienyl)(3-tert-butyl-2-phenoxy) diphenylmethanetitaniumbis(hexafluoro isopropoxide), (η5-2,3,4,5-tetramethylcyclopentadienyl)(3-tert-butyl-5-chloro-2-phenoxy)diphenylmethanetitaniumbis (hexafluoro isopropoxide), (η5-2,3,4,5-tetramethylcyclopentadienyl)(3-phenyl-2-phenoxy) diphenylmethanetitaniumbis(hexafluoro isopropoxide), (η5-2,3,4,5-tetramethylcyclopentadienyl)(3-tert-butyldimethylsilyl-5-methyl-2-phenoxy) diphenylmethanetitaniumbis(hexafluoro isopropoxide), (η5-2,3,4,5-tetramethylcyclopentadienyl)(3-trimethylsilyl-5-methyl-2-phenoxy) diphenylmethanetitaniumbis(hexafluoro isopropoxide),
(η5-3-methylcyclopentadienyl)(2-phenoxy) methanetitaniumbis(hexafluoro isopropoxide), (η5-3-methylcyclopentadienyl)(3,4-dimethyl-2-phenoxy) methanetitaniumbis(hexafluoro isopropoxide), (η5-3-methylcyclopentadienyl)(3-tert-butyl-5-methyl-2-phenoxy)methanetitaniumbis(hexafluoro isopropoxide), (η5-3-methylcyclopentadienyl)(3-tert-butyl-5-methoxy-2-phenoxy)methanetitaniumbis (hexafluoro isopropoxide), (η5-3-methylcyclopentadienyl)(3-tert-butyl-2-phenoxy) methanetitaniumbis(hexafluoro isopropoxide), (η5-3-methylcyclopentadienyl)(3-tert-butyl-5-chloro-2-phenoxy)methanetitaniumbis(hexafluoro isopropoxide), (η5-3-methylcyclopentadienyl)(3-phenyl-2-phenoxy)methanetitaniumbis(hexafluoro isopropoxide), (η5-3-methylcyclopentadienyl)(3-tert-butyldimethylsilyl-5-methyl-2-phenoxy) methanetitaniumbis(hexafluoro isopropoxide), (η5-3-methylcyclopentadienyl)(3-trimethylsilyl-5-methyl-2-phenoxy)methanetitaniumbis(hexafluoro isopropoxide),
(η5-3-methylcyclopentadienyl)(2-phenoxy) dimethylmethanetitaniumbis(hexafluoro isopropoxide), (η5-3-methylcyclopentadienyl)(3,4-dimethyl-2-phenoxy)dimethylmethanetitaniumbis (hexafluoro isopropoxide), (η5-3-methylcyclopentadienyl)(3-tert-butyl-5-methyl-2-phenoxy)dimethylmethanetitaniumbis(hexafluoro isopropoxide), (η5-3-methylcyclopentadienyl)(3-tert-butyl-5-methoxy-2-phenoxy) dimethylmethanetitaniumbis(hexafluoro isopropoxide), (η5-3-methylcyclopentadienyl)(3-tert-butyl-2-phenoxy)dimethylmethanetitaniumbis (hexafluoro isopropoxide), (η5-3-methylcyclopentadienyl)(3-tert-butyl-5-chloro-2-phenoxy)dimethylmethanetitaniumbis(hexafluoro isopropoxide), (η5-3-methylcyclopentadienyl)(3-phenyl-2-phenoxy)dimethylmethanetitaniumbis (hexafluoro isopropoxide), (η5-3-methylcyclopentadienyl)(3-tert-butyldimethylsilyl-5-methyl-2-phenoxy)dimethylmethanetitaniumbis (hexafluoro isopropoxide), (η5-3-methylcyclopentadienyl)(3-trimethylsilyl-5-methyl-2-phenoxy)dimethylmethanetitaniumbis(hexafluoro isopropoxide),
(η5-3-methylcyclopentadienyl)(2-phenoxy) diphenylmethanetitaniumbis(hexafluoro isopropoxide), (η5-3-methylcyclopentadienyl)(3,4-dimethyl-2-phenoxy)diphenylmethanetitaniumbis(hexafluoro isopropoxide), (η5-3-methylcyclopentadienyl)(3-tert-butyl-5-methyl-2-phenoxy) diphenylmethanetitaniumbis(hexafluoro isopropoxide), (η5-3-methylcyclopentadienyl)(3-tert-butyl-5-methoxy-2-phenoxy)diphenylmethanetitaniumbis (hexafluoro isopropoxide), (η5-3-methylcyclopentadienyl)(3-tert-butyl-2-phenoxy) diphenylmethanetitaniumbis(hexafluoro isopropoxide), (η5-3-methylcyclopentadienyl)(3-tert-butyl-5-chloro-2-phenoxy)diphenylmethanetitaniumbis(hexafluoro isopropoxide), (η5-3-methylcyclopentadienyl)(3-phenyl-2-phenoxy)diphenylmethanetitaniumbis (hexafluoro isopropoxide), (η5-3-methylcyclopentadienyl)(3-tert-butyldimethylsilyl-5-methyl-2-phenoxy)diphenylmethanetitaniumbis (hexafluoro isopropoxide), (η5-3-methylcyclopentadienyl)(3-trimethylsilyl-5-methyl-2-phenoxy)diphenylmethanetitaniumbis(hexafluoro isopropoxide),
(η5-3-tert-butylcyclopentadienyl)(2-phenoxy) methanetitaniumbis(hexafluoro isopropoxide), (η5-3-tert-butylcyclopentadienyl)(3,4-dimethyl-2-phenoxy) methanetitaniumbis(hexafluoro isopropoxide), (η5-3-tert-butylcyclopentadienyl)(3-tert-butyl-5-methyl-2-phenoxy)methanetitaniumbis(hexafluoro isopropoxide), (η5-3-tert-butylcyclopentadienyl)(3-tert-butyl-5-methoxy-2-phenoxy)methanetitaniumbis (hexafluoro isopropoxide), (η5-3-tert-butylcyclopentadienyl)(3-tert-butyl-2-phenoxy) methanetitaniumbis(hexafluoro isopropoxide), (η5-3- tert-butylcyclopentadienyl)(3-tert-butyl-5-chloro-2-phenoxy)methanetitaniumbis(hexafluoro isopropoxide), (η5-3-tert-butylcyclopentadienyl)(3-phenyl-2-phenoxy)methanetitaniumbis(hexafluoro isopropoxide), (η5-3-tert-butylcyclopentadienyl)(3-tert-butyldimethylsilyl-5-methyl-2-phenoxy) methanetitaniumbis(hexafluoro isopropoxide), (η5-3-tert-butylcyclopentadienyl)(3-trimethylsilyl-5-methyl-2-phenoxy)methanetitaniumbis(hexafluoro isopropoxide), (η5-3-tert-butylcyclopentadienyl)(2-phenoxy) dimethylmethanetitaniumbis(hexafluoro isopropoxide), (η5-3-tert-butylcyclopentadienyl)(3,4-dimethyl-2-phenoxy)dimethylmethanetitaniumbis (hexafluoro isopropoxide), (η5-3-tert-butylcyclopentadienyl)(3-tert-butyl-5-methyl-2-phenoxy)dimethylmethanetitaniumbis(hexafluoro isopropoxide), (η5-3-tert-butylcyclopentadienyl)(3-tert-butyl-5-methoxy-2-phenoxy) dimethylmethanetitaniumbis(hexafluoro isopropoxide), (η5-3-tert-butylcyclopentadienyl)(3-tert-butyl-2-phenoxy)dimethylmethanetitaniumbis (hexafluoro isopropoxide), (η5-3-tert-butylcyclopentadienyl)(3-tert-butyl-5-chloro-2-phenoxy)dimethylmethanetitaniumbis(hexafluoro isopropoxide), (η5-3-tert-butylcyclopentadienyl)(3-phenyl-2-phenoxy)dimethylmethanetitaniumbis (hexafluoro isopropoxide), (η5-3-tert-butylcyclopentadienyl)(3-tert-butyldimethylsilyl-5-methyl-2-phenoxy)dimethylmethanetitaniumbis (hexafluoro isopropoxide), (η5-3-tert-butylcyclopentadienyl)( 3-trimethylsilyl-5-methyl-2-phenoxy)dimethylmethanetitaniumbis(hexafluoro isopropoxide), (η5-3-tert-butylcyclopentadienyl)(2-phenoxy) diphenylmethanetitaniumbis(hexafluoro isopropoxide), (η5-3-tert-butylcyclopentadienyl)(3,4-dimethyl-2-phenoxy)diphenylmethanetitaniumbis(hexafluoro isopropoxide), (η5-3-tert-butylcyclopentadienyl)(3-tert-butyl-5-methyl-2-phenoxy) diphenylmethanetitaniumbis(hexafluoro isopropoxide), (η5-3-tert-butylcyclopentadienyl)(3-tert-butyl-5-methoxy-2-phenoxy)diphenylmethanetitaniumbis (hexafluoro isopropoxide), (η5-3-tert-butylcyclopentadienyl)(3-tert-butyl-2-phenoxy) diphenylmethanetitaniumbis (hexafluoro isopropoxide), (η5-3-tert-butylcyclopentadienyl)(3-tert-butyl-5-chloro-2-phenoxy) diphenylmethanetitaniumbis (hexafluoro isopropoxide), (η5-3-tert-butylcyclopentadienyl)(3-phenyl-2-phenoxy) diphenylmethanetitaniumbis (hexafluoro isopropoxide), (η5-3-tert-butylcyclopentadienyl)(3-tert-butyldimethylsilyl-5-methyl-2-phenoxy) diphenylmethanetitaniumbis (hexafluoro isopropoxide), (η5-3-tert-butylcyclopentadienyl)( 3-trimethylsilyl-5-methyl-2-phenoxy)diphenylmethanetitaniumbis(hexafluoro isopropoxide), and compounds obtained by substituting η5-2-methylcyclopentadienyl, η5-2-tert-butylcyclopentadienyl, η5-2-n-butylcyclopentadienyl, η5-3-n-butylcyclopentadienyl, η5-indenyl, η5-fluorenyl for η5-cyclopentadienyl on the above-described compounds, further, compounds obtained by substituting diethoxide, dipropoxide, diisopropoxide, dibutoxide, 1,2-diphenylethylene dioxide, cyclohexane-1,2-dioxide, dibenzyl oxide and the like for dimethoxide on the above-described compounds; and the like.

Examples of the alkoxytitanium complex (I) in which A represents a silicon atom obtained according to the present invention include (η5-cyclopentadienyl)(2-phenoxy) dimethylsilanetitanium dimethoxide, (η5-cyclopentadienyl) (3,4-dimethyl-2-phenoxy)dimethylsilanetitanium dimethoxide, (η5-cyclopentadienyl)(3-tert-butyl-5-methyl-2-phenoxy)dimethylsilanetitanium dimethoxide, (η5-cyclopentadienyl)(3-tert-butyl-5-methoxy-2-phenoxy) dimethylsilanetitanium dimethoxide, (η5-cyclopentadienyl) (3-tert-butyl-2-phenoxy)dimethylsilanetitanium dimethoxide, (η5-cyclopentadienyl)(3-tert-butyl-5-chloro-2-phenoxy)dimethylsilanetitanium dimethoxide, (η5-cyclopentadienyl)(3-phenyl-2-phenoxy) dimethylsilanetitanium dimethoxide, (η5-cyclopentadienyl) (3-tert-butyldimethylsilyl-5-methyl-2-phenoxy) dimethylsilanetitanium dimethoxide, (η5-cyclopentadienyl) (3-trimethylsilyl-5-methyl-2-phenoxy) dimethylsilanetitanium dimethoxide, (η5-cyclopentadienyl)(2-phenoxy) diphenylsilanetitanium dimethoxide, (η5-cyclopentadienyl)(3,4-dimethyl-2-phenoxy) diphenylsilanetitanium dimethoxide, (η5-cyclopentadienyl)(3-tert-butyl-5-methyl-2-phenoxy) diphenylsilanetitanium dimethoxide, (η5-cyclopentadienyl)(3-tert-butyl-5-methoxy-2-phenoxy) diphenylsilanetitanium dimethoxide, (η5-cyclopentadienyl)(3-tert-butyl-2-phenoxy) diphenylsilanetitanium dimethoxide, (η5-cyclopentadienyl)(3-tert-butyl-5-chloro-2-phenoxy) diphenylsilanetitanium dimethoxide, (η5-cyclopentadienyl)(3-phenyl-2-phenoxy) diphenylsilanetitanium dimethoxide, (η5-cyclopentadienyl)(3-tert-butyldimethylsilyl-5-methyl-2-phenoxy)diphenylsilanetitanium dimethoxide, (η5-cyclopentadienyl)(3-trimethylsilyl-5-methyl-2-phenoxy)diphenylsilanetitanium dimethoxide, (η5-2,3,4,5-tetramethylcyclopentadienyl)(2-phenoxy) dimethylsilanetitanium dimethoxide, (η5-2,3,4,5-tetramethylcyclopentadienyl)(3,4-dimethyl-2-phenoxy)dimethylsilanetitanium dimethoxide, (η5-2,3,4,5-tetramethylcyclopentadienyl)(3-tert-butyl-5-methyl-2-phenoxy)dimethylsilanetitanium dimethoxide, (η5-2,3,4,5-tetramethylcyclopentadienyl)(3-tert-butyl-5-methoxy-2-phenoxy)dimethylsilanetitanium dimethoxide, (η5-2,3,4,5-tetramethylcyclopentadienyl)(3-tert-butyl-2-phenoxy)dimethylsilanetitanium dimethoxide, (η5-2,3,4,5-tetramethylcyclopentadienyl)(3-tert-butyl-5-chloro-2-phenoxy)dimethylsilanetitanium dimethoxide, (η5-2,3,4,5-tetramethylcyclopentadienyl)(3-phenyl-2-phenoxy) dimethylsilanetitanium dimethoxide, (η5-2,3,4,5-tetramethylcyclopentadienyl)(3-tert-butyldimethylsilyl-5-methyl-2-phenoxy) dimethylsilanetitanium dimethoxide, (η5-2,3,4,5-tetramethylcyclopentadienyl)(3-trimethylsilyl-5-methyl-2-phenoxy)dimethylsilanetitanium dimethoxide, (η5-2,3,4,5-tetramethylcyclopentadienyl)(2-phenoxy) diphenylsilanetitanium dimethoxide, (η5-2,3,4,5-tetramethylcyclopentadienyl)(3,4-dimethyl-2-phenoxy)diphenylsilanetitanium dimethoxide, (η5-2,3,4,5-tetramethylcyclopentadienyl)(3-tert-butyl-5-methyl-2-phenoxy)diphenylsilanetitanium dimethoxide, (η5-2,3,4,5-tetramethylcyclopentadienyl)(3-tert-butyl-5-methoxy-2-phenoxy)diphenylsilanetitanium dimethoxide, (η5-2, 3,4,5-tetramethylcyclopentadienyl)(3-tert-butyl-2-phenoxy)diphenylsilanetitanium dimethoxide, (η5-2,3,4,5-tetramethylcyclopentadienyl)(3-tert-butyl-5-chloro-2-phenoxy)diphenylsilanetitanium dimethoxide, (η5-2,3,4,5-tetramethylcyclopentadienyl)(3-phenyl-2-phenoxy)diphenylsilanetitanium dimethoxide, (η5-2,3,4,5-tetramethylcyclopentadienyl)(3-tert-butyldimethylsilyl-5-methyl-2-phenoxy)diphenylsilanetitanium dimethoxide, (η5-2,3,4,5-tetramethylcyclopentadienyl)(3-trimethylsilyl-5-methyl-2-phenoxy)diphenylsilanetitanium dimethoxide, (η5-indenyl)(2-phenoxy)dimethylsilanetitanium dimethoxide, (η5-indenyl)(3,4-dimethyl-2-phenoxy) dimethylsilanetitanium dimethoxide, (η5-indenyl)(3-tert-butyl-5-methyl-2-phenoxy)dimethylsilanetitanium dimethoxide, (η5-indenyl)(3-tert-butyl-5-methoxy-2-phenoxy)dimethylsilanetitanium dimethoxide, (η5-indenyl)(3-tert-butyl-2-phenoxy) dimethylsilanetitanium dimethoxide, (η5-indenyl)(3-tert-butyl-5-chloro-2-phenoxy)dimethylsilanetitanium dimethoxide, (η5-indenyl)(3-phenyl-2-phenoxy) dimethylsilanetitanium dimethoxide, (η5-indenyl)(3-tert-butyldimethylsilyl- 5-methyl-2-phenoxy) dimethylsilanetitanium dimethoxide, (η5-indenyl)(3-trimethylsilyl-5-methyl-2-phenoxy) dimethylsilanetitanium dimethoxide, (η5-indenyl)(2-phenoxy)diphenylsilanetitanium dimethoxide, (η5-indenyl)(3,4-dimethyl-2-phenoxy) diphenylsilanetitanium dimethoxide, (η5-indenyl)(3-tert-butyl-5-methyl-2-phenoxy)diphenylsilanetitanium dimethoxide, (η5-indenyl)(3-tert-butyl-5-methoxy-2-phenoxy)diphenylsilanetitanium dimethoxide, (η5-indenyl)(3-tert-butyl-2-phenoxy) diphenylsilanetitanium dimethoxide, (η5-indenyl)(3-tert-butyl-5-chloro-2-phenoxy)diphenylsilanetitanium dimethoxide, (η5-indenyl)(3-phenyl-2-phenoxy) diphenylsilanetitanium dimethoxide, (η5-indenyl)(3-tert-butyldimethylsilyl-5-methyl-2-phenoxy) diphenylsilanetitanium dimethoxide, (η5-indenyl)(3-trimethylsilyl-5-methyl-2-phenoxy) diphenylsilanetitanium dimethoxide, (η5-3-tert-butylcyclopentadienyl)(2-phenoxy) dimethylsilanetitanium dimethoxide, (η5-3-tert-butylcyclopentadienyl)(3,4-dimethyl-2-phenoxy) dimethylsilanetitanium dimethoxide, (η5-3-tert-butylcyclopentadienyl)(3-tert-butyl-5-methyl-2-phenoxy)dimethylsilanetitanium dimethoxide, (η5-3-tert-butylcyclopentadienyl)(3-tert-butyl-5-methoxy-2-phenoxy)dimethylsilanetitanium dimethoxide, (η5-3-tert-butylcyclopentadienyl)(3-tert-butyl-2-phenoxy) dimethylsilanetitanium dimethoxide, (η5-3-tert-butylcyclopentadienyl)(3-tert-butyl-5-chloro-2-phenoxy)dimethylsilanetitanium dimethoxide, (η5-3-tert-butylcyclopentadienyl)(3-phenyl-2-phenoxy) dimethylsilanetitanium dimethoxide, (η5-3-tert-butylcyclopentadienyl)(3-tert-butyldimethylsilyl-5-methyl-2-phenoxy)dimethylsilanetitanium dimethoxide, (η5-3-tert-butylcyclopentadienyl)(3-trimethylsilyl-5-methyl-2-phenoxy) dimethylsilanetitanium dimethoxide, (η5-3-tert-butylcyclopentadienyl)(2-phenoxy) diphenylsilanetitanium dimethoxide, (η5-3-tert-butylcyclopentadienyl)(3,4-dimethyl-2-phenoxy) diphenylsilanetitanium dimethoxide, (η5-3-tert-butylcyclopentadienyl)(3-tert-butyl-5-methyl-2-phenoxy)diphenylsilanetitanium dimethoxide, (η5-3-tert-butylcyclopentadienyl)(3-tert-butyl-5-methoxy-2-phenoxy)diphenylsilanetitanium dimethoxide, (η5-3-tert-butylcyclopentadienyl)(3-tert-butyl-2-phenoxy) diphenylsilanetitanium dimethoxide, (η5-3-tert-butylcyclopentadienyl)(3-tert-butyl-5-chloro-2-phenoxy)diphenylsilanetitanium dimethoxide, (η5-3-tert-butylcyclopentadienyl)(3-phenyl-2-phenoxy) diphenylsilanetitanium dimethoxide, (η5- 3-tert-butylcyclopentadienyl)(3-tert-butyldimethylsilyl-5-methyl-2-phenoxy)diphenylsilanetitanium dimethoxide, (η5-3-tert-butylcyclopentadienyl)(3-trimethylsilyl-5-methyl-2-phenoxy) diphenylsilanetitanium dimethoxide, (η5-cyclopentadienyl)(2-phenoxy) dimethylsilanetitanium(ethylene dioxide), (η5-cyclopentadienyl)(3,4-dimethyl-2-phenoxy) dimethylsilanetitanium(ethylene dioxide), (η5-cyclopentadienyl)(3-tert-butyl-5-methyl-2-phenoxy) dimethylsilanetitanium(ethylene dioxide), (η5-cyclopentadienyl)(3-tert-butyl-5-methoxy-2-phenoxy) dimethylsilanetitanium(ethylene dioxide), (η5-cyclopentadienyl)(3-tert-butyl-2-phenoxy) dimethylsilanetitanium(ethylene dioxide), (η5-cyclopentadienyl)(3-tert-butyl-5-chloro-2-phenoxy) dimethylsilanetitanium(ethylene dioxide), (η5-cyclopentadienyl)(3-phenyl-2-phenoxy) dimethylsilanetitanium(ethylene dioxide), (η5-cyclopentadienyl)(3-tert-butyldimethylsilyl-5-methyl-2-phenoxy)dimethylsilanetitanium(ethylene dioxide), (η5-cyclopentadienyl)(3-trimethylsilyl-5-methyl-2-phenoxy)dimethylsilanetitanium(ethylene dioxide), (η5-cyclopentadienyl)(2-phenoxy) diphenylsilanetitanium(ethylene dioxide), (η5-cyclopentadienyl)(3,4-dimethyl- 2-phenoxy) diphenylsilanetitanium(ethylene dioxide), (η5-cyclopentadienyl)(3-tert-butyl-5-methyl-2-phenoxy) diphenylsilanetitanium(ethylene dioxide), (η5-cyclopentadienyl)(3-tert-butyl-5-methoxy-2-phenoxy) diphenylsilanetitanium(ethylene dioxide), (η5-cyclopentadienyl)(3-tert-butyl-2-phenoxy) diphenylsilanetitanium(ethylene dioxide), (η5-cyclopentadienyl)(3-tert-butyl-5-chloro-2-phenoxy) diphenylsilanetitanium(ethylene dioxide), (η5-cyclopentadienyl)(3-phenyl-2-phenoxy) diphenylsilanetitanium(ethylene dioxide), (η5-cyclopentadienyl)(3-tert-butyldimethylsilyl-5-methyl-2-phenoxy)diphenylsilanetitanium(ethylene dioxide), (η5-cyclopentadienyl)(3-trimethylsilyl-5-methyl-2-phenoxy)diphenylsilanetitanium(ethylene dioxide), (η5-2,3,4,5-tetramethylcyclopentadienyl)(2-phenoxy) dimethylsilanetitanium(ethylene dioxide), (η5-2,3,4,5-tetramethylcyclopentadienyl)(3,4-dimethyl-2-phenoxy)dimethylsilanetitanium(ethylene dioxide), (η5-2,3,4,5-tetramethylcyclopentadienyl)(3-tert-butyl-5-methyl-2-phenoxy)dimethylsilanetitanium (ethylene dioxide), (η5-2,3,4,5-tetramethylcyclopentadienyl)(3-tert-butyl-5-methoxy-2-phenoxy) dimethylsilanetitanium(ethylene dioxide), (η5-2,3,4,5-tetramethylcyclopentadienyl)(3-tert-butyl-2-phenoxy) dimethylsilanetitanium(ethylene dioxide), (η5-2,3,4,5-tetramethylcyclopentadienyl)(3-tert-butyl-5-chloro-2-phenoxy)dimethylsilanetitanium(ethylene dioxide), (η5-2,3,4,5-tetramethylcyclopentadienyl)(3-phenyl-2-phenoxy)dimethylsilanetitanium(ethylene dioxide), (η5-2,3,4,5-tetramethylcyclopentadienyl)(3-tert-butyldimethylsilyl-5-methyl-2-phenoxy)

dimethylsilanetitanium(ethylene dioxide), (η5-2,3,4,5-tetramethylcyclopentadienyl)(3-trimethylsilyl-5-methyl-2-phenoxy)dimethylsilanetitanium(ethylene dioxide), (η5-2,3,4,5-tetramethylcyclopentadienyl)(2-phenoxy) diphenylsilanetitanium(ethylene dioxide), (η5-2,3,4,5-tetramethylcyclopentadienyl)(3,4-dimethyl-2-phenoxy)diphenylsilanetitanium(ethylene dioxide), (η5-2,3,4,5-tetramethylcyclopentadienyl)(3-tert-butyl-5-methyl-2-phenoxy)diphenylsilanetitanium(ethylene dioxide), (η5-2,3,4,5-tetramethylcyclopentadienyl)(3-tert-butyl-5-methoxy-2-phenoxy) diphenylsilanetitanium(ethylene dioxide), (η5-2,3,4,5-tetramethylcyclopentadienyl)(3-tert-butyl-2-phenoxy) diphenylsilanetitanium(ethylene dioxide), (η5-2,3,4,5-tetramethylcyclopentadienyl)(3-tert-butyl-5-chloro-2-phenoxy)diphenylsilanetitanium(ethylene dioxide), (η5-2,3,4,5-tetramethylcyclopentadienyl)(3-phenyl-2-phenoxy)diphenylsilanetitanium(ethylene dioxide), (η5-2,3,4,5-tetramethylcyclopentadienyl)(3-tert-butyldimethylsilyl-5-methyl-2-phenoxy) diphenylsilanetitanium(ethylene dioxide), (η5-2,3,4,5-tetramethylcyclopentadienyl)(3-trimethylsilyl-5-methyl-2-phenoxy)diphenylsilanetitanium(ethylene dioxide), (η5-indenyl)(2-phenoxy)dimethylsilanetitanium(ethylene dioxide), (η5-indenyl)(3,4-dimethyl-2-phenoxy) dimethylsilanetitanium(ethylene dioxide), (η5-indenyl)(3-tert-butyl-5-methyl-2-phenoxy) dimethylsilanetitanium(ethylene dioxide), (η5-indenyl)(3-tert-butyl-5-methoxy-2-phenoxy) dimethylsilanetitanium(ethylene dioxide), (η5-indenyl)(3-tert-butyl-2-phenoxy) dimethylsilanetitanium(ethylene dioxide), (η5-indenyl)(3-tert-butyl-5-chloro-2-phenoxy) dimethylsilanetitanium(ethylene dioxide), (η5-indenyl)(3-phenyl-2-phenoxy)dimethylsilanetitanium (ethylene dioxide), (η5-indenyl)(3-tert-butyldimethylsilyl-5-methyl-2-phenoxy) dimethylsilanetitanium(ethylene dioxide), (η5-indenyl)(3-trimethylsilyl-5-methyl-2-phenoxy) dimethylsilanetitanium(ethylene dioxide), (η5-indenyl)(2-phenoxy)diphenylsilanetitanium(ethylene dioxide), (η5-indenyl)(3,4-dimethyl-2-phenoxy) diphenylsilanetitanium(ethylene dioxide), (η5-indenyl) (3-tert-butyl-5-methyl-2-phenoxy) diphenylsilanetitanium(ethylene dioxide), (η5-indenyl) (3-tert-butyl-5-methoxy-2-phenoxy) diphenylsilanetitanium(ethylene dioxide), (η5-indenyl) (3-tert-butyl-2-phenoxy)diphenylsilanetitanium (ethylene dioxide), (η5-indenyl)(3-tert-butyl-5-chloro-2-phenoxy)diphenylsilanetitanium(ethylene dioxide), (η5-indenyl)(3-phenyl-2-phenoxy) diphenylsilanetitanium(ethylene dioxide), (η5-indenyl) (3-tert-butyldimethylsilyl-5-methyl-2-phenoxy) diphenylsilanetitanium(ethylene dioxide), (η5-indenyl) (3-trimethylsilyl-5-methyl-2-phenoxy) diphenylsilanetitanium(ethylene dioxide), (η5-3-tert-butylcyclopentadienyl)(2-phenoxy) dimethylsilanetitanium(ethylene dioxide), (η5-3-tert-butylcyclopentadienyl)(3,4-dimethyl-2-phenoxy) dimethylsilanetitanium(ethylene dioxide), (η5-3-tert-butylcyclopentadienyl)(3-tert-butyl-5-methyl-2-phenoxy)dimethylsilanetitanium(ethylene dioxide), (η5-3-tert-butylcyclopentadienyl)(3-tert-butyl-5-methoxy-2-phenoxy)dimethylsilanetitanium(ethylene dioxide), (η5-3-tert-butylcyclopentadienyl)(3-tert-butyl-2-phenoxy)dimethylsilanetitanium(ethylene dioxide), (η5-3-tert-butylcyclopentadienyl)(3-tert-butyl-5-chloro-2-phenoxy)dimethylsilanetitanium (ethylene dioxide), (η5-3-tert-butylcyclopentadienyl) (3-phenyl-2-phenoxy)dimethylsilanetitanium(ethylene dioxide), (η5-3-tert-butylcyclopentadienyl)(3-tert-butyldimethylsilyl-5-methyl-2-phenoxy) dimethylsilanetitanium(ethylene dioxide), (η5-3-tert-butylcyclopentadienyl)(3-trimethylsilyl-5-methyl-2-phenoxy)dimethylsilanetitanium(ethylene dioxide), (η5-3-tert-butylcyclopentadienyl)(2-phenoxy) diphenylsilanetitanium(ethylene dioxide), (η5-3-tert-butylcyclopentadienyl)(3,4-dimethyl-2-phenoxy) diphenylsilanetitanium(ethylene dioxide), (η5-3-tert-butylcyclopentadienyl)(3-tert-butyl-5-methyl-2-phenoxy)diphenylsilanetitanium(ethylene dioxide), (η5-3-tert-butylcyclopentadienyl)(3-tert-butyl-5-methoxy-2-phenoxy)diphenylsilanetitanium(ethylene dioxide), (η5-3-tert-butylcyclopentadienyl)(3-tert-butyl-2-phenoxy)diphenylsilanetitanium(ethylene dioxide), (η5-3-tert-butylcyclopentadienyl)(3-tert-butyl-5-chloro-2-phenoxy)diphenylsilanetitanium (ethylene dioxide), (η5-3-tert-butylcyclopentadienyl) (3-phenyl- 2-phenoxy)diphenylsilanetitanium(ethylene dioxide), (η5-3-tert-butylcyclopentadienyl)(3-tert-butyldimethylsilyl-5-methyl-2-phenoxy) diphenylsilanetitanium(ethylene dioxide), (η5-3-tert-butylcyclopentadienyl)(3-trimethylsilyl-5-methyl-2-phenoxy)diphenylsilanetitanium(ethylene dioxide), (η5-cyclopentadienyl)(2-phenoxy) dimethylsilanetitaniumbis(hexafluoro isopropoxide), (η5-cyclopentadienyl)(3,4-dimethyl-2-phenoxy) dimethylsilanetitaniumbis(hexafluoro isopropoxide), (η5-cyclopentadienyl)(3-tert-butyl-5-methyl-2-phenoxy)dimethylsilanetitaniumbis(hexafluoro isopropoxide), (η5-cyclopentadienyl)(3-tert-butyl-5-methoxy-2-phenoxy)dimethylsilanetitaniumbis (hexafluoro isopropoxide), (η5-cyclopentadienyl)(3-tert-butyl-2-phenoxy)dimethylsilanetitaniumbis (hexafluoro isopropoxide), (η5-cyclopentadienyl)(3-tert-butyl-5-chloro-2-phenoxy) dimethylsilanetitaniumbis(hexafluoro isopropoxide), (η5-cyclopentadienyl)(3-phenyl-2-phenoxy) dimethylsilanetitaniumbis(hexafluoro isopropoxide), (η5-cyclopentadienyl)(3-tert-butyldimethylsilyl-5-methyl-2-phenoxy)dimethylsilanetitaniumbis (hexafluoro isopropoxide), (η5-cyclopentadienyl)(3-trimethylsilyl-5-methyl-2-phenoxy) dimethylsilanetitaniumbis(hexafluoro isopropoxide), (η5-cyclopentadienyl)(2-phenoxy) diphenylsilanetitaniumbis(hexafluoro isopropoxide), (η5-cyclopentadienyl)(3,4-dimethyl-2-phenoxy) diphenylsilanetitaniumbis(hexafluoro isopropoxide), (η5-cyclopentadienyl)(3-tert-butyl-5-methyl-2-phenoxy)diphenylsilanetitaniumbis(hexafluoro isopropoxide), (η5-cyclopentadienyl)(3-tert-butyl-5-methoxy-2-phenoxy)diphenylsilanetitaniumbis (hexafluoro isopropoxide), (η5-cyclopentadienyl)(3-tert-butyl-2-phenoxy)diphenylsilanetitaniumbis (hexafluoro isopropoxide), (η5-cyclopentadienyl)(3-tert-butyl-5-chloro-2-phenoxy) diphenylsilanetitaniumbis(hexafluoro isopropoxide), (η5-cyclopentadienyl)(3-phenyl-2-phenoxy) diphenylsilanetitaniumbis(hexafluoro isopropoxide), (η5-cyclopentadienyl)(3-tert-butyldimethylsilyl-5-methyl-2-phenoxy)diphenylsilanetitaniumbis (hexafluoro isopropoxide), (η5-cyclopentadienyl)(3- trimethylsilyl-5-methyl-2-phenoxy)diphenylsilanetitaniumbis(hexafluoro isopropoxide),
(η5-2,3,4,5-tetramethylcyclopentadienyl)(2-phenoxy)dimethylsilanetitaniumbis(hexafluoro isopropoxide), (η5-2,3,4,5-tetramethylcyclopentadienyl)(3,4-dimethyl-2-phenoxy)dimethylsilanetitaniumbis(hexafluoro isopropoxide), (η5-2,3,4,5-tetramethylcyclopentadienyl)(3-tert-butyl-5-methyl-2-phenoxy)dimethylsilanetitaniumbis(hexafluoro isopropoxide), (η5-2,3,4,5-tetramethylcyclopentadienyl)(3-tert-butyl-5-methoxy-2-phenoxy)dimethylsilanetitaniumbis(hexafluoro isopropoxide), (η5-2,3,4,5-tetramethylcyclopentadienyl)(3-tert-butyl-2-phenoxy)dimethylsilanetitaniumbis(hexafluoro isopropoxide), (η5-2,3,4,5-tetramethylcyclopentadienyl)(3-tert-butyl-5-chloro-2-phenoxy)dimethylsilanetitaniumbis(hexafluoro isopropoxide), (η5-2,3,4,5-tetramethylcyclopentadienyl)(3-phenyl-2-phenoxy)dimethylsilanetitaniumbis(hexafluoro isopropoxide), (η5-2,3,4,5-tetramethylcyclopentadienyl)(3-tert-butyldimethylsilyl-5-methyl-2-phenoxy)dimethylsilanetitaniumbis(hexafluoro isopropoxide), (η5-2,3,4,5-tetramethylcyclopentadienyl)(3-trimethylsilyl-5-methyl-2-phenoxy)dimethylsilanetitaniumbis(hexafluoro isopropoxide), (η5-2,3,4,5-tetramethylcyclopentadienyl)(2-phenoxy)diphenylsilanetitaniumbis(hexafluoro isopropoxide), (η5-2,3,4,5-tetramethylcyclopentadienyl)(3,4-dimethyl-2-phenoxy)diphenylsilanetitaniumbis(hexafluoro isopropoxide), (η5-2,3,4,5-tetramethylcyclopentadienyl)(3-tert-butyl-5-methyl-2-phenoxy)diphenylsilanetitaniumbis(hexafluoro isopropoxide), (η5-2,3,4,5-tetramethylcyclopentadienyl)(3-tert-butyl-5-methoxy-2-phenoxy)diphenylsilanetitaniumbis(hexafluoro isopropoxide), (η5-2,3,4,5-tetramethylcyclopentadienyl)(3-tert-butyl-2-phenoxy)diphenylsilanetitaniumbis(hexafluoro isopropoxide), (η5-2,3,4,5-tetramethylcyclopentadienyl)(3-tert-butyl-5-chloro-2-phenoxy)diphenylsilanetitaniumbis(hexafluoro isopropoxide), (η5-2,3,4,5-tetramethylcyclopentadienyl)(3-phenyl-2-phenoxy)diphenylsilanetitaniumbis(hexafluoro isopropoxide), (η5-2,3,4,5-tetramethylcyclopentadienyl)(3-tert-butyldimethylsilyl-5-methyl-2-phenoxy)diphenylsilanetitaniumbis(hexafluoro isopropoxide), (η5-2,3,4,5-tetramethylcyclopentadienyl)(3-trimethylsilyl-5-methyl-2-phenoxy)diphenylsilanetitaniumbis(hexafluoro isopropoxide), (η5-indenyl)(2-phenoxy)dimethylsilanetitaniumbis(hexafluoro isopropoxide), (η5-indenyl)(3,4-dimethyl-2-phenoxy)dimethylsilanetitaniumbis(hexafluoro isopropoxide), (η5-indenyl)(3-tert-butyl-5-methyl-2-phenoxy)dimethylsilanetitaniumbis(hexafluoro isopropoxide), (η5-indenyl)(3-tert-butyl-5-methoxy-2-phenoxy)dimethylsilanetitaniumbis(hexafluoro isopropoxide), (η5-indenyl)(3-tert-butyl-2-phenoxy)dimethylsilanetitaniumbis(hexafluoro isopropoxide), (η5-indenyl)(3-tert-butyl-5-chloro-2-phenoxy)dimethylsilanetitaniumbis(hexafluoro isopropoxide), (η5-indenyl)(3-phenyl-2-phenoxy)dimethylsilanetitaniumbis(hexafluoro isopropoxide), (η5-indenyl)(3-tert-butyldimethylsilyl-5-methyl-2-phenoxy)dimethylsilanetitaniumbis(hexafluoro isopropoxide), (η5-indenyl)(3-trimethylsilyl-5-methyl-2-phenoxy)dimethylsilanetitaniumbis(hexafluoro isopropoxide), (η5-indenyl)(2-phenoxy)diphenylsilanetitaniumbis(hexafluoro isopropoxide), (η5-indenyl)(3,4-dimethyl-2-phenoxy)diphenylsilanetitaniumbis(hexafluoro isopropoxide), (η5-indenyl)(3-tert-butyl-5-methyl-2-phenoxy)diphenylsilanetitaniumbis(hexafluoro isopropoxide), (η5-indenyl)(3-tert-butyl-5-methoxy-2-phenoxy)diphenylsilanetitaniumbis(hexafluoro isopropoxide), (η5-indenyl)(3-tert-butyl-2-phenoxy)diphenylsilanetitaniumbis(hexafluoro isopropoxide), (η5-indenyl)(3-tert-butyl-5-chloro-2-phenoxy)diphenylsilanetitaniumbis(hexafluoro isopropoxide), (η5-indenyl)(3-phenyl-2-phenoxy)diphenylsilanetitaniumbis(hexafluoro isopropoxide), (η5-indenyl)(3-tert-butyldimethylsilyl-5-methyl-2-phenoxy)diphenylsilanetitaniumbis(hexafluoro isopropoxide), (η5-indenyl)(3-trimethylsilyl-5-methyl-2-phenoxy)diphenylsilanetitaniumbis(hexafluoro isopropoxide), (η5-3-tert-butylcyclopentadienyl)(2-phenoxy)dimethylsilanetitaniumbis(hexafluoro isopropoxide), (η5-3-tert-butylcyclopentadienyl)(3,4-dimethyl-2-phenoxy)dimethylsilanetitaniumbis(hexafluoro isopropoxide), (η5-3-tert-butylcyclopentadienyl)(3-tert-butyl-5-methyl-2-phenoxy)dimethylsilanetitaniumbis(hexafluoro isopropoxide), (η5-3-tert-butylcyclopentadienyl)(3-tert-butyl-5-methoxy-2-phenoxy)dimethylsilanetitaniumbis(hexafluoro isopropoxide), (η5-3-tert-butylcyclopentadienyl)(3-tert-butyl-2-phenoxy)dimethylsilanetitaniumbis(hexafluoro isopropoxide), (η5-3-tert-butylcyclopentadienyl)(3-tert-butyl-5-chloro-2-phenoxy)dimethylsilanetitaniumbis(hexafluoro isopropoxide), (η5-3-tert-butylcyclopentadienyl)(3-phenyl-2-phenoxy)dimethylsilanetitaniumbis(hexafluoro isopropoxide), (η5-3-tert-butylcyclopentadienyl)(3-tert-butyldimethylsilyl-5-methyl-2-phenoxy)dimethylsilanetitaniumbis(hexafluoro isopropoxide), (η5-3-tert-butylcyclopentadienyl)(3-trimethylsilyl-5-methyl-2-phenoxy)dimethylsilanetitaniumbis(hexafluoro isopropoxide), (η5-3-tert-butylcyclopentadienyl)(2-phenoxy)diphenylsilanetitaniumbis(hexafluoro isopropoxide), (η5-3-tert-butylcyclopentadienyl)(3,4-dimethyl-2-phenoxy)diphenylsilanetitaniumbis(hexafluoro isopropoxide), (η5-3-tert-butylcyclopentadienyl)(3-tert-butyl-5-methyl-2-phenoxy)diphenylsilanetitaniumbis(hexafluoro isopropoxide), (η5-3-tert-butylcyclopentadienyl)(3-tert-butyl-5-methoxy-2-phenoxy)diphenylsilanetitaniumbis(hexafluoro isopropoxide), (η5-3-tert-butylcyclopentadienyl)(3-tert-butyl-2-phenoxy)diphenylsilanetitaniumbis(hexafluoro isopropoxide), (η5-3-tert-butylcyclopentadienyl)(3-tert-butyl-5-chloro-2-phenoxy)diphenylsilanetitaniumbis(hexafluoro isopropoxide), (η5-3-tert-butylcyclopentadienyl)(3-phenyl-2-phenoxy)diphenylsilanetitaniumbis(hexafluoro isopropoxide), (η5-3-tert-butylcyclopentadienyl)(3-tert-butyldimethylsilyl-5-methyl-2-phenoxy)diphenylsilanetitaniumbis(hexafluoro isopropoxide), (η5-3-tert-butylcyclopentadienyl)(3-trimethylsilyl-5-methyl-2-phenoxy)diphenylsilanetitaniumbis(hexafluoro isopropoxide), and compounds obtained by substituting (η5-2-methylcyclopentadienyl, η5-3-methylcyclopentadienyl, η5-2-tert-butylcyclopentadienyl, η5-2-n-butylcyclopentadienyl, η5-3-n-butylcyclopentadienyl, 5-fluorenyl for 5-cyclopentadienyl on the above-described compounds, further, compounds obtained by substituting diethoxide, dipropoxide, diisopropoxide, dibutoxide, 1,2-diphenylethylene dioxide, cyclohexane-1,2-dioxide, dibenzyl oxide and the like for dimethoxide on the above-described compounds; and the like.

The alkoxytitanium complex (I) can be produced by a method in which the alkali metal alkoxides (III) are reacted with the halogenated titanium complex (II) (hereinafter, referred to as Method A).

The alkoxytitanium complex (I) can be produced also by a method in which the alcohols (III') are reacted with the halogenated titanium complex (II) (hereinafter, referred to as Method B), and this production is preferably conducted in the presence of an amine compound.

Examples of the aryloxytitanium complex (IV) in which A represents a carbon atom obtained according to the present invention include (η5-cyclopentadienyl) (2-phenoxy) methanetitanium diphenoxide, (η5-cyclopentadienyl)(3,4-dimethyl-2-phenoxy)methanetitanium diphenoxide, (η5-cyclopentadienyl)(3-tert-butyl-5-methyl-2-phenoxy) methanetitanium diphenoxide, (η5-cyclopentadienyl)(3-tert-butyl-5-methoxy-2-phenoxy)methanetitanium diphenoxide, (η5-cyclopentadienyl)(3-tert-butyl-2-phenoxy)methanetitanium diphenoxide, (η5-cyclopentadienyl)(3-tert-butyl-5-chloro-2-phenoxy) methanetitanium diphenoxide, (η5-cyclopentadienyl)(3-phenyl-2-phenoxy)methanetitanium diphenoxide, (η5-cyclopentadienyl)(3-tert-butyldimethylsilyl-5-methyl-2-phenoxy)methanetitanium diphenoxide, (η5-cyclopentadienyl)(3-trimethylsilyl-5-methyl-2-phenoxy)methanetitanium diphenoxide, (η5-cyclopentadienyl)(2-phenoxy) dimethylmethanetitanium diphenoxide, (η5-cyclopentadienyl)(3,4-dimethyl- 2-phenoxy) dimethylmethanetitanium diphenoxide, (η5-cyclopentadienyl)(3-tert-butyl-5-methyl-2-phenoxy) dimethylmethanetitanium diphenoxide, (η5-cyclopentadienyl)(3-tert-butyl-5-methoxy-2-phenoxy) dimethylmethanetitanium diphenoxide, (η5-cyclopentadienyl)(3-tert-butyl-2-phenoxy) dimethylmethanetitanium diphenoxide, (η5-cyclopentadienyl)(3-tert-butyl-5-chloro-2-phenoxy) dimethylmethanetitanium diphenoxide, (η5-cyclopentadienyl)(3-phenyl-2-phenoxy) dimethylmethanetitanium diphenoxide, (η5-cyclopentadienyl)(3-tert-butyldimethylsilyl-5-methyl-2-phenoxy)dimethylmethanetitanium diphenoxide, (η5-cyclopentadienyl)(3-trimethylsilyl-5-methyl-2-phenoxy)dimethylmethanetitanium diphenoxide, (η5-cyclopentadienyl)(2-phenoxy) diphenylmethanetitanium diphenoxide, (η5-cyclopentadienyl)(3,4-dimethyl-2-phenoxy) diphenylmethanetitanium diphenoxide, (η5-cyclopentadienyl)(3-tert-butyl-5-methyl-2-phenoxy) diphenylmethanetitanium diphenoxide, (η5-cyclopentadienyl)(3-tert-butyl-5-methoxy-2-phenoxy) diphenylmethanetitanium diphenoxide, (η5-cyclopentadienyl)(3-tert-butyl-2-phenoxy) diphenylmethanetitanium diphenoxide, (η5-cyclopentadienyl)(3-tert-butyl-5-chloro-2-phenoxy) diphenylmethanetitanium diphenoxide, (η5-cyclopentadienyl)(3-phenyl-2-phenoxy) diphenylmethanetitanium diphenoxide, (η5-cyclopentadienyl)(3-tert-butyldimethylsilyl-5-methyl-2-phenoxy)diphenylmethanetitanium diphenoxide, (η5-cyclopentadienyl)(3-trimethylsilyl-5-methyl-2-phenoxy)diphenylmethanetitanium diphenoxide, (η5-2,3,4,5-tetramethylcyclopentadienyl)(2-phenoxy) methanetitanium diphenoxide, (η5-2,3,4,5-tetramethylcyclopentadienyl)(3,4-dimethyl-2-phenoxy)methanetitanium diphenoxide, (η5-2,3,4,5-tetramethylcyclopentadienyl)(3-tert-butyl-5-methyl-2-phenoxy)methanetitanium diphenoxide, (η5-2,3,4,5-tetramethylcyclopentadienyl)(3-tert-butyl-5-methoxy-2-phenoxy)methanetitanium diphenoxide, (η5-2,3,4,5-tetramethylcyclopentadienyl)(3-tert-butyl-2-phenoxy) methanetitanium diphenoxide, (η5-2,3,4,5-tetramethylcyclopentadienyl)(3-tert-butyl-5-chloro-2-phenoxy)methanetitanium diphenoxide, (η5-2,3,4,5-tetramethylcyclopentadienyl)(3-phenyl-2-phenoxy) methanetitanium diphenoxide, (η5-2,3,4,5-tetramethylcyclopentadienyl)(3-tert-butyldimethylsilyl-5-methyl-2-phenoxy) methanetitanium diphenoxide, (η5-2,3,4,5-tetramethylcyclopentadienyl)(3-trimethylsilyl-5-methyl-2-phenoxy)methanetitanium diphenoxide, (η5-2,3,4,5-tetramethylcyclopentadienyl)(2-phenoxy) dimethylmethanetitanium diphenoxide, (η5-2,3,4,5-tetramethylcyclopentadienyl)(3,4-dimethyl-2-phenoxy)dimethylmethanetitanium diphenoxide, (η5-2,3,4,5-tetramethylcyclopentadienyl)(3-tert-butyl-5-methyl-2-phenoxy)dimethylmethanetitanium diphenoxide, (η5-2,3,4,5-tetramethylcyclopentadienyl) (3-tert-butyl-5-methoxy-2-phenoxy) dimethylmethanetitanium diphenoxide, (η5-2,3,4,5-tetramethylcyclopentadienyl)(3-tert-butyl-2-phenoxy) dimethylmethanetitanium diphenoxide, (η5-2,3,4,5-tetramethylcyclopentadienyl)(3-tert-butyl-5-chloro-2-phenoxy)dimethylmethanetitanium diphenoxide, (η5-2,3,4,5-tetramethylcyclopentadienyl)(3-phenyl-2-phenoxy)dimethylmethanetitanium diphenoxide, (5-2,3,4,5-tetramethylcyclopentadienyl)(3-tert-butyldimethylsilyl-5-methyl-2-phenoxy) dimethylmethanetitanium diphenoxide, (η5-2,3,4,5-tetramethylcyclopentadienyl)(3-trimethylsilyl-5-methyl-2-phenoxy)dimethylmethanetitanium diphenoxide, (η5-2,3,4,5-tetramethylcyclopentadienyl)(2-phenoxy) diphenylmethanetitanium diphenoxide, (η5-2,3,4,5-tetramethylcyclopentadienyl)(3,4-dimethyl-2-phenoxy)diphenylmethanetitanium diphenoxide, (η5-2,3,4,5-tetramethylcyclopentadienyl)(3-tert-butyl-5-methyl-2-phenoxy)diphenylmethanetitanium diphenoxide, (η5-2,3,4,5-tetramethylcyclopentadienyl) (3-tert-butyl-5-methoxy-2-phenoxy) diphenylmethanetitanium diphenoxide, (η5-2,3,4,5-tetramethylcyclopentadienyl)(3-tert-butyl-2-phenoxy) diphenylmethanetitanium diphenoxide, (η5-2,3,4,5-tetramethylcyclopentadienyl)(3-tert-butyl-5-chloro-2-phenoxy)diphenylmethanetitanium diphenoxide, (η5-2,3,4,5-tetramethylcyclopentadienyl)(3-phenyl-2-phenoxy)diphenylmethanetitanium diphenoxide, (η5-2,3,4,5-tetramethylcyclopentadienyl)(3-tert-butyldimethylsilyl-5-methyl-2-phenoxy) diphenylmethanetitanium diphenoxide, (5-2,3,4,5-tetramethylcyclopentadienyl)(3-trimethylsilyl-5-methyl-2-phenoxy)diphenylmethanetitanium diphenoxide, (η5-3-methylcyclopentadienyl)(2-phenoxy) methanetitanium diphenoxide, (η5-3-methylcyclopentadienyl)(3,4-dimethyl-2-phenoxy)

methanetitanium diphenoxide, (η5-3-methylcyclopentadienyl)(3-tert-butyl-5-methyl-2-phenoxy)methanetitanium diphenoxide, (η5-3-methylcyclopentadienyl)(3-tert-butyl-5-methoxy-2-phenoxy)methanetitanium diphenoxide, (η5-3-methylcyclopentadienyl)(3-tert-butyl-2-phenoxy)methanetitanium diphenoxide, (η5-3-methylcyclopentadienyl)(3-tert-butyl-5-chloro-2-phenoxy)methanetitanium diphenoxide, (η5-3-methylcyclopentadienyl)(3-phenyl-2-phenoxy)methanetitanium diphenoxide, (η5-3-methylcyclopentadienyl)(3-tert-butyldimethylsilyl-5-methyl-2-phenoxy)methanetitanium diphenoxide, (η5-3-methylcyclopentadienyl)(3-trimethylsilyl-5-methyl-2-phenoxy)methanetitanium diphenoxide, (η5-3-methylcyclopentadienyl)(2-phenoxy)dimethylmethanetitanium diphenoxide, (η5-3-methylcyclopentadienyl)(3,4-dimethyl-2-phenoxy)dimethylmethanetitanium diphenoxide, (η5-3-methylcyclopentadienyl)(3-tert-butyl-5-methyl-2-phenoxy)dimethylmethanetitanium diphenoxide, (η5-3-methylcyclopentadienyl)(3-tert-butyl-5-methoxy-2-phenoxy)dimethylmethanetitanium diphenoxide, (η5-3-methylcyclopentadienyl)(3-tert-butyl-2-phenoxy)dimethylmethanetitanium diphenoxide, (η5-3-methylcyclopentadienyl)(3-tert-butyl-5-chloro-2-phenoxy)dimethylmethanetitanium diphenoxide, (η5-3-methylcyclopentadienyl)(3-phenyl-2-phenoxy)dimethylmethanetitanium diphenoxide, (η5-3-methylcyclopentadienyl)(3-tert-butyldimethylsilyl-5-methyl-2-phenoxy)dimethylmethanetitanium diphenoxide, (η5-3-methylcyclopentadienyl)(3-trimethylsilyl-5-methyl-2-phenoxy)dimethylmethanetitanium diphenoxide, (η5-3-methylcyclopentadienyl)(2-phenoxy)diphenylmathanetitanium diphenoxide, (η5-3-methylcyclopentadienyl)(3,4-dimethyl-2-phenoxy)diphenylmathanetitanium diphenoxide, (η5-3-methylcyclopentadienyl)(3-tert-butyl-5-methyl-2-phenoxy)diphenylmathanetitanium diphenoxide, (η5-3-methylcyclopentadienyl)(3-tert-butyl-5-methoxy-2-phenoxy)diphenylmathanetitanium diphenoxide, (η5-3-methylcyclopentadienyl)(3-tert-butyl-2-phenoxy)diphenylmathanetitanium diphenoxide, (η5-3-methylcyclopentadienyl)(3-tert-butyl-5-chloro-2-phenoxy)diphenylmathanetitanium diphenoxide, (η5-3-methylcyclopentadienyl)(3-phenyl-2-phenoxy)diphenylmathanetitanium diphenoxide, (η5-3-methylcyclopentadienyl)(3-tert-butyldimethylsilyl-5-methyl-2-phenoxy)diphenylmathanetitanium diphenoxide, (η5-3-methylcyclopentadienyl)(3-trimethylsilyl-5-methyl-2-phenoxy)diphenylmathanetitanium diphenoxide, (η5-3-tert-butylcyclopentadienyl)(2-phenoxy)methanetitanium diphenoxide, (η5-3-tert-butylcyclopentadienyl)(3,4-dimethyl-2-phenoxy)methanetitanium diphenoxide, (η5-3-tert-butylcyclopentadienyl)(3-tert-butyl-5-methyl-2-phenoxy)methanetitanium diphenoxide, (η5-3-tert-butylcyclopentadienyl)(3-tert-butyl-5-methoxy-2-phenoxy)methanetitanium diphenoxide, (η5-3-tert-butylcyclopentadienyl)(3-tert-butyl-2-phenoxy)methanetitanium diphenoxide, (η5-3-tert-butylcyclopentadienyl)(3-tert-butyl-5-chloro-2-phenoxy)methanetitanium diphenoxide, (η5-3-tert-butylcyclopentadienyl)(3-phenyl-2-phenoxy)methanetitanium diphenoxide, (η5-3-tert-butylcyclopentadienyl)(3-tert-butyldimethylsilyl-5-methyl-2-phenoxy)methanetitanium diphenoxide, (η5-3-tert-butylcyclopentadienyl)(3-trimethylsilyl-5-methyl-2-phenoxy)methanetitanium diphenoxide, (η5-3-tert-butylcyclopentadienyl)(2-phenoxy)dimethylmethanetitanium diphenoxide, (η5-3-tert-butylcyclopentadienyl)(3,4-dimethyl-2-phenoxy)dimethylmethanetitanium diphenoxide, (η5-3-tert-butylcyclopentadienyl)(3-tert-butyl-5-methyl-2-phenoxy)dimethylmethanetitanium diphenoxide, (η5-3-tert-butylcyclopentadienyl)(3-tert-butyl-5-methoxy-2-phenoxy)dimethylmethanetitanium diphenoxide, (η5-3-tert-butylcyclopentadienyl)(3-tert-butyl-2-phenoxy)dimethylmethanetitanium diphenoxide, (η5-3-tert-butylcyclopentadienyl)(3-tert-butyl-5-chloro-2-phenoxy)dimethylmethanetitanium diphenoxide, (η5-3-tert-butylcyclopentadienyl)(3-phenyl-2-phenoxy)dimethylmethanetitanium diphenoxide, (η5- 3-tert-butylcyclopentadienyl)(3-tert-butyldimethylsilyl-5-methyl-2-phenoxy)dimethylmethanetitanium diphenoxide, (η5-3-tert-butylcyclopentadienyl)(3-trimethylsilyl-5-methyl-2-phenoxy)dimethylmethanetitanium diphenoxide, (η5-3-tert-butylcyclopentadienyl)(2-phenoxy)diphenylmethanetitanium diphenoxide, (η5-3-tert-butylcyclopentadienyl)(3,4-dimethyl-2-phenoxy)diphenylmethanetitanium diphenoxide, (η5-3-tert-butylcyclopentadienyl)(3-tert-butyl-5-methyl-2-phenoxy)diphenylmethanetitanium diphenoxide, (η5-3-tert-butylcyclopentadienyl)(3-tert-butyl-5-methoxy-2-phenoxy)diphenylmethanetitanium diphenoxide, (η5-3-tert-butylcyclopentadienyl)(3-tert-butyl-2-phenoxy)diphenylmethanetitanium diphenoxide, (η5-3-tert-butylcyclopentadienyl)(3-tert-butyl-5-chloro-2-phenoxy)diphenylmethanetitanium diphenoxide, (η5-3-tert-butylcyclopentadienyl)(3-phenyl-2-phenoxy)diphenylmethanetitanium diphenoxide, (η5-3-tert-butylcyclopentadienyl)(3-tert-butyldimethylsilyl-5-methyl-2-phenoxy)diphenylmethanetitanium diphenoxide, (η5-3-tert-butylcyclopentadienyl)(3-trimethylsilyl-5-methyl-2-phenoxy)diphenylmethanetitanium diphenoxide, (η5-cyclopentadienyl)(2-phenoxy)methanetitanium(1,1'-binaphthyl-2,2'-dioxide), (η5-cyclopentadienyl)(3,4-dimethyl- 2-phenoxy)methanetitanium(1,1'-binaphthyl-2,2'-dioxide), (η5-cyclopentadienyl)(3-tert-butyl-5-methyl-2-phenoxy)methanetitanium(1,1'-binaphthyl-2,2'-dioxide), (η5-cyclopentadienyl)(3-tert-butyl-5-methoxy-2-phenoxy)methanetitanium(1,1'-binaphthyl-2,2'-dioxide), (η5-cyclopentadienyl)(3-tert-butyl-2-phenoxy)methanetitanium(1,1'-binaphthyl-2,2'-dioxide), (η5-cyclopentadienyl)(3-tert-butyl-5-chloro-2-phenoxy)methanetitanium(1,1'-binaphthyl-2,2'-dioxide), (η5-cyclopentadienyl)(3-phenyl-2-phenoxy)methanetitanium(1,1'-binaphthyl-2,2'-dioxide), (η5-cyclopentadienyl)(3-tert-butyldimethylsilyl-5-methyl-2-phenoxy)methanetitanium(1,1'-binaphthyl-2,2'-dioxide), (η5-cyclopentadienyl)(3-trimethylsilyl-5-methyl-2-phenoxy)methanetitanium(1,1'-binaphthyl-2,2'-dioxide), (η5-cyclopentadienyl)(2-phenoxy)dimethylmethanetitanium(1,1'-binaphthyl-2,2'-dioxide), (η5-cyclopentadienyl)(3,4-dimethyl-2-phenoxy)dimethylmethanetitanium(1,1'-binaphthyl-2,2'-dioxide), (η5-cyclopentadienyl)(3-tert-butyl-5-methyl-2-phenoxy)dimethylmethanetitanium(1,1'- binaphthyl-2,2'-dioxide), (η5-cyclopentadienyl)(3-tert-butyl-5-methoxy-2-phenoxy)dimethylmethanetitanium(1,1'-binaphthyl-2,2'-dioxide), (η5-cyclopentadienyl)(3-tert-butyl-2-phenoxy)dimethylmethanetitanium(1,1'-binaphthyl-2,2'-dioxide), (η5-cyclopentadienyl)(3-tert-butyl-5-chloro-2-phenoxy)dimethylmethanetitanium(1,1'-binaphthyl-2,2'-dioxide), (η5-cyclopentadienyl)(3-phenyl-2-phenoxy)dimethylmethanetitanium(1,1'-binaphthyl-2,2'-dioxide), (η5-cyclopentadienyl)(3-tert-butyldimethylsilyl-5-methyl-2-phenoxy)dimethylmethanetitanium(1,1'-binaphthyl-2,2'-dioxide), (η5-cyclopentadienyl)(3-trimethylsilyl-5-methyl-2-phenoxy)dimethylmethanetitanium(1,1'-binaphthyl-2,2'-dioxide), (η5-cyclopentadienyl)(2-phenoxy)diphenylmethanetitanium(1,1'-binaphthyl-2,2'-dioxide), (η5-cyclopentadienyl)(3,4-dimethyl-2-phenoxy)diphenylmethanetitanium(1,1'-binaphthyl-2,2'-dioxide), (η5-cyclopentadienyl)(3-tert-butyl-5-methyl-2-phenoxy)diphenylmethanetitanium(1,1'-binaphthyl-2,2'-dioxide), (η5-cyclopentadienyl)(3-tert-butyl-5-methoxy-2-phenoxy)diphenylmethanetitanium(1,1'-binaphthyl-2,2'-dioxide), (η5-cyclopentadienyl)(3-tert-butyl-2-phenoxy)diphenylmethanetitanium(1,1'-binaphthyl-2,2'-dioxide), (η5-cyclopentadienyl)(3-tert-butyl-5-chloro-2-phenoxy)diphenylmethanetitanium(1,1'-binaphthyl-2,2'-dioxide), (η5-cyclopentadienyl)(3-phenyl-2-phenoxy)diphenylmethanetitanium(1,1'-binaphthyl-2,2'-dioxide), (η5-cyclopentadienyl)(3-tert-butyldimethylsilyl-5-methyl-2-phenoxy)diphenylmethanetitanium(1,1'-binaphthyl-2,2'-dioxide), (η5-cyclopentadienyl)(3-trimethylsilyl-5-methyl-2-phenoxy)diphenylmethanetitanium(1,1'-binaphthyl-2,2'-dioxide), (η5-2,3,4,5-tetramethylcyclopentadienyl)(2-phenoxy)methanetitanium(1,1'-binaphthyl-2,2'-dioxide), (η5-2,3,4,5-tetramethylcyclopentadienyl)(3,4-dimethyl-2-phenoxy)methanetitanium(1,1'-binaphthyl-2,2'-dioxide), (η5-2,3,4,5-tetramethylcyclopentadienyl)(3-tert-butyl-5-methyl-2-phenoxy)methanetitanium(1,1'-binaphthyl-2,2'-dioxide), (η5-2,3,4,5-tetramethylcyclopentadienyl)(3-tert-butyl-5-methoxy-2-phenoxy)methanetitanium(1,1'-binaphthyl-2,2'-dioxide), (η5-2,3,4,5-tetramethylcyclopentadienyl)(3-tert-butyl-2-phenoxy)methanetitanium(1,1'-binaphthyl-2,2'-dioxide), (η5-2,3,4,5-tetramethylcyclopentadienyl)(3-tert-butyl-5-chloro-2-phenoxy)methanetitanium(1,1'-binaphthyl-2,2'-dioxide), (η5-2,3,4,5-tetramethylcyclopentadienyl)(3-phenyl-2-phenoxy)methanetitanium(1,1'-binaphthyl-2,2'-dioxide), (η5-2,3,4,5-tetramethylcyclopentadienyl)(3-tert-butyldimethylsilyl-5-methyl-2-phenoxy)methanetitanium(1,1'-binaphthyl-2,2'-dioxide), (η5-2,3,4,5-tetramethylcyclopentadienyl)( 3-trimethylsilyl-5-methyl-2-phenoxy)methanetitanium(1,1'-binaphthyl-2,2'-dioxide), (η5-2,3,4,5-tetramethylcyclopentadienyl)(2-phenoxy)dimethylmethanetitanium(1,1'-binaphthyl-2,2'-dioxide), (η5-2,3,4,5-tetramethylcyclopentadienyl)(3,4-dimethyl-2-phenoxy)dimethylmethanetitanium(1,1'-binaphthyl-2,2'-dioxide), (η5-2,3,4,5-tetramethylcyclopentadienyl)(3-tert-butyl-5-methyl-2-phenoxy)dimethylmethanetitanium(1,1'-binaphthyl-2,2'-dioxide), (η5-2,3,4,5-tetramethylcyclopentadienyl)(3-tert-butyl-5-methoxy-2-phenoxy)dimethylmethanetitanium(1,1'-binaphthyl-2,2'-dioxide), (η5-2,3,4,5-tetramethylcyclopentadienyl)(3-tert-butyl-2-phenoxy)dimethylmethanetitanium(1,1'-binaphthyl-2,2'-dioxide), (η5-2,3,4,5-tetraethylcyclopentadienyl)(3-tert-butyl-5-chloro-2-phenoxy)dimethylmethanetitanium(1,1'-binaphthyl-2,2'-dioxide), (η5-2,3,4,5-tetramethylcyclopentadienyl)(3-phenyl-2-phenoxy) dimethylmethanetitanium(1,1'-binaphthyl-2,2'-dioxide), (η5-2,3,4,5-tetramethylcyclopentadienyl)(3-tert-butyldimethylsilyl-5-methyl-2-phenoxy)dimethylmethanetitanium(1,1'-binaphthyl-2,2'-dioxide), (η5-2,3,4,5-tetramethylcyclopentadienyl)(3-trimethylsilyl-5-methyl-2-phenoxy)dimethylmethanetitanium(1,1'-binaphthyl- 2,2'-dioxide), (η5-2,3,4,5-tetramethylcyclopentadienyl)(2-phenoxy)diphenylmethanetitanium(1,1'-binaphthyl-2,2'-dioxide), (η5-2,3,4,5-tetramethylcyclopentadienyl)(3,4-dimethyl-2-phenoxy)diphenylmethanetitanium(1,1'-binaphthyl-2,2'-dioxide), (η5-2,3,4,5-tetramethylcyclopentadienyl)(3-tert-butyl-5-methyl-2-phenoxy)diphenylmethanetitanium(1,1'-binaphthyl-2,2'-dioxide), (η5-2,3,4,5-tetramethylcyclopentadienyl)(3-tert-butyl-5-methoxy-2-phenoxy)diphenylmethanetitanium(1,1'-binaphthyl-2,2'-dioxide), (η5-2,3,4,5-tetramethylcyclopentadienyl)(3-tert-butyl-2-phenoxy)diphenylmethanetitanium(1,1'-binaphthyl-2,2'-dioxide), (η5-2,3,4,5-tetramethylcyclopentadienyl)(3-tert-butyl-5-chloro-2-phenoxy)diphenylmethanetitanium(1,1'-binaphthyl-2,2'-dioxide), (η5-2,3,4,5-tetramethylcyclopentadienyl)(3-phenyl-2-phenoxy)diphenylmethanetitanium(1,1'-binaphthyl-2,2'-dioxide), (η5-2,3,4,5-tetramethylcyclopentadienyl)(3-tert-butyldimethylsilyl-5-methyl-2-phenoxy)diphenylmethanetitanium(1,1'-binaphthyl-2,2'-dioxide), (η5-2,3,4,5-tetramethylcyclopentadienyl)(3-trimethylsilyl-5-methyl-2-phenoxy)diphenylmethanetitanium(1,1'-binaphthyl-2,2'-dioxide), (η5-3-methylcyclopentadienyl)(2-phenoxy)methanetitanium(1,1'-binaphthyl-2,2'-dioxide), (η5-3-methylcyclopentadienyl)(3,4-dimethyl-2-phenoxy)methanetitanium(1,1'-binaphthyl-2,2'-dioxide), (η5-3-methylcyclopentadienyl)(3-tert-butyl-5-methyl-2-phenoxy)methanetitanium(1,1'-binaphthyl-2,2'-dioxide), (η5-3-methylcyclopentadienyl)(3-tert-butyl-5-methoxy-2-phenoxy)methanetitanium(1,1'-binaphthyl-2,2'-dioxide), (η5-3-methylcyclopentadienyl)(3-tert-butyl-2-phenoxy)methanetitanium(1,1'-binaphthyl-2,2'-dioxide), (η5-3-methylcyclopentadienyl)(3-tert-butyl-5-chloro-2-phenoxy)methanetitanium(1,1'-binaphthyl-2,2'-dioxide), (η5-3-methylcyclopentadienyl)(3-phenyl-2-phenoxy)methanetitanium(1,1'-binaphthyl-2,2'-dioxide), (η5-3-methylcyclopentadienyl)(3-tert-butyldimethylsilyl-5-methyl-2-phenoxy)methanetitanium(1,1'-binaphthyl-2,2'-dioxide), (η5-3-methylcyclopentadienyl)(3-trimethylsilyl-5-methyl-2-phenoxy)methanetitanium(1,1'-binaphthyl-2,2'-dioxide), (η5-3-methylcyclopentadienyl)(2-phenoxy)dimethylmethanetitanium(1,1'-binaphthyl-2,2'-dioxide), (η5-3-methylcyclopentadienyl)(3,4-dimethyl-2-phenoxy)dimethylmethanetitanium(1,1'-binaphthyl-2,2'-dioxide), (η5-3- rnethylcyclopentadienyl)(3-tert-butyl- 5-methyl-2-phenoxy)dimethylmethanetitanium(1,1'-binaphthyl-2,2'-dioxide), (η5-3-methylcyclopentadienyl)(3-tert-butyl-5-methoxy-2-phenoxy)dimethylmethanetitanium (1,1'-binaphthyl-2,2'-dioxide), (η5-3-methylcyclopentadienyl)(3-tert-butyl-2-phenoxy) dimethylmethanetitanium(1,1'-binaphthyl-2,2'-dioxide), (η5-3-methylcyclopentadienyl)(3-tert-butyl-5-chloro-2-phenoxy)dimethylmethanetitanium(1,1'-binaphthyl-2,2'-dioxide), (η5-3-methylcyclopentadienyl)(3-phenyl-2-phenoxy) dimethylmethanetitanium(1,1'-binaphthyl-2,2'-dioxide), (η5-3-methylcyclopentadienyl)(3-tert-butyldimethylsilyl-5-methyl-2-phenoxy) dimethylmethanetitanium(1,1'-binaphthyl-2,2'-dioxide), (η5-3-methylcyclopentadienyl)(3-trimethylsilyl-5-methyl-2-phenoxy) dimethylmethanetitanium(1,1'-binaphthyl-2,2'-dioxide), (η5-3-methylcyclopentadienyl)(2-phenoxy) diphenylmethanetitanium(1,1'-binaphthyl-2,2'-dioxide), (η5-3-methylcyclopentadienyl)(3,4-dimethyl-2-phenoxy)diphenylmethanetitanium(1,1'-binaphthyl-2,2'-dioxide), (η5-3-methylcyclopentadienyl)(3-tert-butyl-5-methyl-2-phenoxy)diphenylmethanetitanium(1,1'-binaphthyl-2,2'-dioxide), (η5-3-methylcyclopentadienyl)(3-tert-butyl-5-methoxy-2-phenoxy) diphenylmethanetitanium(1,1'-binaphthyl-2,2'-dioxide), (η5-3-methylcyclopentadienyl)(3-tert-butyl-2-phenoxy)diphenylmethanetitanium(1,1'-binaphthyl-2,2'-dioxide), (η5-3-methylcyclopentadienyl)(3-tert-butyl-5-chloro-2-phenoxy)diphenylmethanetitanium (1,1'-binaphthyl-2,2'-dioxide), (η5-3-methylcyclopentadienyl)(3-phenyl-2-phenoxy) diphenylmethanetitanium(1,1'-binaphthyl-2,2'-dioxide), (η5-3-methylcyclopentadienyl)(3-tert-butyldimethylsilyl-5-methyl-2-phenoxy) diphenylmethanetitanium(1,1'-binaphthyl-2,2'-dioxide), (η5-3-methylcyclopentadienyl)(3-trimethylsilyl-5-methyl-2-phenoxy) diphenylmethanetitanium(1,1'-binaphthyl-2,2'-dioxide), (η5-3-tert-butylcyclopentadienyl)(2-phenoxy) methanetitanium(1,1'-binaphthyl-2,2'-dioxide), (η5-3-tert-butylcyclopentadienyl)(3,4-dimethyl-2-phenoxy) methanetitanium(1,1'-binaphthyl-2,2'-dioxide), (η5-3-tert-butylcyclopentadienyl)(3-tert-butyl-5-methyl-2-phenoxy)methanetitanium(1,1'-binaphthyl-2,2'-dioxide), (η5-3-tert-butylcyclopentadienyl)(3-tert-butyl-5-methoxy-2-phenoxy)methanetitanium(1,1'-binaphthyl-2,2'-dioxide), (η5-3-tert-butylcyclopentadienyl)(3-tert-butyl-2-phenoxy) methanetitanium(1,1'-binaphthyl-2,2'-dioxide), (η5-3-tert-butylcyclopentadienyl)(3-tert-butyl-5-chloro-2-phenoxy)methanetitanium(1,1'-binaphthyl-2,2-dioxide), (η5-3-tert-butylcyclopentadienyl)(3-phenyl-2-phenoxy)methanetitanium(1,1'-binaphthyl-2,2'-dioxide), (η5-3-tert-butylcyclopentadienyl)(3-tert-butyldimethylsilyl-5-methyl-2-phenoxy) methanetitanium(1,1'-binaphthyl-2,2'-dioxide), (η5-3-tert-butylcyclopentadienyl)(3-trimethylsilyl-5-methyl-2-phenoxy)methanetitanium(1,1'-binaphthyl-2,2'-dioxide), (η5-3-tert-butylcyclopentadienyl)(2-phenoxy) dimethylmethanetitanium(1,1'-binaphthyl-2,2'-dioxide), (η5-3-tert-butylcyclopentadienyl)(3,4-dimethyl-2-phenoxy)dimethylmethanetitanium(1,1'-binaphthyl-2,2'-dioxide), (η5-3-tert-butylcyclopentadienyl)(3-tert-butyl-5-methyl-2-phenoxy)dimethylmethanetitanium(1,1'-binaphthyl-2,2'-dioxide), (η5-3-tert-butylcyclopentadienyl)(3-tert-butyl-5-methoxy-2-phenoxy)dimethylmethanetitanium (1,1'-binaphthyl-2,2'-dioxide), (η5-3-tert-butylcyclopentadienyl)(3-tert-butyl-2-phenoxy) dimethylmethanetitanium(1,1'-binaphthyl-2,2'-dioxide), (η5-3-tert-butylcyclopentadienyl)(3-tert-butyl-5-chloro-2-phenoxy)dimethylmethanetitanium(1,1'-binaphthyl-2,2'-dioxide), (η5-3-tert-butylcyclopentadienyl)(3-phenyl-2-phenoxy) dimethylmethanetitanium(1,1'-binaphthyl-2,2'-dioxide), (η5-3-tert-butylcyclopentadienyl)(3-tert-butyldimethylsilyl-5-methyl-2-phenoxy) dimethylmethanetitanium(1,1'-binaphthyl-2,2'-dioxide), (η5-3-tert-butylcyclopentadienyl)(3-trimethylsilyl-5-methyl-2-phenoxy) dimethylmethanetitanium(1,1'-binaphthyl-2,2'-dioxide), (η5-3-tert-butylcyclopentadienyl)(2-phenoxy) diphenylmethanetitanium(1,1'-binaphthyl-2,2'-dioxide), (η5-3-tert-butylcyclopentadienyl)(3,4-dimethyl-2-phenoxy)diphenylmethanetitanium(1,1'-binaphthyl-2,2'-dioxide), (η5-3-tert-butylcyclopentadienyl)(3-tert-butyl-5-methyl-2-phenoxy)diphenylmethanetitanium(1,1'-binaphthyl-2,2'-dioxide), (η5-3-tert-butylcyclopentadienyl)(3-tert-butyl-5-methoxy-2-phenoxy)diphenylmethanetitanium (1,1'-binaphthyl-2,2'-dioxide), (η5-3-tert-butylcyclopentadienyl)(3-tert-butyl-2-phenoxy) diphenylmethanetitanium(1,1'-binaphthyl-2,2'-dioxide), (η5-3-tert-butylcyclopentadienyl)(3-tert-butyl-5-chloro-2-phenoxy)diphenylmethanetitanium (1,1'-binaphthyl-2,2'-dioxide), (η5-3-tert-butylcyclopentadienyl)(3-phenyl- 2-phenoxy) diphenylmethanetitanium(1,1'-binaphthyl-2,2'-dioxide), (η5-3-tert-butylcyclopentadienyl)(3-tert-butyldimethylsilyl-5-methyl-2-phenoxy) diphenylmethanetitanium(1,1'-binaphthyl-2,2'-dioxide), (η5-3-tert-butylcyclopentadienyl)(3-trimethylsilyl-5-methyl-2-phenoxy) diphenylmethanetitanium(1,1'-binaphthyl-2,2'-dioxide), and compounds obtained by substituting η5-2-methylcyclopentadienyl, η5-2-tert-butylcyclopentadienyl, η5-2-n-butylcyclopentadienyl, η5-3-n-butylcyclopentadienyl, η5-indenyl, η5-fluorenyl for η5-cyclopentadienyl on the above-described compounds, further, compounds obtained by substituting di-4-methylphenoxide, bis(2,4,6-trimethylphenoxide), bis (pentafluorophenoxide) and the like for diphenoxide on the above-described compounds; and the like.

Examples of the aryloxytitanium complex (IV) in which A represents a silicon atom obtained according to the present invention include (η5-cyclopentadienyl)(2-phenoxy) dimethylsilanetitanium diphenoxide, (η5-cyclopentadienyl) (3,4-dimethyl-2-phenoxy)dimethylsilanetitanium diphenoxide, (η5-cyclopentadienyl)(3-tert-butyl-5-methyl-2-phenoxy)dimethylsilanetitanium diphenoxide, (η5-cyclopentadienyl)(3-tert-butyl-5-methoxy-2-phenoxy) dimethylsilanetitanium diphenoxide, (η5-cyclopentadienyl) (3-tert-butyl-2-phenoxy)dimethylsilanetitanium diphenoxide, (η5-cyclopentadienyl)(3-tert-butyl-5-chloro-2-phenoxy)dimethylsilanetitanium diphenoxide, (η5-cyclopentadienyl)(3-phenyl-2-phenoxy)

dimethylsilanetitanium diphenoxide, (η5-cyclopentadienyl)(3-tert-butyldimethylsilyl-5-methyl-2-phenoxy) dimethylsilanetitanium diphenoxide, (η5-cyclopentadienyl)(3-trimethylsilyl-5-methyl-2-phenoxy) dimethylsilanetitanium diphenoxide, (η5-cyclopentadienyl)(2-phenoxy) diphenylsilanetitanium diphenoxide, (η5-cyclopentadienyl)(3,4-dimethyl-2-phenoxy) diphenylsilanetitanium diphenoxide, (η5-cyclopentadienyl)(3-tert-butyl-5-methyl-2-phenoxy) diphenylsilanetitanium diphenoxide, (η5-cyclopentadienyl)(3-tert-butyl-5-methoxy-2-phenoxy) diphenylsilanetitanium diphenoxide, (η5-cyclopentadienyl)(3-tert-butyl-2-phenoxy) diphenylsilanetitanium diphenoxide, (η5-cyclopentadienyl)(3-tert-butyl-5-chloro-2-phenoxy) diphenylsilanetitanium diphenoxide, (η5-cyclopentadienyl)(3-phenyl-2-phenoxy) diphenylsilanetitanium diphenoxide, (η5-cyclopentadienyl)(3-tert-butyldimethylsilyl-5-methyl-2-phenoxy)diphenylsilanetitanium diphenoxide, (η5-cyclopentadienyl)(3-trimethylsilyl-5-methyl-2-phenoxy)diphenylsilanetitanium diphenoxide, (η5-2,3,4,5-tetramethylcyclopentadienyl)(2-phenoxy) dimethylsilanetitanium diphenoxide, (η5-2,3,4,5-tetramethylcyclopentadienyl)(3,4-dimethyl-2-phenoxy)dimethylsilanetitanium diphenoxide, (η5-2,3,4,5-tetramethylcyclopentadienyl)(3-tert-butyl-5-methyl-2-phenoxy)dimethylsilanetitanium diphenoxide, (η5-2,3,4,5-tetramethylcyclopentadienyl)(3-tert-butyl-5-methoxy-2-phenoxy) dimethylsilanetitanium diphenoxide, (η5-2,3,4,5-tetramethylcyclopentadienyl)(3-tert-butyl-2-phenoxy) dimethylsilanetitanium diphenoxide, (η5-2,3,4,5-tetramethylcyclopentadienyl)(3-tert-butyl-5-chloro-2-phenoxy)dimethylsilanetitanium diphenoxide, (η5-2,3,4,5-tetramethylcyclopentadienyl)(3-phenyl-2-phenoxy)dimethylsilanetitanium diphenoxide, (η5-2,3,4,5-tetramethylcyclopentadienyl)(3-tert-butyldimethylsilyl-5-methyl-2-phenoxy) dimethylsilanetitanium diphenoxide, (η5-2,3,4,5-tetramethylcyclopentadienyl)(3-trimethylsilyl-5-methyl-2-phenoxy)dimethylsilanetitanium diphenoxide, (η5-2,3,4,5-tetramethylcyclopentadienyl)(2-phenoxy) diphenylsilanetitanium diphenoxide, (η5-2,3,4,5-tetramethylcyclopentadienyl)(3,4-dimethyl-2-phenoxy)diphenylsilanetitanium diphenoxide, (η5-2,3,4,5-tetramethylcyclopentadienyl)(3-tert-butyl-5-methyl-2-phenoxy)diphenylsilanetitanium diphenoxide, (η5-2,3,4,5-tetramethylcyclopentadienyl)(3-tert-butyl-5-methoxy-2-phenoxy) diphenylsilanetitanium diphenoxide, (η5-2,3,4,5-tetramethylcyclopentadienyl)(3-tert-butyl-2-phenoxy) diphenylsilanetitanium diphenoxide, (η5-2,3,4,5-tetramethylcyclopentadienyl)(3-tert-butyl-5-chloro-2-phenoxy)diphenylsilanetitanium diphenoxide, (η5-2,3,4,5-tetramethylcyclopentadienyl)(3-phenyl-2-phenoxy)diphenylsilanetitanium diphenoxide, (η5-2,3,4,5-tetramethylcyclopentadienyl)(3-tert-butyldimethylsilyl-5-methyl-2-phenoxy) diphenylsilanetitanium diphenoxide, (η5-2,3,4,5-tetramethylcyclopentadienyl)(3-trimethylsilyl-5-methyl-2-phenoxy)diphenylsilanetitanium diphenoxide, (η5-indenyl)(2-phenoxy)dimethylsilanetitanium diphenoxide, (η5-indenyl)(3,4-dimethyl-2-phenoxy) dimethylsilanetitanium diphenoxide, (η5-indenyl)(3-tert-butyl-5-methyl-2-phenoxy)dimethylsilanetitanium diphenoxide, (η5-indenyl)(3-tert-butyl-5-methoxy-2-phenoxy)dimethylsilanetitanium diphenoxide, (η5-indenyl)(3-tert-butyl-2-phenoxy) dimethylsilanetitanium diphenoxide, (η5-indenyl)(3-tert-butyl-5-chloro-2-phenoxy)dimethylsilanetitanium diphenoxide, (η5-indenyl)(3-phenyl-2-phenoxy) dimethylsilanetitanium diphenoxide, (η5-indenyl)(3-tert-butyldimethylsilyl-5-methyl-2-phenoxy) dimethylsilanetitanium diphenoxide, (η5-indenyl)(3-trimethylsilyl-5-methyl-2-phenoxy) dimethylsilanetitanium diphenoxide, (η5-indenyl)(2-phenoxy)diphenylsilanetitanium diphenoxide, (η5-indenyl)(3,4-dimethyl-2-phenoxy) diphenylsilanetitanium diphenoxide, (η5-indenyl)(3-tert-butyl-5-methyl-2-phenoxy)diphenylsilanetitanium diphenoxide, (η5-indenyl)(3-tert-butyl-5-methoxy-2-phenoxy)diphenylsilanetitanium diphenoxide, (η5-indenyl)(3-tert-butyl-2-phenoxy) diphenylsilanetitanium diphenoxide, (η5-indenyl)(3-tert-butyl-5-chloro-2-phenoxy)diphenylsilanetitanium diphenoxide, (η5-indenyl)(3-phenyl-2-phenoxy) diphenylsilanetitanium diphenoxide, (η5-indenyl)(3-tert-butyldimethylsilyl-5-methyl-2-phenoxy) diphenylsilanetitanium diphenoxide, (η5-indenyl)(3-trimethylsilyl-5-methyl-2-phenoxy) diphenylsilanetitanium diphenoxide, (η5-3-tert-butylcyclopentadienyl)(2-phenoxy) dimethylsilanetitanium diphenoxide, (η5-3-tert-butylcyclopentadienyl)(3,4-dimethyl-2-phenoxy) dimethylsilanetitanium diphenoxide, (η5-3-tert-butylcyclopentadienyl)(3-tert-butyl-5-methyl-2-phenoxy)dimethylsilanetitanium diphenoxide, (η5-3-tert-butylcyclopentadienyl)(3-tert-butyl-5-methoxy-2-phenoxy)dimethylsilanetitanium diphenoxide, (η5-3-tert-butylcyclopentadienyl)(3-tert-butyl-2-phenoxy) dimethylsilanetitanium diphenoxide, (η5-3-tert-butylcyclopentadienyl)(3-tert-butyl-5-chloro-2-phenoxy)dimethylsilanetitanium diphenoxide, (η5-3-tert-butylcyclopentadienyl)(3-phenyl-2-phenoxy) dimethylsilanetitanium diphenoxide, (η5-3-tert-butylcyclopentadienyl)(3-tert-butyldimethylsilyl-5-methyl-2-phenoxy)dimethylsilanetitanium diphenoxide, (η5-3-tert-butylcyclopentadienyl)(3-trimethylsilyl-5-methyl-2-phenoxy) dimethylsilanetitanium diphenoxide, (η5-3-tert-butylcyclopentadienyl)(2-phenoxy) diphenylsilanetitanium diphenoxide, (η5-3-tert-butylcyclopentadienyl)(3,4-dimethyl-2-phenoxy) diphenylsilanetitanium diphenoxide, (η5-3-tert-butylcyclopentadienyl)(3-tert-butyl-5-methyl-2-phenoxy)diphenylsilanetitanium diphenoxide, (η5-3-tert-butylcyclopentadienyl)(3-tert-butyl-5-methoxy-2-phenoxy)diphenylsilanetitanium diphenoxide, (η5-3-tert-butylcyclopentadienyl)(3-tert-butyl-2-phenoxy) diphenylsilanetitanium diphenoxide, (η5-3-tert-butylcyclopentadienyl)(3-tert-butyl-5-chloro-2-phenoxy)diphenylsilanetitanium diphenoxide, (η5-3-tert-butylcyclopentadienyl)(3-phenyl-2-phenoxy) diphenylsilanetitanium diphenoxide, (η5-3-tert-butylcyclopentadienyl)(3-tert-butyldimethylsilyl-5-methyl-2-phenoxy)diphenylsilanetitanium diphenoxide, (η5-3-tert-butylcyclopentadienyl)(3-trimethylsilyl-5-methyl-2-phenoxy) diphenylsilanetitanium diphenoxide, (η5-cyclopentadienyl)(2-phenoxy) dimethylsilanetitanium(1,1'-binaphthyl-2,2'-dioxide), (η5-cyclopentadienyl)(3,4-dimethyl-2-phenoxy) dimethylsilanetitanium(1,1'-binaphthyl-2,2'-dioxide), (η5-cyclopentadienyl)(3-tert-butyl-5-methyl-2-phenoxy)dimethylsilanetitanium(1,1'-binaphthyl-2,2'-dioxide), (η5-cyclopentadienyl)(3-tert-butyl-5-methoxy-2-phenoxy)dimethylsilanetitanium(1,1'-binaphthyl-2,2'-dioxide), (η5-cyclopentadienyl)(3-tert-butyl-2-phenoxy)dimethylsilanetitanium(1,1'-binaphthyl-2,2'-dioxide), (η5-cyclopentadienyl)(3-tert-butyl-5-chloro-2-phenoxy)dimethylsilanetitanium(1,1'-binaphthyl-2,2'-dioxide), (η5-cyclopentadienyl)(3-phenyl-2-phenoxy)dimethylsilanetitanium(1,1'-binaphthyl-2,2'-dioxide), (η5-cyclopentadienyl)(3-tert-butyldimethylsilyl-5-methyl-2-phenoxy) dimethylsilanetitanium(1,1'-binaphthyl-2,2'-dioxide), (η5-cyclopentadienyl)(3-trimethylsilyl-5-methyl-2-phenoxy)dimethylsilanetitanium(1,1'-binaphthyl-2,2'-dioxide), (η5-cyclopentadienyl)(2-phenoxy) diphenylsilanetitanium(1,1'-binaphthyl-2,2'-dioxide), (η5-cyclopentadienyl)(3,4-dimethyl-2-phenoxy) diphenylsilanetitanium(1,1'-binaphthyl-2,2'-dioxide), (η5-cyclopentadienyl)(3-tert-butyl-5-methyl-2-phenoxy)diphenylsilanetitanium(1,1'-binaphthyl-2,2'-dioxide), (η5-cyclopentadienyl)(3-tert-butyl-5-methoxy-2-phenoxy)diphenylsilanetitanium(1,1'-binaphthyl-2,2'-dioxide), (η5-cyclopentadienyl)(3-tert-butyl-2-phenoxy)diphenylsilanetitanium(1,1'-binaphthyl-2,2'-dioxide), (η5-cyclopentadienyl)(3-tert-butyl-5-chloro-2-phenoxy)diphenylsilanetitanium(1,1'-binaphthyl-2,2'-dioxide), (η5-cyclopentadienyl)(3-phenyl-2-phenoxy)diphenylsilanetitanium(1,1'-binaphthyl-2,2'-dioxide), (η5-cyclopentadienyl)(3-tert-butyldimethylsilyl-5-methyl-2-phenoxy) diphenylsilanetitanium(1,1'-binaphthyl-2,2'-dioxide), (η5-cyclopentadienyl)(3-trimethylsilyl-5-methyl-2-phenoxy)diphenylsilanetitanium(1,1'-binaphthyl-2,2'-dioxide), (η5-2,3,4,5-tetramethylcyclopentadienyl)(2-phenoxy) dimethylsilanetitanium(1,1'-binaphthyl-2,2'-dioxide), (η5-2,3,4,5-tetramethylcyclopentadienyl)(3,4-dimethyl-2-phenoxy)dimethylsilanetitanium(1,1'-binaphthyl-2,2'-dioxide), (η5-2,3,4,5-tetramethylcyclopentadienyl)(3-tert-butyl-5-methyl-2-phenoxy)dimethylsilanetitanium(1,1'-binaphthyl-2,2'-dioxide), (η5-2,3,4,5-tetramethylcyclopentadienyl)(3-tert-butyl-5-methoxy-2-phenoxy) dimethylsilanetitanium(1,1'-binaphthyl-2,2'-dioxide), (η5-2,3,4,5-tetramethylcyclopentadienyl)(3-tert-butyl-2-phenoxy)dimethylsilanetitanium(1,1'-binaphthyl-2,2'-dioxide), (η5-2,3,4,5-tetramethylcyclopentadienyl)(3-tert-butyl-5-chloro-2-phenoxy) dimethylsilanetitanium(1,1'-binaphthyl-2,2'-dioxide), (η5-2,3,4,5-tetramethylcyclopentadienyl)(3-phenyl-2-phenoxy)dimethylsilanetitanium(1,1'-binaphthyl-2,2'-dioxide), (η5-2,3,4,5-tetramethylcyclopentadienyl)(3-tert-butyldimethylsilyl-5-methyl-2-phenoxy) dimethylsilanetitanium(1,1'-binaphthyl-2,2'-dioxide), (η5-2,3,4,5-tetramethylcyclopentadienyl)(3-trimethylsilyl-5-methyl-2-phenoxy) dimethylsilanetitanium(1,1'-binaphthyl-2,2'-dioxide), (η5-2,3,4,5-tetramethylcyclopentadienyl)(2-phenoxy) diphenylsilanetitanium(1,1'-binaphthyl-2,2'-dioxide), (η5-2,3,4,5-tetramethylcyclopentadienyl)(3,4-dimethyl-2-phenoxy)diphenylsilanetitanium(1,1'-binaphthyl-2,2'-dioxide), (η5-2,3,4,5-tetramethylcyclopentadienyl)(3-tert-butyl-5-methyl-2-phenoxy)diphenylsilanetitanium(1,1'-binaphthyl-2,2'-dioxide), (η5-2,3,4,5-tetramethylcyclopentadienyl)(3-tert-butyl-5-methoxy-2-phenoxy) diphenylsilanetitanium(1,1'-binaphthyl-2,2'-dioxide), (η5-2,3,4,5-tetramethylcyclopentadienyl)(3-tert-butyl-2-phenoxy)diphenylsilanetitanium(1,1'-binaphthyl-2, 2'-dioxide), (η5-2,3,4,5-tetramethylcyclopentadienyl) (3-tert-butyl-5-chloro-2-phenoxy) diphenylsilanetitanium(1,1'-binaphthyl-2,2'-dioxide), (η5-2,3,4,5-tetramethylcyclopentadienyl)(3-phenyl-2-phenoxy)diphenylsilanetitanium(1,1'-binaphthyl-2,2'-dioxide), (η5-2,3,4,5-tetramethylcyclopentadienyl)(3-tert-butyldimethylsilyl-5-methyl-2-phenoxy) diphenylsilanetitanium(1,1'-binaphthyl-2,2'-dioxide), (η5-2,3,4,5-tetramethylcyclopentadienyl)(3-trimethylsilyl-5-methyl-2-phenoxy) diphenylsilanetitanium(1,1'-binaphthyl-2,2'-dioxide), (η5-indenyl)(2-phenoxy)dimethylsilanetitanium(1,1'-binaphthyl-2,2'-dioxide), (η5-indenyl)(3,4-dimethyl-2-phenoxy)dimethylsilanetitanium(1,1'-binaphthyl-2,2'-dioxide), (η5-indenyl)(3-tert-butyl-5-methyl-2-phenoxy)dimethylsilanetitanium(1,1'-binaphthyl-2,2'-dioxide), (η5-indenyl)(3-tert-butyl-5-methoxy-2-phenoxy)dimethylsilanetitanium(1,1'-binaphthyl-2,2'-dioxide), (η5-indenyl)(3-tert-butyl-2-phenoxy) dimethylsilanetitanium(1,1'-binaphthyl-2,2'-dioxide), (η5-indenyl)(3-tert-butyl-5-chloro-2-phenoxy) dimethylsilanetitanium(1,1'-binaphthyl-2,2'-dioxide), (η5-indenyl)(3-phenyl-2-phenoxy) dimethylsilanetitanium(1,1'-binaphthyl-2,2'-dioxide), (η5-indenyl)(3-tert-butyldimethylsilyl-5-methyl-2-phenoxy)dimethylsilanetitanium(1,1'-binaphthyl-2,2'-dioxide), (η5-indenyl)(3-trimethylsilyl-5-methyl-2-phenoxy)dimethylsilanetitanium(1,1'-binaphthyl-2,2'-dioxide), (η5-indenyl)(2-phenoxy)diphenylsilanetitanium(1,1'-binaphthyl-2,2'-dioxide), (η5-indenyl)(3,4-dimethyl-2-phenoxy)diphenylsilanetitanium(1,1'-binaphthyl-2,2'-dioxide), (η5-indenyl)(3-tert-butyl-5-methyl-2-phenoxy)diphenylsilanetitanium(1,1'-binaphthyl-2,2'-dioxide), (η5-indenyl)(3-tert-butyl-5-methoxy-2-phenoxy)diphenylsilanetitanium(1,1'-binaphthyl-2,2'-dioxide), (η5-indenyl)(3-tert-butyl-2-phenoxy) diphenylsilanetitanium(1,1'-binaphthyl-2,2'-dioxide), (η5-indenyl)(3-tert-butyl-5-chloro-2-phenoxy) diphenylsilanetitanium(1,1'-binaphthyl-2,2'-dioxide), (η5-indenyl)(3-phenyl-2-phenoxy) diphenylsilanetitanium(1,1'-binaphthyl-2,2'-dioxide), (η5-indenyl)(3-tert-butyldimethylsilyl-5-methyl-2-phenoxy)diphenylsilanetitanium(1,1'-binaphthyl-2,2'-dioxide), (η5-indenyl)(3-trimethylsilyl-5-methyl-2-phenoxy)diphenylsilanetitanium(1,1'-binaphthyl-2,2'-dioxide), (η5-3-tert-butylcyclopentadienyl)(2-phenoxy) dimethylsilanetitanium(1,1'-binaphthyl-2,2'-dioxide), (η5-3-tert-butylcyclopentadienyl)(3,4-dimethyl-2-phenoxy)dimethylsilanetitanium(1,1'-binaphthyl-2,2'-dioxide), (η5-3-tert-butylcyclopentadienyl)(3-tert-butyl-5-methyl-2-phenoxy)dimethylsilanetitanium(1,1'-binaphthyl-2,2'-dioxide), (η5-3-tert-butylcyclopentadienyl)(3-tert-butyl-5-methoxy-2-phenoxy)dimethylsilanetitanium(1,1'-binaphthyl-2,2'-dioxide), (η5-3-tert-butylcyclopentadienyl)(3-tert-butyl-2-phenoxy)dimethylsilanetitanium(1,1'-binaphthyl-2,2'-dioxide), (η5-3-tert-butylcyclopentadienyl)(3-tert-butyl-5-chloro-2-phenoxy)dimethylsilanetitanium(1,1'-binaphthyl-2,2'- dioxide), (η5- 3-tert-butylcyclopentadienyl)(3-phenyl-2-phenoxy)dimethylsilanetitanium(1,1'-binaphthyl-2,2'-dioxide), (η5-3-tert-butylcyclopentadienyl)(3-tert-butyldimethylsilyl-5-methyl-2-phenoxy)dimethylsilanetitanium(1,1'-binaphthyl-2,2'-dioxide), (η5-3-tert-butylcyclopentadienyl)(3-trimethylsilyl-5-methyl-2-phenoxy)dimethylsilanetitanium(1,1'-binaphthyl-2,2'-dioxide), (η5-3-tert-butylcyclopentadienyl)(2-phenoxy)diphenylsilanetitanium(1,1'-binaphthyl-2,2'-dioxide), (η5-3-tert-butylcyclopentadienyl)(3,4-dimethyl-2-phenoxy)diphenylsilanetitanium(1,1'-binaphthyl-2,2'-dioxide), (η5-3-tert-butylcyclopentadienyl)(3-tert-butyl-5-methyl-2-phenoxy)diphenylsilanetitanium(1,1'-binaphthyl-2,2'-dioxide), (η5-3-tert-butylcyclopentadienyl)(3-tert-butyl-5-methoxy-2-phenoxy)diphenylsilanetitanium(1,1'-binaphthyl-2,2'-dioxide), (η5-3-tert-butylcyclopentadienyl)(3-tert-butyl-2-phenoxy)diphenylsilanetitanium(1,1'-binaphthyl-2,2'-dioxide), (η5-3-tert-butylcyclopentadienyl)(3-tert-butyl-5-chloro-2-phenoxy)diphenylsilanetitanium(1,1'-binaphthyl-2,2'-dioxide), (η5-3-tert-butylcyclopentadienyl)(3-phenyl-2-phenoxy)diphenylsilanetitanium(1,1'-binaphthyl-2,2'-dioxide), (η5-3-tert-butylcyclopentadienyl)(3-tert-butyldimethylsilyl-5-methyl-2-phenoxy)diphenylsilanetitanium(1,1'-binaphthyl-2,2'-dioxide), (η5-3-tert-butylcyclopentadienyl)(3-trimethylsilyl-5-methyl-2-phenoxy)diphenylsilanetitanium(1,1'-binaphthyl-2,2'-dioxide), and compounds obtained by substituting η5-2-methylcyclopentadienyl, η5-3-methylcyclopentadienyl, η5-2-tert-butylcyclopentadienyl, η5-2-n-butylcyclopentadienyl, η5-3-n-butylcyclopentadienyl, η5-fluorenyl for η5-cyclopentadienyl on the above-described compounds, further, compounds obtained by substituting di-4-methylphenoxide, bis(2,4,6-trimethylphenoxide), bis (pentafluorophenoxide) and the like for diphenoxide on the above-described compounds; and the like.

The aryloxytitanium complex (IV) can be produced also by a method in which the alkali metal aryloxides (V) are reacted with the halogenated titanium complex (II).

Examples of the aminotitanium complex (VI) in which A represents a carbon atom obtained according to the present invention include (η5-cyclopentadienyl)(2-phenoxy)methanetitaniumbis(diethylamide), (η5-cyclopentadienyl)(3,4-dimethyl-2-phenoxy)methanetitaniumbis(diethylamide), (η5-cyclopentadienyl)(3-tert-butyl-5-methyl-2-phenoxy)methanetitaniumbis(diethylamide), (η5-cyclopentadienyl)(3-tert-butyl-5-methoxy-2-phenoxy)methanetitaniumbis(diethylamide), (η5-cyclopentadienyl)(3-tert-butyl-2-phenoxy)methanetitaniumbis(diethylamide), (η5-cyclopentadienyl)(3-tert-butyl-5-chloro-2-phenoxy)methanetitaniumbis(diethylamide), (η5-cyclopentadienyl)(3-phenyl-2-phenoxy)methanetitaniumbis(diethylamide), (η5-cyclopentadienyl)(3-tert-butyldimethylsilyl-5-methyl-2-phenoxy)methanetitaniumbis(diethylamide), (η5-cyclopentadienyl)(3-trimethylsilyl-5-methyl-2-phenoxy)methanetitaniumbis(diethylamide), (η5-cyclopentadienyl)(2-phenoxy)dimethylmethanetitaniumbis(diethylamide), (η5-cyclopentadienyl)(3,4-dimethyl-2-phenoxy)dimethylmethanetitaniumbis(diethylamide), (η5-cyclopentadienyl)(3-tert-butyl-5-methyl-2-phenoxy)dimethylmethanetitaniumbis(diethylamide), (η5-cyclopentadienyl)(3-tert-butyl-5-methoxy-2-phenoxy)dimethylmethanetitaniumbis(diethylamide), (η5-cyclopentadienyl)(3-tert-butyl-2-phenoxy)dimethylmethanetitaniumbis(diethylamide), (η5-cyclopentadienyl)(3-tert-butyl-5-chloro-2-phenoxy)dimethylmethanetitaniumbis(diethylamide), (η5-cyclopentadienyl)(3-phenyl-2-phenoxy)dimethylmethanetitaniumbis(diethylamide), (η5-cyclopentadienyl)(3-tert-butyldimethylsilyl-5-methyl-2-phenoxy)dimethylmethanetitaniumbis(diethylamide), (η5-cyclopentadienyl)(3-trimethylsilyl-5-methyl-2-phenoxy)dimethylmethanetitaniumbis(diethylamide), (η5-cyclopentadienyl)(2-phenoxy)diphenylmethanetitaniumbis(diethylamide), (η5-cyclopentadienyl)(3,4-dimethyl-2-phenoxy)diphenylmethanetitaniumbis(diethylamide), (η5-cyclopentadienyl)(3-tert-butyl-5-methyl-2-phenoxy)diphenylmethanetitaniumbis(diethylamide), (η5-cyclopentadienyl)(3-tert-butyl-5-methoxy-2-phenoxy)diphenylmethanetitaniumbis(diethylamide), (η5-cyclopentadienyl)(3-tert-butyl-2-phenoxy)diphenylmethanetitaniumbis(diethylamide), (η5-cyclopentadienyl)(3-tert-butyl-5-chloro-2-phenoxy)diphenylmethanetitaniumbis(diethylamide), (η5-cyclopentadienyl)(3-phenyl-2-phenoxy)diphenylmethanetitaniumbis(diethylamide), (η5-cyclopentadienyl)(3-tert-butyldimethylsilyl-5-methyl-2-phenoxy)diphenylmethanetitaniumbis(diethylamide), (η5-cyclopentadienyl)(3-trimethylsilyl-5-methyl- 2-phenoxy)diphenylmethanetitaniumbis(diethylamide), (η5-2,3,4,5-tetramethylcyclopentadienyl)(2-phenoxy)methanetitaniumbis(diethylamide), (η5-2,3,4,5-tetramethylcyclopentadienyl)(3,4-dimethyl-2-phenoxy)methanetitaniumbis(diethylamide), (η5-2,3,4,5-tetramethylcyclopentadienyl)(3-tert-butyl-5-methyl-2-phenoxy)methanetitaniumbis(diethylamide), (η5-2,3,4,5-tetramethylcyclopentadienyl)(3-tert-butyl-5-methoxy-2-phenoxy)methanetitaniumbis(diethylamide), (η5-2,3,4,5-tetramethylcyclopentadienyl)(3-tert-butyl-2-phenoxy)methanetitaniumbis(diethylamide), (η5-2,3,4,5-tetramethylcyclopentadienyl)(3-tert-butyl-5-chloro-2-phenoxy)methanetitaniumbis(diethylamide), (η5-2,3,4,5-tetramethylcyclopentadienyl)(3-phenyl-2-phenoxy)methanetitaniumbis(diethylamide), (η5-2,3,4,5-tetramethylcyclopentadienyl)(3-tert-butyldimethylsilyl-5-methyl-2-phenoxy)methanetitaniumbis(diethylamide), (η5-2,3,4,5-tetramethylcyclopentadienyl)(3-trimethylsilyl-5-methyl-2-phenoxy)methanetitaniumbis(diethylamide), (η5-2,3,4,5-tetramethylcyclopentadienyl)(2-phenoxy)dimethylmethanetitaniumbis(diethylamide), (η5-2,3,4,5-tetramethylcyclopentadienyl)(3,4-dimethyl-2-phenoxy)dimethylmethanetitaniumbis(diethylamide), (η5-2,3,4,5-tetramethylcyclopentadienyl)(3-tert-butyl-5-methyl-2-phenoxy)dimethylmethanetitaniumbis(diethylamide), (η5-2,3,4,5-tetramethylcyclopentadienyl)(3-tert-butyl-5-methoxy-2-phenoxy)dimethylmethanetitaniumbis(diethylamide), (η5-2,3,4,5-tetramethylcyclopentadienyl)(3-tert-butyl-2-phenoxy)dimethylmethanetitaniumbis(diethylamide), (η5-2,3,4,5-tetramethylcyclopentadienyl)(3-tert-butyl-5-chloro-2-phenoxy)dimethylmethanetitaniumbis(diethylamide), (η5-2,3,4,5-tetramethylcyclopentadienyl)(3-phenyl-2-phenoxy)

dimethylmethanetitaniumbis(diethylamide), (η5-2,3,4, 5-tetramethylcyclopentadienyl)(3-tert-butyldimethylsilyl-5-methyl-2-phenoxy) dimethylmethanetitaniumbis(diethylamide), (η5-2,3,4, 5-tetramethylcyclopentadienyl)(3-trimethylsilyl-5-methyl-2-phenoxy)dimethylmethanetitaniumbis (diethylamide), (η5-2,3,4,5-tetramethylcyclopentadienyl)(2-phenoxy) diphenylmethanetitaniumbis(diethylamide), (η5-2,3,4, 5-tetramethylcyclopentadienyl)(3,4-dimethyl-2-phenoxy)diphenylmethanetitaniumbis(diethylamide), (η5-2,3,4,5-tetramethylcyclopentadienyl)(3-tert-butyl-5-methyl-2-phenoxy)diphenylmethanetitaniumbis (diethylamide), (η5-2,3,4,5-tetramethylcyclopentadienyl)(3-tert-butyl-5-methoxy-2-phenoxy)diphenylmethanetitaniumbis (diethylamide), (η5-2,3,4,5-tetramethylcyclopentadienyl)(3-tert-butyl- 2-phenoxy) diphenylmethanetitaniumbis(diethylamide), (η5-2,3,4, 5-tetramethylcyclopentadienyl)(3-tert-butyl-5-chloro-2-phenoxy)diphenylmethanetitaniumbis (diethylamide), (η5-2,3,4,5-tetramethylcyclopentadienyl)(3-phenyl-2-phenoxy) diphenylmethanetitaniumbis(diethylamide), (η5-2,3,4, 5-tetramethylcyclopentadienyl)(3-tert-butyldimethylsilyl-5-methyl-2-phenoxy) diphenylmethanetitaniumbis(diethylamide), (η5-2,3,4, 5-tetramethylcyclopentadienyl)(3-trimethylsilyl-5-methyl-2-phenoxy)diphenylmethanetitaniumbis (diethylamide), (η5-3-methylcyclopentadienyl)(2-phenoxy) methanetitaniumbis(diethylamide), (η5-3-methylcyclopentadienyl)(3,4-dimethyl-2-phenoxy) methanetitaniumbis(diethylamide), (η5-3-methylcyclopentadienyl)(3-tert-butyl-5-methyl-2-phenoxy)methanetitaniumbis(diethylamide), (η5-3-methylcyclopentadienyl)(3-tert-butyl-5-methoxy-2-phenoxy)methanetitaniumbis(diethylamide), (η5-3-methylcyclopentadienyl)(3-tert-butyl-2-phenoxy) methanetitaniumbis(diethylamide), (η5-3-methylcyclopentadienyl)(3-tert-butyl-5-chloro-2-phenoxy)methanetitaniumbis(diethylamide), (η5-3-methylcyclopentadienyl)(3-phenyl-2-phenoxy) methanetitaniumbis(diethylamide), (η5-3-methylcyclopentadienyl)(3-tert-butyldimethylsilyl-5-methyl-2-phenoxy)methanetitaniumbis (diethylamide), (η5-3-methylcyclopentadienyl)(3-trimethylsilyl-5-methyl-2-phenoxy) methanetitaniumbis(diethylamide), (η5-3-methylcyclopentadienyl)(2-phenoxy) dimethylmethanetitaniumbis(diethylamide), (η5-3-methylcyclopentadienyl)(3,4-dimethyl-2-phenoxy) dimethylmethanetitaniumbis(diethylamide), (η5-methylcyclopentadienyl)(3-tert-butyl-5-methyl-2-phenoxy)dimethylmethanetitaniumbis(diethylamide), (η5-3-methylcyclopentadienyl)(3-tert-butyl-5-methoxy-2-phenoxy)dimethylmethanetitaniumbis (diethylamide), (η5-3-methylcyclopentadienyl)(3-tert-butyl-2-phenoxy)dimethylmethanetitaniumbis (diethylamide), (η5-3-methylcyclopentadienyl)(3-tert-butyl-5-chloro-2-phenoxy) dimethylmethanetitaniumbis(diethylamide), (η5-3-methylcyclopentadienyl)(3-phenyl-2-phenoxy) dimethylmethanetitaniumbis(diethylamide), (η5-3-methylcyclopentadienyl)(3-tert-butyldimethylsilyl-5-methyl-2-phenoxy)dimethylmethanetitaniumbis (diethylamide), (η5-3-methylcyclopentadienyl)(3-trimethylsilyl-5-methyl-2-phenoxy) dimethylmethanetitaniumbis(diethylamide), (η5-3-methylcyclopentadienyl)(2-phenoxy) diphenylmathanetitaniumbis(diethylamide), (η5-3-methylcyclopentadienyl)(3,4-dimethyl-2-phenoxy) diphenylmathanetitaniumbis(diethylamide), (η5-3-methylcyclopentadienyl)(3-tert-butyl-5-methyl-2-phenoxy)diphenylmathanetitaniumbis(diethylamide), (η5-3-methylcyclopentadienyl)(3-tert-butyl-5-methoxy-2-phenoxy)diphenylmathanetitaniumbis (diethylamide), (η5-3-methylcyclopentadienyl)(3-tert-butyl-2-phenoxy)diphenylmathanetitaniumbis (diethylamide), (η5-3-methylcyclopentadienyl)(3-tert-butyl-5-chloro-2-phenoxy) diphenylmathanetitaniumbis(diethylamide), (η5-3-methylcyclopentadienyl)(3-phenyl-2-phenoxy) diphenylmathanetitaniumbis(diethylamide), (η5-3-methylcyclopentadienyl)(3-tert-butyldimethylsilyl-5-methyl-2-phenoxy)diphenylmathanetitaniumbis (diethylamide), (η5-3-methylcyclopentadienyl)(3-trimethylsilyl-5-methyl-2-phenoxy) diphenylmathanetitaniumbis(diethylamide), (η5-3-tert-butylcyclopentadienyl)(2-phenoxy) methanetitaniumbis(diethylamide), (η5-3-tert-butylcyclopentadienyl)(3,4-dimethyl-2-phenoxy) methanetitaniumbis(diethylamide), (η5-3-tert-butylcyclopentadienyl)(3-tert-butyl-5-methyl-2-phenoxy)methanetitaniumbis(diethylamide), (η5-3-tert-butylcyclopentadienyl)(3-tert-butyl-5-methoxy-2-phenoxy)methanetitaniumbis(diethylamide), (η5-3-tert-butylcyclopentadienyl)(3-tert-butyl-2-phenoxy) methanetitaniumbis(diethylamide), (η5-3-tert-butylcyclopentadienyl)(3-tert-butyl-5-chloro-2-phenoxy)methanetitaniumbis(diethylamide), (η5-3-tert-butylcyclopentadienyl)(3-phenyl-2-phenoxy) methanetitaniumbis(diethylamide), (η5-3-tert-butylcyclopentadienyl)(3-tert-butyldimethylsilyl-5-methyl-2-phenoxy)methanetitaniumbis(diethylamide), (η5-3-tert-butylcyclopentadienyl)(3-trimethylsilyl-5-methyl-2-phenoxy)methanetitaniumbis(diethylamide), (η5-3-tert-butylcyclopentadienyl)(2-phenoxy) dimethylmethanetitaniumbis(diethylamide), (η5-3-tert-butylcyclopentadienyl)(3,4-dimethyl-2-phenoxy) dimethylmethanetitaniumbis(diethylamide), (η5-3-tert-butylcyclopentadienyl)(3-tert-butyl-5-methyl-2-phenoxy)dimethylmethanetitaniumbis(diethylamide), (η5-3-tert-butylcyclopentadienyl)(3-tert-butyl-5-methoxy-2-phenoxy)dimethylmethanetitaniumbis (diethylamide), (η5-3-tert-butylcyclopentadienyl)(3-tert-butyl-2-phenoxy)dimethylmethanetitaniumbis (diethylamide), (η5-3-tert-butylcyclopentadienyl)(3-tert-butyl-5-chloro-2-phenoxy) dimethylmethanetitaniumbis(diethylamide), (η5-3-tert-butylcyclopentadienyl)(3-phenyl-2-phenoxy) dimethylmethanetitaniumbis(diethylamide), (η5-3-tert-butylcyclopentadienyl)(3-tert-butyldimethylsilyl-5-methyl-2-phenoxy)dimethylmethanetitaniumbis (diethylamide), (η5-3-tert-butylcyclopentadienyl)(3-trimethylsilyl-5-methyl-2-phenoxy) dimethylmethanetitaniumbis(diethylamide), (η5-3-tert-butylcyclopentadienyl)(2-phenoxy) diphenylmethanetitaniumbis(diethylamide), (η5-3-tert-butylcyclopentadienyl)(3,4-dimethyl-2-phenoxy) diphenylmethanetitaniumbis(diethylamide), (η5-3-tert-butylcyclopentadienyl)(3-tert-butyl-5-methyl-2-phenoxy)diphenylmethanetitaniumbis(diethylamide), (η5-3-tert-butylcyclopentadienyl)(3-tert-butyl-5- methoxy-2-phenoxy)diphenylmethanetitaniumbis (diethylamide), (η5-3-tert-butylcyclopentadienyl)(3-tert-butyl-2-phenoxy)diphenylmethanetitaniumbis (diethylamide), (η5-3-tert-butylcyclopentadienyl)(3-tert-butyl-5-chloro-2-phenoxy) diphenylmethanetitaniumbis(diethylamide), (η5-3-tert-butylcyclopentadienyl)(3-phenyl-2-phenoxy) diphenylmethanetitaniumbis(diethylamide), (η5-3-tert-butylcyclopentadienyl)(3-tert-butyldimethylsilyl-5-methyl-2-phenoxy)diphenylmethanetitaniumbis (diethylamide), (η5-3-tert-butylcyclopentadienyl)(3-trimethylsilyl-5-methyl-2-phenoxy) diphenylmethanetitaniumbis(diethylamide), (η5-cyclopentadienyl)(2-phenoxy)methanetitaniumbis (diphenylamide), (η5-cyclopentadienyl)(3,4-dimethyl-2-phenoxy)methanetitaniumbis(diphenylamide), (η5-cyclopentadienyl)(3-tert-butyl-5-methyl-2-phenoxy) methanetitaniumbis(diphenylamide), (η5-cyclopentadienyl)(3-tert-butyl-5-methoxy-2-phenoxy) methanetitaniumbis(diphenylamide), (η5-cyclopentadienyl)(3-tert-butyl-2-phenoxy) methanetitaniumbis(diphenylamide), (η5-cyclopentadienyl)(3-tert-butyl-5-chloro-2-phenoxy) methanetitaniumbis(diphenylamide), (η5-cyclopentadienyl)(3-phenyl-2-phenoxy) methanetitaniumbis(diphenylamide), (η5-cyclopentadienyl)(3-tert-butyldimethylsilyl-5-methyl-2-phenoxy)methanetitaniumbis(diphenylamide), (η5-cyclopentadienyl)(3-trimethylsilyl-5-methyl-2-phenoxy)methanetitaniumbis(diphenylamide), (η5-cyclopentadienyl)(2-phenoxy) dimethylmethanetitaniumbis(diphenylamide), (η5-cyclopentadienyl)(3,4-dimethyl-2-phenoxy) dimethylmethanetitaniumbis(diphenylamide), (η5-cyclopentadienyl)(3-tert-butyl-5-methyl-2-phenoxy) dimethylmethanetitaniumbis(diphenylamide), (η5-cyclopentadienyl)(3-tert-butyl-5-methoxy-2-phenoxy) dimethylmethanetitaniumbis(diphenylamide), (η5-cyclopentadienyl)(3-tert-butyl-2-phenoxy) dimethylmethanetitaniumbis(diphenylamide), (η5-cyclopentadienyl)(3-tert-butyl-5-chloro-2-phenoxy) dimethylmethanetitaniumbis(diphenylamide), (η5-cyclopentadienyl)(3-phenyl-2-phenoxy) dimethylmethanetitaniumbis(diphenylamide), (η5-cyclopentadienyl)(3-tert-butyldimethylsilyl-5-methyl-2-phenoxy)dimethylmethanetitaniumbis (diphenylamide), (η5-cyclopentadienyl)(3-trimethylsilyl-5-methyl-2-phenoxy) dimethylmethanetitaniumbis(diphenylamide), (η5-cyclopentadienyl)(2-phenoxy) diphenylmethanetitaniumbis(diphenylamide), (η5-cyclopentadienyl)(3,4-dimethyl-2-phenoxy) diphenylmethanetitaniumbis(diphenylamide), (η5-cyclopentadienyl)(3-tert-butyl-5-methyl-2-phenoxy) diphenylmethanetitaniumbis(diphenylamide), (η5-cyclopentadienyl)(3-tert-butyl-5-methoxy-2-phenoxy) diphenylmethanetitaniumbis(diphenylamide), (η5-cyclopentadienyl)(3-tert-butyl-2-phenoxy) diphenylmethanetitaniumbis(diphenylamide), (η5-cyclopentadienyl)(3-tert-butyl-5-chloro-2-phenoxy) diphenylmethanetitaniumbis(diphenylamide), (η5-cyclopentadienyl)(3-phenyl-2-phenoxy) diphenylmethanetitaniumbis(diphenylamide), (η5-cyclopentadienyl)(3-tert-butyldimethylsilyl-5-methyl-2-phenoxy)diphenylmethanetitaniumbis (diphenylamide), (η5-cyclopentadienyl)(3-trimethylsilyl-5-methyl-2-phenoxy) diphenylmethanetitaniumbis(diphenylamide), (η5-2,3,4,5-tetramethylcyclopentadienyl)(2-phenoxy) methanetitaniumbis(diphenylamide), (η5-2,3,4,5-tetramethylcyclopentadienyl)(3,4-dimethyl-2-phenoxy)methanetitaniumbis(diphenylamide), (η5-2,3,4,5-tetramethylcyclopentadienyl)(3-tert-butyl-5-methyl-2-phenoxy)methanetitaniumbis (diphenylamide), (η5-2,3,4,5-tetramethylcyclopentadienyl)(3-tert-butyl-5-methoxy-2-phenoxy)methanetitaniumbis(diphenylamide), (η5-2,3,4,5-tetramethylcyclopentadienyl)(3-tert-butyl-2-phenoxy)methanetitaniumbis(diphenylamide), (η5-2,3,4,5-tetramethylcyclopentadienyl)(3-tert-butyl-5-chloro-2-phenoxy)methanetitaniumbis (diphenylamide), (η5-2,3,4,5-tetramethylcyclopentadienyl)(3-phenyl-2-phenoxy) methanetitaniumbis(diphenylamide), (η5-2,3,4,5-tetramethylcyclopentadienyl)(3-tert-butyldimethylsilyl-5-methyl-2-phenoxy) methanetitaniumbis(diphenylamide), (η5-2,3,4,5-tetramethylcyclopentadienyl)(3-trimethylsilyl-5-methyl-2-phenoxy)methanetitaniumbis (diphenylamide), (η5-2,3,4,5-tetramethylcyclopentadienyl)(2-phenoxy) dimethylmethanetitaniumbis(diphenylamide), (η5-2,3,4,5-tetramethylcyclopentadienyl)(3,4-dimethyl-2-phenoxy)dimethylmethanetitaniumbis (diphenylamide), (η5-2,3,4,5-tetramethylcyclopentadienyl)(3-tert-butyl-5-methyl-2-phenoxy)dimethylmethanetitaniumbis (diphenylamide), (η5-2,3,4,5-tetramethylcyclopentadienyl)(3-tert-butyl-5-methoxy-2-phenoxy)dimethylmethanetitaniumbis (diphenylamide), (η5-2,3,4,5-tetramethylcyclopentadienyl)(3-tert-butyl-2-phenoxy) dimethylmethanetitaniumbis(diphenylamide), (η5-2,3,4,5-tetramethylcyclopentadienyl)(3-tert-butyl-5-chloro-2-phenoxy)dimethylmethanetitaniumbis (diphenylamide), (η5-2,3,4,5-tetramethylcyclopentadienyl)(3-phenyl-2-phenoxy) dimethylmethanetitaniumbis(diphenylamide), (η5-2,3,4,5-tetramethylcyclopentadienyl)(3-tert-butyldimethylsilyl-5-methyl-2-phenoxy) dimethylmethanetitaniumbis(diphenylamide), (η5-2,3,4,5-tetramethylcyclopentadienyl)(3-trimethylsilyl-5-methyl-2-phenoxy)dimethylmethanetitaniumbis (diphenylamide), (η5-2,3,4,5-tetramethylcyclopentadienyl)(2-phenoxy) diphenylmethanetitaniumbis(diphenylamide), (η5-2,3,4,5-tetramethylcyclopentadienyl)(3,4-dimethyl-2-phenoxy)diphenylmethanetitaniumbis (diphenylamide), (η5-2,3,4,5-tetramethylcyclopentadienyl)(3-tert-butyl-5-methyl-2-phenoxy)diphenylmethanetitaniumbis (diphenylamide), (η5-2,3,4,5-tetramethylcyclopentadienyl)(3-tert-butyl-5-methoxy-2-phenoxy)diphenylmethanetitaniumbis (diphenylamide), (η5-2,3,4,5-tetramethylcyclopentadienyl)(3-tert-butyl-2-phenoxy) diphenylmethanetitaniumbis(diphenylamide), (η5-2,3,4,5-tetramethylcyclopentadienyl)(3-tert-butyl-5-chloro-2-phenoxy)diphenylmethanetitaniumbis (diphenylamide), (η5-2,3,4,5-tetramethylcyclopentadienyl)(3-phenyl-2-phenoxy) diphenylmethanetitaniumbis(diphenylamide), (η5-2,3,4,5-tetramethylcyclopentadienyl)(3-tert-butyldimethylsilyl-5-methyl-2-phenoxy) diphenylmethanetitaniumbis(diphenylamide), (η5-2,3, 4,5-tetramethylcyclopentadienyl)(3-trimethylsilyl-5-methyl-2-phenoxy)diphenylmethanetitaniumbis(diphenylamide), (η5-3-methylcyclopentadienyl)(2-phenoxy)methanetitaniumbis(diphenylamide), (η5-3-methylcyclopentadienyl)(3,4-dimethyl-2-phenoxy)methanetitaniumbis(diphenylamide), (η5-3-methylcyclopentadienyl)(3-tert-butyl-5-methyl-2-phenoxy)methanetitaniumbis(diphenylamide), (η5-3-methylcyclopentadienyl)(3-tert-butyl-5-methoxy-2-phenoxy)methanetitaniumbis(diphenylamide), (η5-3-methylcyclopentadienyl)(3-tert-butyl-2-phenoxy)methanetitaniumbis(diphenylamide), (η5-3-methylcyclopentadienyl)(3-tert-butyl-5-chloro-2-phenoxy)methanetitaniumbis(diphenylamide), (η5-3-methylcyclopentadienyl)(3-phenyl-2-phenoxy)methanetitaniumbis(diphenylamide), (η5-3-methylcyclopentadienyl)(3-tert-butyldimethylsilyl-5-methyl-2-phenoxy)methanetitaniumbis(diphenylamide), (η5-3-methylcyclopentadienyl)(3-trimethylsilyl-5-methyl-2-phenoxy)methanetitaniumbis(diphenylamide), (η5-3-methylcyclopentadienyl)(2-phenoxy)dimethylmethanetitaniumbis(diphenylamide), (η5-3-methylcyclopentadienyl)(3,4-dimethyl-2-phenoxy)dimethylmethanetitaniumbis(diphenylamide), (η5-3-methylcyclopentadienyl)(3-tert-butyl-5-methyl-2-phenoxy)dimethylmethanetitaniumbis(diphenylamide), (η5-3-methylcyclopentadienyl)(3-tert-butyl-5-methoxy-2-phenoxy)dimethylmethanetitaniumbis(diphenylamide), (η5-3-methylcyclopentadienyl)(3-tert-butyl-2-phenoxy)dimethylmethanetitaniumbis(diphenylamide), (η5-3-methylcyclopentadienyl)(3-tert-butyl-5-chloro-2-phenoxy)dimethylmethanetitaniumbis(diphenylamide), (η5-3-methylcyclopentadienyl)(3-phenyl-2-phenoxy)dimethylmethanetitaniumbis(diphenylamide), (η5-3-methylcyclopentadienyl)(3-tert-butyldimethylsilyl-5-methyl-2-phenoxy)dimethylmethanetitaniumbis(diphenylamide), (η5-3-methylcyclopentadienyl)(3-trimethylsilyl-5-methyl-2-phenoxy)dimethylmethanetitaniumbis(diphenylamide), (η5-3-methylcyclopentadienyl)(2-phenoxy)diphenylmethanetitaniumbis(diphenylamide), (η5-3-methylcyclopentadienyl)(3,4-dimethyl-2-phenoxy)diphenylmethanetitaniumbis(diphenylamide), (η5-3-methylcyclopentadienyl)(3-tert-butyl-5-methyl-2-3-phenoxy)diphenylmethanetitaniumbis(diphenylamide), (η5-3-methylcyclopentadienyl)(3-tert-butyl-5-methoxy-2-phenoxy)diphenylmethanetitaniumbis(diphenylamide), (η5-3-methylcyclopentadienyl)(3-tert-butyl-2-phenoxy)diphenylmethanetitaniumbis(diphenylamide), (η5-3-methylcyclopentadienyl)(3-tert-butyl-5-chloro-2-phenoxy)diphenylmethanetitaniumbis(diphenylamide), (η5-3-methylcyclopentadienyl)(3-phenyl-2-phenoxy)diphenylmethanetitaniumbis(diphenylamide), (η5-3-methylcyclopentadienyl)(3-tert-butyldimethylsilyl-5-methyl-2-phenoxy)diphenylmethanetitaniumbis(diphenylamide), (η5-3-methylcyclopentadienyl)(3-trimethylsilyl-5-methyl-2-phenoxy)diphenylmethanetitaniumbis(diphenylamide), (η5-3-tert-butylcyclopentadienyl)(2-phenoxy)methanetitaniumbis(diphenylamide), (η5-3-tert-butylcyclopentadienyl)(3,4-dimethyl-2-phenoxy)methanetitaniumbis(diphenylamide), (η5-3-tert-butylcyclopentadienyl)(3-tert-butyl-5-methyl-2-phenoxy)methanetitaniumbis(diphenylamide), (η5-3-tert-butylcyclopentadienyl)(3-tert-butyl-5-methoxy-2-5-phenoxy)methanetitaniumbis(diphenylamide), (η5-3-tert-butylcyclopentadienyl)(3-tert-butyl-2-phenoxy)methanetitaniumbis(diphenylamide), (η5-3-tert-butylcyclopentadienyl)(3-tert-butyl-5-chloro-2-phenoxy)methanetitaniumbis(diphenylamide), (η5-3-tert-butylcyclopentadienyl)(3-phenyl-2-phenoxy)methanetitaniumbis(diphenylamide), (η5-3-tert-butylcyclopentadienyl)(3-tert-butyldimethylsilyl-5-methyl-2-phenoxy)methanetitaniumbis(diphenylamide), (η5-3-tert-butylcyclopentadienyl)(3-trimethylsilyl-5-methyl-2-phenoxy)methanetitaniumbis(diphenylamide), (η5-3-tert-butylcyclopentadienyl)(2-phenoxy)dimethylmethanetitaniumbis(diphenylamide), (η5-3-tert-butylcyclopentadienyl)(3,4-dimethyl-2-phenoxy)dimethylmethanetitaniumbis(diphenylamide), (η5-3-tert-butylcyclopentadienyl)(3-tert-butyl-5-methyl-2-phenoxy)dimethylmethanetitaniumbis(diphenylamide), (η5-3-tert-butylcyclopentadienyl)(3-tert-butyl-5-methoxy-2-phenoxy)dimethylmethanetitaniumbis(diphenylamide), (η5-3-tert-butylcyclopentadienyl)(3-tert-butyl-2-phenoxy)dimethylmethanetitaniumbis(diphenylamide), (η5-3-tert-butylcyclopentadienyl)(3-tert-butyl-5-chloro-2-phenoxy)dimethylmethanetitaniumbis(diphenylamide), (η5-3-tert-butylcyclopentadienyl)(3-phenyl-2-phenoxy)dimethylmethanetitaniumbis(diphenylamide), (η5-3-tert-butylcyclopentadienyl)(3-tert-butyldimethylsilyl-5-methyl-2-phenoxy)dimethylmethanetitaniumbis(diphenylamide), (η5-3-tert-butylcyclopentadienyl)(3-trimethylsilyl-5-methyl-2-phenoxy)dimethylmethanetitaniumbis(diphenylamide), (η5-3-tert-butylcyclopentadienyl)(2-phenoxy)diphenylmethanetitaniumbis(diphenylamide), (η5-3-tert-butylcyclopentadienyl)(3,4-dimethyl-2-phenoxy)diphenylmethanetitaniumbis(diphenylamide), (η5-3-tert-butylcyclopentadienyl)(3-tert-butyl-5-methyl-2-phenoxy)diphenylmethanetitaniumbis(diphenylamide), (η5-3-tert-butylcyclopentadienyl)(3-tert-butyl-5-methoxy-2-phenoxy)diphenylmethanetitaniumbis(diphenylamide), (η5-3-tert-butylcyclopentadienyl)(3-tert-butyl-2-phenoxy)diphenylmethanetitaniumbis(diphenylamide), (η5-3-tert-butylcyclopentadienyl)(3-tert-butyl-5-chloro-2-phenoxy)diphenylmethanetitaniumbis(diphenylamide), (η5-3-tert-butylcyclopentadienyl)(3-phenyl-2-phenoxy)diphenylmethanetitaniumbis(diphenylamide), (η5-3-tert-butylcyclopentadienyl)(3-tert-butyldimethylsilyl-5-methyl-2-phenoxy)diphenylmethanetitaniumbis(diphenylamide), (η5-3-tert-butylcyclopentadienyl)(3-trimethylsilyl-5-methyl-2-phenoxy)diphenylmethanetitaniumbis(diphenylamide), and compounds obtained by substituting η5-2-5 methylcyclopentadienyl, η5-2-tert-butylcyclopentadienyl, η5-2-n-butylcyclopentadienyl, η5-3-n-butylcyclopentadienyl, η5-indenyl, η5-fluorenyl for η5-cyclopentadienyl on the above-described compounds, further, compounds obtained by substituting dimethylamide, dipropylamide, diisopropylamide, dibutylamide, bis(trimethylsilylamide), piperidide, dicyclohexylamide, dibenzylamide and the like for diethylamide; and the like.

Examples of the aminotitanium complex (VI) in which A represents a silicon atom obtained according to the present invention include (η5-cyclopentadienyl)(2-phenoxy)dimethylsilanetitaniumbis(diethylamide), (η5-cyclopentadienyl)(3,4-dimethyl-2-phenoxy)dimethylsilanetitaniumbis(diethylamide), (η5-cyclopentadienyl)(3-tert-butyl-5-methyl-2-phenoxy)dimethylsilanetitaniumbis(diethylamide), (η5-cyclopentadienyl)(3-tert-butyl-5-methoxy-2-phenoxy)dimethylsilanetitaniumbis(diethylamide), (η5-cyclopentadienyl)(3-tert-butyl-2-phenoxy)dimethylsilanetitaniumbis(diethylamide), (η5-cyclopentadienyl)(3-tert-butyl-5-chloro-2-phenoxy)dimethylsilanetitaniumbis(diethylamide), (η5-cyclopentadienyl)(3-phenyl-2-phenoxy)dimethylsilanetitaniumbis(diethylamide), (η5-cyclopentadienyl)(3-tert-butyldimethylsilyl-5-methyl-2-phenoxy)dimethylsilanetitaniumbis(diethylamide), (η5-cyclopentadienyl)(3-trimethylsilyl-5-methyl-2-phenoxy)dimethylsilanetitaniumbis(diethylamide), (η5-cyclopentadienyl)(2-phenoxy)diphenylsilanetitaniumbis(diethylamide), (η5-cyclopentadienyl)(3,4-dimethyl-2-phenoxy)diphenylsilanetitaniumbis(diethylamide), (η5-cyclopentadienyl)(3-tert-butyl-5-methyl-2-phenoxy)diphenylsilanetitaniumbis(diethylamide), (η5-cyclopentadienyl)(3-tert-butyl-5-methoxy-2-phenoxy)diphenylsilanetitaniumbis(diethylamide), (η5-cyclopentadienyl)(3-tert-butyl-2-phenoxy)diphenylsilanetitaniumbis(diethylamide), (η5-cyclopentadienyl)(3-tert-butyl-5-chloro-2-phenoxy)diphenylsilanetitaniumbis(diethylamide), (η5-cyclopentadienyl)(3-phenyl-2-phenoxy)diphenylsilanetitaniumbis(diethylamide), (η5-cyclopentadienyl)(3-tert-butyldimethylsilyl-5-methyl-2-phenoxy)diphenylsilanetitaniumbis(diethylamide), (η5-cyclopentadienyl)(3-trimethylsilyl-5-methyl-2-phenoxy)diphenylsilanetitaniumbis(diethylamide), (η5-2,3,4,5-tetramethylcyclopentadienyl)(2-phenoxy)dimethylsilanetitaniumbis(diethylamide), (η5-2,3,4,5-tetramethylcyclopentadienyl)(3,4-dimethyl-2-phenoxy)dimethylsilanetitaniumbis(diethylamide), (η5-2,3,4,5-tetramethylcyclopentadienyl)(3-tert-butyl-5-methyl-2-phenoxy)dimethylsilanetitaniumbis(diethylamide), (η5-2,3,4,5-tetramethylcyclopentadienyl)(3-tert-butyl-5-methoxy-2-phenoxy)dimethylsilanetitaniumbis(diethylamide), (η5-2,3,4,5-tetramethylcyclopentadienyl)(3-tert-butyl-2-phenoxy)dimethylsilanetitaniumbis(diethylamide), (η5-2,3,4,5-tetramethylcyclopentadienyl)(3-tert-butyl-5-chloro-2-phenoxy)dimethylsilanetitaniumbis(diethylamide), (η5-2,3,4,5-tetramethylcyclopentadienyl)(3-phenyl-2-phenoxy)dimethylsilanetitaniumbis(diethylamide), (η5-2,3,4,5-tetramethylcyclopentadienyl)(3-tert-butyldimethylsilyl-5-methyl-2-phenoxy)dimethylsilanetitaniumbis(diethylamide), (η5-2,3,4,5-tetramethylcyclopentadienyl)(3-trimethylsilyl-5-methyl-2-phenoxy)dimethylsilanetitaniumbis(diethylamide), (η5-2,3,4,5-tetramethylcyclopentadienyl)(2-phenoxy)diphenylsilanetitaniumbis(diethylamide), (η5-2,3,4,5-tetramethylcyclopentadienyl)(3,4-dimethyl-2-phenoxy)diphenylsilanetitaniumbis(diethylamide), (η5-2,3,4,5-tetramethylcyclopentadienyl)(3-tert-butyl-5-methyl-2-phenoxy)diphenylsilanetitaniumbis(diethylamide), (η5-2,3,4,5-tetramethylcyclopentadienyl)(3-tert-butyl-5-methoxy-2-phenoxy)diphenylsilanetitaniumbis(diethylamide), (η5-2,3,4,5-tetramethylcyclopentadienyl)(3-tert-butyl-2-phenoxy)diphenylsilanetitaniumbis(diethylamide), (η5-2,3,4,5-tetramethylcyclopentadienyl)(3-tert-butyl-5-chloro-2-phenoxy)diphenylsilanetitaniumbis(diethylamide), (η5-2,3,4,5-tetramethylcyclopentadienyl)(3-phenyl-2-phenoxy)diphenylsilanetitaniumbis(diethylamide), (η5-2,3,4,5-tetramethylcyclopentadienyl)(3-tert-butyldimethylsilyl-5-methyl-2-phenoxy)diphenylsilanetitaniumbis(diethylamide), (η5-2,3,4,5-tetramethylcyclopentadienyl)(3-trimethylsilyl-5-methyl-2-phenoxy)diphenylsilanetitaniumbis(diethylamide), (η5-indenyl)(2-phenoxy)dimethylsilanetitaniumbis(diethylamide), (η5-indenyl)(3,4-dimethyl-2-phenoxy)dimethylsilanetitaniumbis(diethylamide), (η5-indenyl)(3-tert-butyl-5-methyl-2-phenoxy)dimethylsilanetitaniumbis(diethylamide), (η5-indenyl)(3-tert-butyl-5-methoxy-2-phenoxy)dimethylsilanetitaniumbis(diethylamide), (η5-indenyl)(3-tert-butyl-2-phenoxy)dimethylsilanetitaniumbis(diethylamide), (η5-indenyl)(3-tert-butyl-5-chloro-2-phenoxy)dimethylsilanetitaniumbis(diethylamide), (η5-indenyl)(3-phenyl-2-phenoxy)dimethylsilanetitaniumbis(diethylamide), (η5-indenyl)(3-tert-butyldimethylsilyl-5-methyl-2-phenoxy)dimethylsilanetitaniumbis(diethylamide), (η5-indenyl)(3-trimethylsilyl-5-methyl-2-phenoxy)dimethylsilanetitaniumbis(diethylamide), (η5-indenyl)(2-phenoxy)diphenylsilanetitaniumbis(diethylamide), (η5-indenyl)(3,4-dimethyl-2-phenoxy)diphenylsilanetitaniumbis(diethylamide), (η5-indenyl)(3-tert-butyl-5-methyl-2-phenoxy)diphenylsilanetitaniumbis(diethylamide), (η5-indenyl)(3-tert-butyl-5-methoxy-2-phenoxy)diphenylsilanetitaniumbis(diethylamide), (η5-indenyl)(3-tert-butyl-2-phenoxy)diphenylsilanetitaniumbis(diethylamide), (η5-indenyl)(3-tert-butyl-5-chloro-2-phenoxy)diphenylsilanetitaniumbis(diethylamide), (η5-indenyl)(3-phenyl-2-phenoxy)diphenylsilanetitaniumbis(diethylamide), (η5-indenyl)(3-tert-butyldimethylsilyl-5-methyl-2-phenoxy)diphenylsilanetitaniumbis(diethylamide), (η5-indenyl)(3-trimethylsilyl-5-methyl-2-phenoxy)diphenylsilanetitaniumbis(diethylamide), (η5-3-tert-butylcyclopentadienyl)(2-phenoxy)dimethylsilanetitaniumbis(diethylamide), (η5-3-tert-butylcyclopentadienyl)(3,4-dimethyl-2-phenoxy)dimethylsilanetitaniumbis(diethylamide), (η5-3-tert-butylcyclopentadienyl)(3-tert-butyl-5-methyl-2-phenoxy)dimethylsilanetitaniumbis(diethylamide), (η5-3-tert-butylcyclopentadienyl)(3-tert-butyl-5-methoxy-2-phenoxy)dimethylsilanetitaniumbis(diethylamide), (η5-3-tert-butylcyclopentadienyl)(3-tert-butyl-2-phenoxy)dimethylsilanetitaniumbis(diethylamide), (η5-3-tert-butylcyclopentadienyl)(3-tert-butyl-5-chloro-2-phenoxy)dimethylsilanetitaniumbis(diethylamide), (η5-3-tert-butylcyclopentadienyl)(3-phenyl-2-phenoxy)dimethylsilanetitaniumbis(diethylamide), (η5-3-tert-butylcyclopentadienyl)(3-tert-butyldimethylsilyl-5-methyl-2-phenoxy)dimethylsilanetitaniumbis(diethylamide), (η5-3-tert-butylcyclopentadienyl)(3-trimethylsilyl-5-methyl-2-phenoxy)dimethylsilanetitaniumbis(diethylamide), (η5-3-tert-butylcyclopentadienyl)(2-phenoxy) diphenylsilanetitaniumbis(diethylamide), (η5-3-tert-butylcyclopentadienyl)(3,4-dimethyl-2-phenoxy) diphenylsilanetitaniumbis(diethylamide), (η5-3-tert-butylcyclopentadienyl)(3-tert-butyl-5-methyl-2-phenoxy)diphenylsilanetitaniumbis(diethylamide), (η5-3-tert-butylcyclopentadienyl)(3-tert-butyl-5-methoxy-2-phenoxy)diphenylsilanetitaniumbis (diethylamide), (η5-3-tert-butylcyclopentadienyl)(3-tert-butyl-2-phenoxy)diphenylsilanetitaniumbis (diethylamide), (η5-3-tert-butylcyclopentadienyl)(3-tert-butyl-5-chloro-2-phenoxy) diphenylsilanetitaniumbis(diethylamide), (η5-3-tert-butylcyclopentadienyl)(3-phenyl-2-phenoxy) diphenylsilanetitaniumbis(diethylamide), (η5-3-tert-butylcyclopentadienyl)(3-tert-butyldimethylsilyl-5-methyl-2-phenoxy)diphenylsilanetitaniumbis (diethylamide), (η5-3-tert-butylcyclopentadienyl)(3-trimethylsilyl-5-methyl-2-phenoxy) diphenylsilanetitaniumbis(diethylamide), (η5-cyclopentadienyl)(2-phenoxy) dimethylsilanetitaniumbis(diphenylamide), (η5-cyclopentadienyl)(3,4-dimethyl-2-phenoxy) dimethylsilanetitaniumbis(diphenylamide), (η5-cyclopentadienyl)(3-tert-butyl-5-methyl-2-phenoxy) dimethylsilanetitaniumbis(diphenylamide), (η5-cyclopentadienyl)(3-tert-butyl-5-methoxy-2-phenoxy) dimethylsilanetitaniumbis(diphenylamide), (η5-cyclopentadienyl)(3-tert-butyl-2-phenoxy) dimethylsilanetitaniumbis(diphenylamide), (η5-cyclopentadienyl)(3-tert-butyl-5-chloro-2-phenoxy) dimethylsilanetitaniumbis(diphenylamide), (η5-cyclopentadienyl)(3-phenyl- 2-phenoxy) dimethylsilanetitaniumbis(diphenylamide), (η5-cyclopentadienyl)(3-tert-butyldimethylsilyl-5-methyl-2-phenoxy)dimethylsilanetitaniumbis(diphenylamide), (η5-cyclopentadienyl)(3-trimethylsilyl-5-methyl-2-phenoxyYdimethylsilanetitaniumbis(diphenylamide), (η5-cyclopentadienyl)(2-phenoxy) diphenylsilanetitaniumbis(diphenylamide), (η5-cyclopentadienyl)(3,4-dimethyl-2-phenoxy) diphenylsilanetitaniumbis(diphenylamide), (η5-cyclopentadienyl)(3-tert-butyl-5-methyl-2-phenoxy) diphenylsilanetitaniumbis(diphenylamide), (η5-cyclopentadienyl)(3-tert-butyl-5-methoxy-2-phenoxy) diphenylsilanetitaniumbis(diphenylamide), (η5-cyclopentadienyl)(3-tert-butyl-2-phenoxy) diphenylsilanetitaniumbis(diphenylamide), (η5-cyclopentadienyl)(3-tert-butyl-5-chloro-2-phenoxy) diphenylsilanetitaniumbis(diphenylamide), (η5-cyclopentadienyl)(3-phenyl-2-phenoxy) diphenylsilanetitaniumbis(diphenylamide), (η5-cyclopentadienyl)(3-tert-butyldimethylsilyl-5-methyl-2-phenoxy)diphenylsilanetitaniumbis(diphenylamide), (η5-cyclopentadienyl)(3-trimethylsilyl-5-methyl-2-phenoxy)diphenylsilanetitaniumbis(diphenylamide), (η5-2,3,4,5-tetramethylcyclopentadienyl)(2-phenoxy) dimethylsilanetitaniumbis(diphenylamide), (η5-2,3,4,5-tetramethylcyclopentadienyl)(3,4-dimethyl-2-phenoxy)dimethylsilanetitaniumbis(diphenylamide), (η5-2,3,4,5-tetramethylcyclopentadienyl)(3-tert-butyl-5-methyl-2-phenoxy)dimethylsilanetitaniumbis (diphenylamide), (η5-2,3,4,5-tetramethylcyclopentadienyl)(3-tert-butyl-5-methoxy-2-phenoxy)dimethylsilanetitaniumbis(diphenylamide), (η5-2,3,4,5-tetramethylcyclopentadienyl)(3-tert-butyl-2-phenoxy)dimethylsilanetitaniumbis(diphenylamide), (η5-2,3,4,5-tetramethylcyclopentadienyl)(3-tert-butyl-5-chloro-2-phenoxy)dimethylsilanetitaniumbis (diphenylamide), (η5-2,3,4,5-tetramethylcyclopentadienyl)(3-phenyl-2-phenoxy) dimethylsilanetitaniumbis(diphenylamide), (η5-2,3,4,5-tetramethylcyclopentadienyl)(3-tert-butyldimethylsilyl-5-methyl-2-phenoxy) dimethylsilanetitaniumbis(diphenylamide), (η5-2,3,4,5-tetramethylcyclopentadienyl)(3-trimethylsilyl-5-methyl-2-phenoxy)dimethylsilanetitaniumbis (diphenylamide), (η5-2,3,4,5-tetramethylcyclopentadienyl)(2-phenoxy) diphenylsilanetitaniumbis(diphenylamide), (η5-2,3,4,5-tetramethylcyclopentadienyl)(3,4-dimethyl-2-phenoxy)diphenylsilanetitaniumbis(diphenylamide), (η5-2,3,4,5-tetramethylcyclopentadienyl)(3-tert-butyl-5-methyl-2-phenoxy)diphenylsilanetitaniumbis (diphenylamide), (η5-2,3,4,5-tetramethylcyclopentadienyl)(3-tert-butyl-5-methoxy-2-phenoxy)diphenylsilanetitaniumbis(diphenylamide), (η5-2,3,4,5-tetramethylcyclopentadienyl)(3-tert-butyl-2-phenoxy)diphenylsilanetitaniumbis(diphenylamide), (η5-2,3,4,5-tetramethylcyclopentadienyl)(3-tert-butyl-5-chloro-2-phenoxy)diphenylsilanetitaniumbis (diphenylamide), (η5-2,3,4,5-tetramethylcyclopentadienyl)(3-phenyl-2-phenoxy) diphenylsilanetitaniumbis(diphenylamide), (η5-2,3,4,5-tetramethylcyclopentadienyl)(3-tert-butyldimethylsilyl-5-methyl-2-phenoxy) diphenylsilanetitaniumbis(diphenylamide), (η5-2,3,4,5-tetramethylcyclopentadienyl)(3-trimethylsilyl-5-methyl-2-phenoxy)diphenylsilanetitaniumbis (diphenylamide), (η5-indenyl)(2-phenoxy)dimethylsilanetitaniumbis (diphenylamide), (η5-indenyl)(3,4-dimethyl-2-phenoxy)dimethylsilanetitaniumbis(diphenylamide), (η5-indenyl)(3-tert-butyl-5-methyl-2-phenoxy) dimethylsilanetitaniumbis(diphenylamide), (η5-indenyl)(3-tert-butyl-5-methoxy-2-phenoxy) dimethylsilanetitaniumbis(diphenylamide), (η5-indenyl)(3-tert-butyl-2-phenoxy) dimethylsilanetitaniumbis(diphenylamide), (η5-indenyl)(3-tert-butyl-5-chloro-2-phenoxy) dimethylsilanetitaniumbis(diphenylamide), (η5-indenyl)(3-phenyl-2-phenoxy) dimethylsilanetitaniumbis(diphenylamide), (η5-indenyl)(3-tert-butyldimethylsilyl-5-methyl-2-phenoxy)dimethylsilanetitaniumbis(diphenylamide), (η5-indenyl)(3-trimethylsilyl-5-methyl-2-phenoxy) dimethylsilanetitaniumbis(diphenylamide), (η5-indenyl)(2-phenoxy)diphenylsilanetitaniumbis (diphenylamide), (η5-indenyl)(3,4-dimethyl-2-phenoxy)diphenylsilanetitaniumbis(diphenylamide), (η5-indenyl)(3-tert-butyl-5-methyl-2-phenoxy) diphenylsilanetitaniumbis(diphenylamide), (η5-indenyl)(3-tert-butyl-5-methoxy-2-phenoxy) diphenylsilanetitaniumbis(diphenylamide), (η5-indenyl)(3-tert-butyl-2-phenoxy) diphenylsilanetitaniumbis(diphenylamide), (η5-indenyl)(3-tert-butyl-5-chloro-2-phenoxy) diphenylsilanetitaniumbis(diphenylamide), (η5-indenyl)(3-phenyl-2-phenoxy) diphenylsilanetitaniumbis(diphenylamide), (η5-indenyl)(3-tert-butyldimethylsilyl-5-methyl-2-phenoxy)diphenylsilanetitaniumbis(diphenylamide), (η5-indenyl)(3-trimethylsilyl-5-methyl- 2-phenoxy) diphenylsilanetitaniumbis(diphenylamide), (η5-3-tert-butylcyclopentadienyl)(2-phenoxy) dimethylsilanetitaniumbis(diphenylamide), (η5-3-tert-butylcyclopentadienyl)(3,4-dimethyl-2-phenoxy) dimethylsilanetitaniumbis(diphenylamide), (η5-3-tert-butylcyclopentadienyl)(3-tert-butyl-5-methyl-2-phenoxy)dimethylsilanetitaniumbis(diphenylamide), (η5-3-tert-butylcyclopentadienyl), (3-tert-butyl-5-methoxy-2-phenoxy)dimethylsilanetitaniumbis (diphenylamide), (η5-3-tert-butylcyclopentadienyl)(3-tert-butyl-2-phenoxy)dimethylsilanetitaniumbis (diphenylamide), (η5-3-tert-butylcyclopentadienyl)(3-tert-butyl-5-chloro-2-phenoxy) dimethylsilanetitaniumbis(diphenylamide), (η5-3-tert-butylcyclopentadienyl)(3-phenyl-2-phenoxy) dimethylsilanetitaniumbis(diphenylamide), (η5-3-tert-butylcyclopentadienyl)(3-tert-butyldimethylsilyl-5-methyl-2-phenoxy)dimethylsilanetitaniumbis (diphenylamide), (η5-3-tert-butylcyclopentadienyl)(3-trimethylsilyl-5-methyl-2-phenoxy) dimethylsilanetitaniumbis(diphenylamide), (η5-3-tert-butylcyclopentadienyl)(2-phenoxy) diphenylsilanetitaniumbis(diphenylamide), (η5-3-tert-butylcyclopentadienyl)(3,4-dimethyl-2-phenoxy) diphenylsilanetitaniumbis(diphenylamide), (η5-3-tert-butylcyclopentadienyl)(3-tert-butyl-5-methyl-2-phenoxy)diphenylsilanetitaniumbis(diphenylamide), (η5-3-tert-butylcyclopentadienyl)(3-tert-butyl-5-methoxy-2-phenoxy)diphenylsilanetitaniumbis (diphenylamide), (η5-3-tert-butylcyclopentadienyl)(3-tert-butyl-2-phenoxy)diphenylsilanetitaniumbis (diphenylamide), (η5-3-tert-butylcyclopentadienyl)(3-tert-butyl-5-chloro-2-phenoxy) diphenylsilanetitaniumbis(diphenylamide), (η5-3-tert-butylcyclopentadienyl)(3-phenyl-2-phenoxy) diphenylsilanetitaniumbis(diphenylamide), (η5-3-tert-butylcyclopentadienyl)(3-tert-butyldimethylsilyl-5-methyl-2-phenoxy)diphenylsilanetitaniumbis (diphenylamide), (η5-3-tert-butylcyclopentadienyl)(3-trimethylsilyl-5-methyl-2-phenoxy) diphenylsilanetitaniumbis(diphenylamide), and compounds obtained by substituting η5-2-methylcyclopentadienyl, η5-3-methylcyclopentadienyl, η5-2-tert-butylcyclopentadienyl, η5-2-n-butylcyclopentadienyl, η5-3-n-butylcyclopentadienyl, η5-fluorenyl for η5-cyclopentadienyl on the above-described compounds, compounds obtained by optional substitution by dimethoxysilane or diethoxysilane for dimethylsilane on the above-described compounds, and further, compounds obtained by substituting dimethylamide, dipropylamide, diisopropylamide, dibutylamide, bis(trimethylsilylamide), piperidide, dicyclohexylamide, dibenzylamide and the like for diethylamide on the above-described compounds; and the like.

The aminotitanium complex (VI) can be produced by a method in which the alkali metal amides (VII) are reacted with the halogenated titanium complex (II)

Examples of halogen in the substituents $X^1$ and $X^2$ in the halogenated titanium complex (II) include fluorine, chlorine, bromine, iodine and the like.

Examples of the halogenated titanium complex (II) in which A represents a carbon atom include (η5-cyclopentadienyl)(2-phenoxy)methanetitanium dichloride, (η5-cyclopentadienyl)(3,4-dimethyl-2-phenoxy) methanetitanium dichloride, (η5-cyclopentadienyl)(3-tert-butyl-5-methyl-2-phenoxy)methanetitanium dichloride, (η5-cyclopentadienyl)(3-tert-butyl-5-methoxy-2-phenoxy) methanetitanium dichloride, (η5-cyclopentadienyl)(3-tert-butyl-2-phenoxy)methanetitanium dichloride, (η5-cyclopentadienyl)(3-tert-butyl-5-chloro-2-phenoxy) methanetitanium dichloride, (η5-cyclopentadienyl)(3-phenyl-2-phenoxy)methanetitanium dichloride, (η5-cyclopentadienyl)(3-tert-butyldimethylsilyl-5-methyl-2-phenoxy)methanetitanium dichloride, (η5-cyclopentadienyl)(3-trimethylsilyl-5-methyl-2-phenoxy)methanetitanium dichloride, (η5-cyclopentadienyl)(2-phenoxy) dimethylmethanetitanium dichloride, (η5-cyclopentadienyl)(3,4-dimethyl-2-phenoxy) dimethylmethanetitanium dichloride, (η5-cyclopentadienyl)(3-tert-butyl-5-methyl-2-phenoxy) dimethylmethanetitanium dichloride, (η5-cyclopentadienyl)(3-tert-butyl-5-methoxy-2-phenoxy) dimethylmethanetitanium dichloride, (η5-cyclopentadienyl)(3-tert-butyl-2-phenoxy) dimethylmethanetitanium dichloride, (η5-cyclopentadienyl)(3-tert-butyl-5-chloro-2-phenoxy) dimethylmethanetitanium dichloride, (η5-cyclopentadienyl)(3-phenyl-2-phenoxy) dimethylmethanetitanium dichloride, (η5-cyclopentadienyl)(3-tert-butyldimethylsilyl-5-methyl-2-phenoxy)dimethylmethanetitanium dichloride, (η5-cyclopentadienyl)(3-trimethylsilyl-5-methyl-2-phenoxy)dimethylmethanetitanium dichloride, (η5-cyclopentadienyl)(2-phenoxy) diphenylmethanetitanium dichloride, (η5-cyclopentadienyl)(3,4-dimethyl-2-phenoxy) diphenylmethanetitanium dichloride, (η5-cyclopentadienyl)(3-tert-butyl-5-methyl-2-phenoxy) diphenylmethanetitanium dichloride, (η5-cyclopentadienyl)(3-tert-butyl-5-methoxy- 2-phenoxy) diphenylmethanetitanium dichloride, (η5-cyclopentadienyl)(3-tert-butyl-2-phenoxy) diphenylmethanetitanium dichloride, (η5-cyclopentadienyl)(3-tert-butyl-5-chloro-2-phenoxy) diphenylmethanetitanium dichloride, (η5-cyclopentadienyl)(3-phenyl-2-phenoxy) diphenylmethanetitanium dichloride, (η5-cyclopentadienyl)(3-tert-butyldimethylsilyl-5-methyl-2-phenoxy)diphenylmethanetitanium dichloride, (η5-cyclopentadienyl)(3-trimethylsilyl-5-methyl-2-phenoxy)diphenylmethanetitanium dichloride, (η5-2,3,4,5-tetramethylcyclopentadienyl)(2-phenoxy) methanetitanium dichloride, (η5-2,3,4,5-tetramethylcyclopentadienyl)(3,4-dimethyl-2-phenoxy)methanetitanium dichloride, (η5-2,3,4,5-tetramethylcyclopentadienyl)(3-tert-butyl-5-methyl-2-phenoxy)methanetitanium dichloride, (η5-2,3,4,5-tetramethylcyclopentadienyl)(3-tert-butyl-5-methoxy-2-phenoxy)methanetitanium dichloride, (η5-2,3,4,5-tetramethylcyclopentadienyl)(3-tert-butyl-2-phenoxy) methanetitanium dichloride, (η5-2,3,4,5-tetramethylcyclopentadienyl)(3-tert-butyl-5-chloro-2-phenoxy)methanetitanium dichloride, (η5-2,3,4,5-tetramethylcyclopentadienyl)(3-phenyl-2-phenoxy) methanetitanium dichloride, (η5- 2,3,4,5-tetramethylcyclopentadienyl)(3-tert-butyldimethylsilyl-5-methyl-2-phenoxy) methanetitanium dichloride, (η5-2,3,4,5-tetramethylcyclopentadienyl)(3-trimethylsilyl-5-methyl-2-phenoxy)methanetitanium dichloride, (η5-2,3,4,5-tetramethylcyclopentadienyl)(2-phenoxy) dimethylmethanetitanium dichloride, (η5-2,3,4,5- tetramethylcyclopentadienyl)(3,4-dimethyl-2-phenoxy)dimethylmethanetitanium dichloride, (η5-2,3,4,5-tetramethylcyclopentadienyl)(3-tert-butyl-5-methyl-2-phenoxy)dimethylmethanetitanium dichloride, (η5-2,3,4,5-tetramethylcyclopentadienyl)(3-tert-butyl-5-methoxy-2-phenoxy)dimethylmethanetitanium dichloride, (η5-2,3,4,5-tetramethylcyclopentadienyl)(3-tert-butyl-2-phenoxy)dimethylmethanetitanium dichloride, (η5-2,3,4,5-tetramethylcyclopentadienyl)(3-tert-butyl-5-chloro-2-phenoxy)dimethylmethanetitanium dichloride, (η5-2,3,4,5-tetramethylcyclopentadienyl)(3-phenyl-2-phenoxy)dimethylmethanetitanium dichloride, (η5-2,3,4,5-tetramethylcyclopentadienyl)(3-tert-butyldimethylsilyl-5-methyl-2-phenoxy)dimethylmethanetitanium dichloride, (η5-2,3,4,5-tetramethylcyclopentadienyl)(3-trimethylsilyl-5-methyl-2-phenoxy)dimethylmethanetitanium dichloride, (η5-2,3,4,5-tetramethylcyclopentadienyl)(2-phenoxy)diphenylmethanetitanium dichloride, (η5-2,3,4,5-tetramethylcyclopentadienyl)(3,4-dimethyl-2-phenoxy)diphenylmethanetitanium dichloride, (η5-2,3,4,5-tetramethylcyclopentadienyl)(3-tert-butyl-5-methyl-2-phenoxy)diphenylmethanetitanium dichloride, (η5-2,3,4,5-tetramethylcyclopentadienyl)(3-tert-butyl-5-methoxy-2-phenoxy)diphenylmethanetitanium dichloride, (η5-2,3,4,5-tetramethylcyclopentadienyl)(3-tert-butyl-2-phenoxy)diphenylmethanetitanium dichloride, (η5-2,3,4,5-tetramethylcyclopentadienyl)(3-tert-butyl-5-chloro-2-phenoxy)diphenylmethanetitanium dichloride, (η5-2,3,4,5-tetramethylcyclopentadienyl)(3-phenyl-2-phenoxy)diphenylmethanetitanium dichloride, (η5-2,3,4,5-tetramethylcyclopentadienyl)(3-tert-butyldimethylsilyl-5-methyl-2-phenoxy)diphenylmethanetitanium dichloride, (η5-2,3,4,5-tetramethylcyclopentadienyl)(3-trimethylsilyl-5-methyl-2-phenoxy)diphenylmethanetitanium dichloride, (η5-3-methylcyclopentadienyl)(2-phenoxy)methanetitanium dichloride, (η5-3-methylcyclopentadienyl)(3,4-dimethyl-2-phenoxy)methanetitanium dichloride, (η5-3-methylcyclopentadienyl)(3-tert-butyl-5-methyl-2-phenoxy)methanetitanium dichloride, (η5-3-methylcyclopentadienyl)(3-tert-butyl-5-methoxy-2-phenoxy)methanetitanium dichloride, (η5-3-methylcyclopentadienyl)(3-tert-butyl-2-phenoxy)methanetitanium dichloride, (η5-3-methylcyclopentadienyl)(3-tert-butyl-5-chloro-2-phenoxy)methanetitanium dichloride, (η5-3-methylcyclopentadienyl)(3-phenyl-2-phenoxy)methanetitanium dichloride, (η5-3-methylcyclopentadienyl)(3-tert-butyldimethylsilyl-5-methyl-2-phenoxy)methanetitanium dichloride, (η5-3-methylcyclopentadienyl)(3-trimethylsilyl-5-methyl-2-phenoxy)methanetitanium dichloride, (η5-3-methylcyclopentadienyl)(2-phenoxy)dimethylmethanetitanium dichloride, (η5-3-methylcyclopentadienyl)(3,4-dimethyl-2-phenoxy)dimethylmethanetitanium dichloride, (η5-3-methylcyclopentadienyl)(3-tert-butyl-5-methyl-2-phenoxy)dimethylmethanetitanium dichloride, (η5-3-methylcyclopentadienyl)(3-tert-butyl-5-methoxy-2-phenoxy)dimethylmethanetitanium dichloride, (η5-3-methylcyclopentadienyl)(3-tert-butyl-2-phenoxy)dimethylmethanetitanium dichloride, (η5-3-methylcyclopentadienyl)(3-tert-butyl-5-chloro-2-phenoxy)dimethylmethanetitanium dichloride, (η5-3-methylcyclopentadienyl)(3-phenyl-2-phenoxy)dimethylmethanetitanium dichloride, (η5-3-methylcyclopentadienyl)(3-tert-butyldimethylsilyl-5-methyl-2-phenoxy)dimethylmethanetitanium dichloride, (η5-3-methylcyclopentadienyl)(3-trimethylsilyl-5-methyl-2-phenoxy)dimethylmethanetitanium dichloride, (η5-3-methylcyclopentadienyl)(2-phenoxy)diphenylmathanetitanium dichloride, (η5-3-methylcyclopentadienyl)(3,4-dimethyl-2-phenoxy)diphenylmathanetitanium dichloride, (η5-3-methylcyclopentadienyl)(3-tert-butyl-5-methyl-2-phenoxy)diphenylmathanetitanium dichloride, (η5-3-methylcyclopentadienyl)(3-tert-butyl-5-methoxy-2-phenoxy)diphenylmathanetitanium dichloride, (η5-3-methylcyclopentadienyl)(3-tert-butyl- 2-phenoxy)diphenylmathanetitanium dichloride, (η5-3-methylcyclopentadienyl)(3-tert-butyl-5-chloro-2-phenoxy)diphenylmathanetitanium dichloride, (η5-3-methylcyclopentadienyl)(3-phenyl-2-phenoxy)diphenylmathanetitanium dichloride, (η5-3-methylcyclopentadienyl)(3-tert-butyldimethylsilyl-5-methyl-2-phenoxy)diphenylmathanetitanium dichloride, (η5-3-methylcyclopentadienyl)(3-trimethylsilyl-5-methyl-2-phenoxy)diphenylmathanetitanium dichloride, (η5-3-tert-butylcyclopentadienyl)(2-phenoxy)methanetitanium dichloride, (η5-3-tert-butylcyclopentadienyl)(3,4-dimethyl-2-phenoxy)methanetitanium dichloride, (η5- 3-tert-butylcyclopentadienyl)(3-tert-butyl-5-methyl-2-phenoxy)methanetitanium dichloride, (η5-3-tert-butylcyclopentadienyl)(3-tert-butyl-5-methoxy-2-phenoxy)methanetitanium dichloride, (η5-3-tert-butylcyclopentadienyl)(3-tert-butyl-2-phenoxy)methanetitanium dichloride, (η5-3-tert-butylcyclopentadienyl)(3-tert-butyl-5-chloro-2-phenoxy)methanetitanium dichloride, (η5-3-tert-butylcyclopentadienyl)(3-phenyl-2-phenoxy)methanetitanium dichloride, (η5-3-tert-butylcyclopentadienyl)(3-tert-butyldimethylsilyl-5-methyl-2-phenoxy)methanetitanium dichloride, (η5-3-tert-butylcyclopentadienyl)(3-trimethylsilyl-5-methyl-2-phenoxy)methanetitanium dichloride, (η5-3-tert-butylcyclopentadienyl)(2-phenoxy)dimethylmethanetitanium dichloride, (η5-3-tert-butylcyclopentadienyl)(3,4-dimethyl-2-phenoxy)dimethylmethanetitanium dichloride, (η5-3-tert-butylcyclopentadienyl)(3-tert-butyl-5-methyl-2-phenoxy)dimethylmethanetitanium dichloride, (η5-3-tert-butylcyclopentadienyl)(3-tert-butyl-5-methoxy-2-phenoxy)dimethylmethanetitanium dichloride, (η5-3-tert-butylcyclopentadienyl)(3-tert-butyl-2-phenoxy)dimethylmethanetitanium dichloride, (η5-3-tert-butylcyclopentadienyl)(3-tert-butyl-5-chloro-2-phenoxy)dimethylmethanetitanium dichloride, (η5-3-tert-butylcyclopentadienyl)(3-phenyl-2-phenoxy)dimethylmethanetitanium dichloride, (η5-3-tert-butylcyclopentadienyl)(3-tert-butyldimethylsilyl-5-methyl-2-phenoxy)dimethylmethanetitanium dichloride, (η5-3-tert-butylcyclopentadienyl)(3-trimethylsilyl-5-methyl-2-phenoxy)dimethylmethanetitanium dichloride, (η5-3-tert-butylcyclopentadienyl)(2-phenoxy)diphenylmethanetitanium dichloride, (η5-3-tertbutylcyclopentadienyl)(3,4-dimethyl-2-phenoxy) diphenylmethanetitanium dichloride, (η5-3-tert-butylcyclopentadienyl)(3-tert-butyl-5-methyl-2-phenoxy)diphenylmethanetitanium dichloride, (η5-3-tert-butylcyclopentadienyl)(3-tert-butyl-5-methoxy-2-phenoxy)diphenylmethanetitanium dichloride, (η5-3-tert-butylcyclopentadienyl)(3-tert-butyl-2-phenoxy) diphenylmethanetitanium dichloride, (η5-3-tert-butylcyclopentadienyl)(3-tert-butyl-5-chloro-2-phenoxy)diphenylmethanetitanium dichloride, (η5-3-tert-butylcyclopentadienyl)(3-phenyl-2-phenoxy) diphenylmethanetitanium dichloride, (η5-3-tert-butylcyclopentadienyl)(3-tert-butyldimethylsilyl-5-methyl-2-phenoxy)diphenylmethanetitanium dichloride, (η5-3-tert-butylcyclopentadienyl)(3-trimethylsilyl-5-methyl-2-phenoxy) diphenylmethanetitanium dichloride, and compounds obtained by substituting η5-2-methylcyclopentadienyl, η5-2-tert-butylcyclopentadienyl, η5-2-n-butylcyclopentadienyl, η5-3-n-butylcyclopentadienyl, η5-indenyl, η5-fluorenyl for η5-cyclopentadienyl, and substituting dibromide, diiodide for dichloride on the above-described compounds.

Examples of the halogenated titanium complex (II) in which A represents a silicon atom include (η5-cyclopentadienyl)(2-phenoxy)dimethylsilanetitanium dichloride, (η5-cyclopentadienyl)(3,4-dimethyl-2-phenoxy) dimethylsilanetitanium dichloride, (η5-cyclopentadienyl) (3-tert-butyl-5-methyl-2-phenoxy)dimethylsilanetitanium dichloride, (η5-cyclopentadienyl)(3-tert-butyl-5-methoxy-2-phenoxy)dimethylsilanetitanium dichloride, (η5-cyclopentadienyl)(3-tert-butyl-2-phenoxy) dimethylsilanetitanium dichloride, (η5-cyclopentadienyl) (3-tert-butyl-5-chloro-2-phenoxy)dimethylsilanetitanium dichloride, (η-cyclopentadienyl)(3-phenyl-2-phenoxy) dimethylsilanetitanium dichloride, (η5-cyclopentadienyl) (3-tert-butyldimethylsilyl-5-methyl-2-phenoxy) dimethylsilanetitanium dichloride, (η5-cyclopentadienyl) (3-trimethylsilyl-5-methyl-2-phenoxy) dimethylsilanetitanium dichloride, (η5-cyclopentadienyl)(2-phenoxy) diphenylsilanetitanium dichloride, (η5-cyclopentadienyl)(3,4-dimethyl-2-phenoxy) diphenylsilanetitanium dichloride, (η5-cyclopentadienyl)(3-tert-butyl-5-methyl-2-phenoxy) diphenylsilanetitanium dichloride, (η5-cyclopentadienyl)(3-tert-butyl-5-methoxy-2-phenoxy) diphenylsilanetitanium dichloride, (η5-cyclopentadienyl)(3-tert-butyl-2-phenoxy) diphenylsilanetitanium dichloride, (η5-cyclopentadienyl)(3-tert-butyl-5-chloro-2-phenoxy) diphenylsilanetitanium dichloride, (η5-cyclopentadienyl)(3-phenyl-2-phenoxy) diphenylsilanetitanium dichloride, (η5-cyclopentadienyl)(3-tert-butyldimethylsilyl-5-methyl-2-phenoxy)diphenylsilanetitanium dichloride, (η5-cyclopentadienyl)(3-trimethylsilyl-5-methyl-2-phenoxy)diphenylsilanetitanium dichloride, (η5-2,3,4,5-tetramethylcyclopentadienyl)(2-phenoxy) dimethylsilanetitanium dichloride, (η5-2,3,4,5-tetramethylcyclopentadienyl)(3,4-dimethyl-2-phenoxy)dimethylsilanetitanium dichloride, (η5-2,3,4,5-tetramethylcyclopentadienyl)(3-tert-butyl-5-methyl-2-phenoxy)dimethylsilanetitanium dichloride, (η5-2,3,4,5-tetramethylcyclopentadienyl)(3-tert-butyl-5-methoxy-2-phenoxy)dimethylsilanetitanium dichloride, (η5-2,3,4,5-tetramethylcyclopentadienyl) (3-tert-butyl-2-phenoxy)dimethylsilanetitanium dichloride, (η5-2,3,4,5-tetramethylcyclopentadienyl) (3-tert-butyl-5-chloro-2-phenoxy) dimethylsilanetitanium dichloride, (η5-2,3,4,5-tetramethylcyclopentadienyl)(3-phenyl-2-phenoxy) dimethylsilanetitanium dichloride, (η5-2,3,4,5-tetramethylcyclopentadienyl)(3-tert-butyldimethylsilyl-5-methyl-2-phenoxy) dimethylsilanetitanium dichloride, (η5-2,3,4,5-tetramethylcyclopentadienyl)(3-trimethylsilyl-5-methyl-2-phenoxy)dimethylsilanetitanium dichloride, (η5-2,3,4,5-tetramethylcyclopentadienyl)(2-phenoxy) diphenylsilanetitanium dichloride, (η5-2,3,4,5-tetramethylcyclopentadienyl)(3,4-dimethyl-2-phenoxy)diphenylsilanetitanium dichloride, (η5-2,3,4, 5-tetramethylcyclopentadienyl)(3-tert-butyl-5-methyl-2-phenoxy)diphenylsilanetitanium dichloride, (η5-2,3,4,5-tetramethylcyclopentadienyl)(3-tert-butyl-5-methoxy-2-phenoxy)diphenylsilanetitanium dichloride, (η5-2,3,4,5-tetramethylcyclopentadienyl) (3-tert-butyl-2-phenoxy)diphenylsilanetitanium dichloride, (η5-2,3,4,5-tetramethylcyclopentadienyl) (3-tert-butyl-5-chloro-2-phenoxy) diphenylsilanetitanium dichloride, (η5-2,3,4,5-tetramethylcyclopentadienyl)(3-phenyl-2-phenoxy) diphenylsilanetitanium dichloride, (η5- 2,3,4,5-tetramethylcyclopentadienyl)(3-tert-butyldimethylsilyl-5-methyl-2-phenoxy) diphenylsilanetitanium dichloride, (η5-2,3,4,5-tetramethylcyclopentadienyl)(3-trimethylsilyl-5-methyl-2-phenoxy)diphenylsilanetitanium dichloride, (η7 5-indenyl)(2-phenoxy)dimethylsilanetitanium dichloride, (η5-indenyl)(3,4-dimethyl-2-phenoxy) dimethylsilanetitanium dichloride, (η5-indenyl)(3-tert-butyl-5-methyl-2-phenoxy)dimethylsilanetitanium dichloride, (η5-indenyl)(3-tert-butyl-5-methoxy-2-phenoxy)dimethylsilanetitanium dichloride, (η5-indenyl)(3-tert-butyl-2-phenoxy) dimethylsilanetitanium dichloride, (η5-indenyl)(3-tert-butyl-5-chloro-2-phenoxy)dimethylsilanetitanium dichloride, (η5-indenyl)(3-phenyl-2-phenoxy) dimethylsilanetitanium dichloride, (η5-indenyl)(3-tert-butyldimethylsilyl-5-methyl-2-phenoxy) dimethylsilanetitanium dichloride, (η5-indenyl)(3-trimethylsilyl-5-methyl-2-phenoxy) dimethylsilanetitanium dichloride, (η5-indenyl)(2-phenoxy)diphenylsilanetitanium dichloride, (η5-indenyl)(3,4-dimethyl-2-phenoxy) diphenylsilanetitanium dichloride, (η5-indenyl)(3-tert-butyl-5-methyl-2-phenoxy)diphenylsilanetitanium dichloride, (η5-indenyl)(3-tert-butyl-5-methoxy-2-phenoxy)diphenylsilanetitanium dichloride, (η5-indenyl)(3-tert-butyl-2-phenoxy) diphenylsilanetitanium dichloride, (η5-indenyl)(3-tert-butyl-5-chloro-2-phenoxy)diphenylsilanetitanium dichloride, (η5-indenyl)(3-phenyl-2-phenoxy) diphenylsilanetitanium dichloride, (η5-indenyl)(3-tert-butyldimethylsilyl-5-methyl-2-phenoxy) diphenylsilanetitanium dichloride, (η5-indenyl)(3-trimethylsilyl-5-methyl-2-phenoxy) diphenylsilanetitanium dichloride, (η5-3-tert-butylcyclopentadienyl)(2-phenoxy) dimethylsilanetitanium dichloride, (η5-3-tert-butylcyclopentadienyl)(3,4-dimethyl-2-phenoxy) dimethylsilanetitanium dichloride, (η5-3-tert-butylcyclopentadienyl)(3-tert-butyl-5-methyl-2-phenoxy)dimethylsilanetitanium dichloride, (η5-3-tertbutylcyclopentadienyl)(3-tert-butyl-5-methoxy-2-phenoxy)dimethylsilanetitanium dichloride, (η5-3-tert-butylcyclopentadienyl)(3-tert-butyl-2-phenoxy) dimethylsilanetitanium dichloride, (η5-3-tert-butylcyclopentadienyl)(3-tert-butyl-5-chloro-2-phenoxy)dimethylsilanetitanium dichloride, (η5-3-tert-butylcyclopentadienyl)(3-phenyl-2-phenoxy) dimethylsilanetitanium dichloride, (η5-3-tert-butylcyclopentadienyl)(3-tert-butyldimethylsilyl-5-methyl-2-phenoxy)dimethylsilanetitanium dichloride, (η5-3-tert-butylcyclopentadienyl)(3-trimethylsilyl-5-methyl-2-phenoxy)dimethylsilanetitanium dichloride, (η5-3-tert-butylcyclopentadienyl)(2-phenoxy) diphenylsilanetitanium dichloride, (η5-3-tert-butylcyclopentadienyl)(3,4-dimethyl-2-phenoxy) diphenylsilanetitanium dichloride, (η5-3-tert-butylcyclopentadienyl)(3-tert-butyl-5-methyl-2-phenoxy)diphenylsilanetitanium dichloride, (η5-3-tert-butylcyclopentadienyl)(3-tert-butyl-5-methoxy-2-phenoxy)diphenylsilanetitanium dichloride, (η5-3-tert-butylcyclopentadienyl)(3-tert-butyl-2-phenoxy) diphenylsilanetitanium dichloride, (η5-3-tert-butylcyclopentadienyl)(3-tert-butyl-5-chloro-2-phenoxy)diphenylsilanetitanium dichloride, (η5-3-tert-butylcyclopentadienyl)(3-phenyl-2-phenoxy) diphenylsilanetitanium dichloride, (η5-3-tert-butylcyclopentadienyl)(3-tert-butyldimethylsilyl-5-methyl-2-phenoxy)diphenylsilanetitanium dichloride, (η5-3-tert-butylcyclopentadienyl)(3-trimethylsilyl-5-methyl-2-phenoxy)diphenylsilanetitanium dichloride, and compounds obtained by substituting η5-2-methylcyclopentadienyl, η5-3-methylcyclopentadienyl, η5-2-tert-butylcyclopentadienyl, η5-2-n-butylcyclopentadienyl, η5-3-n-butylcyclopentadienyl, η5-fluorenyl for η5-cyclopentadienyl, and substituting bromide, iodide for chloride on the above-described compounds.

Examples of the alkali metal alkoxides of the formula (III) include sodium methoxide, sodium ethoxide, sodium n-propoxide, sodium isopropoxide, sodium n-butoxide, sodium sec-butoxide, sodium tert-butoxide, sodium n-pentoxide, sodium neopentoxide, sodium methoxyethoxide, sodium ethoxyethoxide, sodiumbenzyloxide, sodiuml-phenylethoxide, and alkali metal alkoxides derived from monools in which sodium is substituted by lithium, potassium; disodiumethyilene dioxide, disodiummethylethylene dioxide, disodium 1,2-dimethylethylene dioxide, disodiumtetramethylethylene dioxide, disodiumphenyethylene dioxide, disodiuml,2-diphenylethylene dioxide, disodiumtetraphenylethylene dioxide, disodiumcyclopentane-1,2-dioxide, disodiumcyclohexane-1,2-dioxide, disodiumpropylene-1,3-dioxide, disodium 1,3-dimethylpropylene-1,3-dioxide, disodiuml,3-diphenylpropylene-1,3-dioxide, and alkali metal alkoxides derived from diols in which sodium is optionally substituted by lithium, potassium, and all steric and optical isomers thereof.

These are not only commercially available but also can be produced by reacting an alcohol compound with the alkali metal compounds.

Examples of the alcohols of the formula (III') include monools such as methanol, ethanol, n-propanol, isopropanol, n-butanol, sec-butanol, tert-butanol, n-pentanol, neopentyl alcohol, ethylene glycol monomethyl ether, ethylene glycol monoethyl ether, benzyl alcohol, 1-phenylethanol and the like, diols such as ethylene glycol, propylene glycol, 2,3-butanediol, tetramethylethylene glycol, phenylethylene glycol, hydrobenzoin, tetraphenylethylene glycol, cyclopentane-1,2-diol, cyclohexane-1,2-diol, 1,3-propanediol, 2,4-pentanediol, 1,3-diphenyl-1,3-propanediol, tartaric acid and the like, and all steric and optical isomers thereof.

The amine compound is used as a dehydrohalogenating agent and is not particularly restricted, and examples thereof include primary amines such as aniline, chloroaniline, bromoaniline, fluoroaniline, toluidine, anisidine, naphthylamine, benzylamine, propylamine, butylamine, pentylamine and the like, secondary amines such as N-methylaniline, N-ethylaniline, diphenylamine, N-methylchloroaniline, N-methylbromoaniline, N-methylfluoroaniline, pyrrolidine, morpholine, piperidine and the like, tertiary amines such as trimethylamine, triethylamine, diiosopropylethylamine, N,N-dimethylaniline, N,N-dimethylchloroaniline, N,N-dimethylbromoaniline, N,N-dimethylfluoroaniline, N-methylpyrrolidine, N-methylmorpholine, N-methylpiperidine, 1,4-diazabicyclo[2,2,2]octane, 1,5-diazabicyclo[4.3.0]non-5-ene, 1,8-diazabicyclo[5,4,0] undec-7-ene and the like, and piridines such as piridine, N,N-dimethylaminopiridine, picoline, pipecoline, and the like, Examples of the alkali metal aryloxides (V) include lithium phenoxide, lithium 2-methylphenoxide, lithium 3-methylphenoxide, lithium 4-methylphenoxide, lithium 2,3-dimethylphenoxide, lithium 2,4-dimethylphenoxide, lithium 2,5-dimethylphenoxide, lithium 2,6-dimethylphenoxide, lithium 3,4-dimethylphenoxide, lithium 2,3,4-trimethylphenoxide, lithium 2,3,5-trimethylphenoxide, lithium 2,3,6-trimethylphenoxide, lithium 3,4,5-trimethylphenoxide, lithium 2,4,6-trimethylphenoxide, lithium 2,3,4,5-tetramethylphenoxide, lithium 2,3,4,6-tetramethylphenoxide, 2,3,5,6-tetramethylphenoxide, lithium pentamethyiphenoxide, lithium ethylphenoxide, lithium n-propylphenoxide, lithium isopropylphenoxide, lithium n-but ylphenoxide, lithium sec-butylphenoxide, litihum tert-butylphenoxide, lithium n-pentylphenoxide, lithium neopentylphenoxide, lithium n-hexylphenoxide, lithium n-otylphenoxide, lithiumn-decylphenoxide, lithium n-dodecylphenoxide, lithium n-tetradecylphenoxide, lithium naphthyloxide, lithium anthracenyloxide; and compounds obtained by substituting sodium, potassium for lithium on these compounds; further, alkali metal haloaryloxides obtained by substitution with halogen such as fluorine, chlorine, bromine and the like on these compounds; and alkali metal alkoxyaryloxides obtained by optional substitution by a methoxy group, ethoxy group, n-propoxy group, isopropoxy group, n-butoxy group, sec-butoxy group, tert-butoxy group and the like for a halogen atom on the above-described haloalkyl groups; alkali metal cyanoaryloxides obatined by substitution by a cyano group for the halogen atom of the haloaryloxides above; and alkali metal nitroaryloxides obatined by substitution by a nitro group for the halogen atom of the haloaryloxides above; and preferable examples thereof include lithium phenoxide, litium 4-methylphenoxide, lithium 2,4, 6-terimethylphenoxide, sodium phenoxide, sodium 4-methylphenoxide and sodium 2,4,6-trimethylphenoxide.

Examples of the compound in which substituents Ars bond mutually to form a ring include dilithium 1,1'-biphenyl-2,2'-dioxide, dilithium 1,1'-biphenyl-4,4'-dimethyl-2,2'-dioxide, dilithium 1,1'-biphenyl-6,6'-dimethyl-2,2'-dioxide, dilithium 1,1'-biphenyl-3,3'-di-tert-butyl-2,2'-dioxide, dilithium 1,1'-bibinaphthyl-2,2'-dioxide, dilithium 1,1'-bibinaphthyl-3,3-bis(trimethylsilyl)-2,2'- dioxide, dilithium 1,1'-thiobiphenyl-2,2'-dioxide, dilithium 1,1'-thiobiphenyl-5,5'-dimethyl-2,2'-dioxide, dilithium 1,1'-thiobiphenyl-3,3'-di-tert-butyl-5,5'-dimethyl-2,2'-dioxide, dilithium 1,1'-methylenebiphenyl-2,2'-dioxide, dilithium 1,1'-methylenebiphenyl-5,5'-dimethyl-2,2'-dioxide, dilithium 1,1'-methylenebiphenyl-3,3'-di-tert-butyl-5,5'-dimethyl-2,2'-dioxide, dilithium 1,1'-phenylphosphinobiphenyl-2,2'-dioxide, dilithium 1,1'-phenylphosphinobiphenyl-5,5'-dimethyl-2,2'-dioxide, dilithium 1,1'-phenylphosphinobiphenyl-3,3'-di-tert-butyl-5,5'-dimethyl-2,2'-dioxide, and alkali metal biaryloxides derived from biarylhydroxides in which lithium is substituted by potassium, sodium.

These are not only commercially available but also can be produced by reacting the arylhydroxide compound with the alkali metal compounds.

Examples of the alkali metal amides (VII) include lithium dimethylamide, lithium diethylamide, lithium di-n-propylamide, lithium diisopropylamide, lithium di-n-butylamide, lithium di-n-pentylamide, lithium dineopentylamide, lithium di-n-octylamide, lithium dicyclohexylamide, lithium dicyclopentylamide, lithium dibenzylamide, lithium ditolylmethylamide, lithium N-methylanilide, lithium N-ethylanilide, lithium diphenylamide, lithium ditolylamide, lithium pyrrolidide, lithium 2,5-dimethylpyrrolide, lithium 2,2,5,5-tetramethylpyrrolide, lithium piperidide, lithium 2,6-dimethylpiperidide, lithium 2,2,6,6-tetramethylpiperidide, lithium azetidide, and compounds obtained by substituting sodium, potassium for lithium on the above-described compounds.

These are not only commercially available but also can be produced by reacting an amine compound with the alkali metal compounds.

Production of an alkoxytitanium complex is not particularly restricted, and Method A can be preferably conducted by reacting the halogenated titanium complex (II) with the alkali metal alkoxides (III) and Method B can be preferably conducted by reacting the halogenated titanium complex (II) with the alcohols (III'), optionally in the presene of an amine, respectively under inert atmosphere such as nitrogen, argon and the like in the presence of a solvent.

Charge ratio of the alkali metal alkoxides (III) to the halogenated titanium complex (II) in Method A is usually from 0.5 to 10-fold by mol, preferably from 0.8 to 3-fold by mol.

Charge ratio of the alcohols (III') to the halogenated titanium complex (II) in Method B is usually from 0.5 to 10-fold by mol, preferably from 0.8 to 3-fold by mol, and charge ratio of an amine to the halogenated titanium complex (II) in Method B is usually from 0.5 to 5-fold by mol, preferably from 0.8 to 3-fold by mol.

The solvent is not particularly restricted, examples thereof include aliphatic hydrocarbons such as pentane, hexane, heptane, octane, decane and the like, aromatic hydrocarbons such as benzene, toluene, xylene, mesitylene and the like, aliphatic halogenated hydrocarbons such as dichloromethane, chloroform, dichloroethane and the like, aromatic halogenated hydrocarbons such as monochlorobenzene, dichlorobenzene and the like, ethers such as diethyl ether, dibutyl ether, methyl t-butyl ether, tetrahydrofuran and the like, and alcohol corresponding to the alkali metal alkoxides (III), and mixtures thereof.

The amount used thereof is usually from 1 to 200-fold by weight, preferably from 3 to 30-fold by weight based on the halogenated titanium complex (II) in both Method A and Method B.

Reaction method for producing an aryloxytitanium complex is not particularly restricted, and it can be preferably conducted by reacting the halogenated titanium complex (II) with the alkali metal aryloxides (V) under inert atmosphere such as nitrogen, argon and the like in the presence of a solvent.

Charge ratio of the alkali metal aryloxides (V) to the halogenated titanium complex (II) is usually from 0.5 to 10-fold by mol, preferably from 0.8 to 3-fold by mol.

The solvent is not particularly restricted, examples thereof include aliphatic hydrocarbons such as pentane, hexane, heptane, octane, decane and the like, aromatic hydrocarbons such as benzene, toluene, xylene, mesitylene and the like, aliphatic halogenated hydrocarbons such as dichloromethane, chloroform, dichloroethane and the like, aromatic halogenated hydrocarbons such as monochlorobenzene, dichlorobenzene and the like, ethers such as diethyl ether, dibutyl ether, methyl t-butyl ether, tetrahydrofuran and the like, and mixtures thereof.

The amount used thereof is usually from 1 to 200-fold by weight, preferably from 3 to 30-fold by weight based on the halogenated titanium complex (II).

Reaction method for producing an aminotitanium complex is not particularly restricted, and it can be preferably conducted by reacting the halogenated titanium complex (II) with the alkali metal amides (VII) under inert atmosphere such as nitrogen, argon and the like in the presence of a solvent.

Use ratio by mol of the alkali metal amides (VII) to the halogenated titanium complex (II) is usually from 0.5 to 10-fold by mol, preferably from 0.8 to 3-fold by mol.

The solvent is not particularly restricted, examples thereof include aliphatic hydrocarbons such as pentane, hexane, heptane, octane, decane and the like, aromatic hydrocarbons such as benzene, toluene, xylene, mesitylene and the like, aliphatic halogenated hydrocarbons such as dichloromethane, chloroform, dichloroethane and the like, aromatic halogenated hydrocarbons such as monochlorobenzene, dichlorobenzene and the like, ethers such as diethyl ether, dibutyl ether, methyl t-butyl ether, tetrahydrofuran and the like.

The amount used thereof is usually from 1 to 200-fold by weight, preferably from 3 to 30-fold by weight based on the halogenated titanum complex (II).

The reaction temperature is usually from −100° C. to the boiling point of a solvent, and preferably from −80° C. to 30° C.

After the reaction, the alkoxytitanium complex (I), aryloxytitanium complex (IV) or aminotitanium complex (VI) can be obtained by, for example, removing insoluble solids and distilling off a solvent. If necessary, the product can be purified by a conventional method such as re-crystallization, sublimation and the like. Effect of the Invention According to the present invention, an alkoxytitanium complex (I), an aryloxytitanium complex (IV) or an aminotitanium complex (VI) can be produced industrially advantageously.

EXAMPLE

The following examples further illustrate the present invention in detail, but do not limit the present invention.

Example 1

Synthesis of (η5-tetramethylcyclopentadienyl)(3-tert-butyl-5-methyl-2-phenoxy) dimethylsilanetitanium dimethoxide In schloenk tube, 0.131 g (4.1 mmol) of methanol was dissolved in 10 ml of anhydrous ether, and to this solution was added 1.05 M methyllithium ether solution (3.9 ml, 4.1 mmol) dropwise at −78° C. The mixture was heated to 20° C., production of lithium methoxide was confirmed by checking completion of gas evolution, and the mixture was cooled again to −78° C. A suspension of 0.919 g (2.0 mmol) of (η5-tetramethylcyclopentadienyl)(3-tert-butyl-5-methyl-2-phenoxy)dimethylsilanetitanium dichloride in 20 ml of anhydrous ether previously prepared in another schloenk tube was transferred into the above-described reaction solution, then, the mixture was allowed to warm to room temperature gradually. The reaction solution was concentrated, then, to this was added 20 ml of toluene, and insoluble components were filtrated. The filtrate was concentrated to obtain (η5-tetramethylcyclopentadienyl)(3-tert-butyl-5-methyl-2-phenoxy)dimethylsilanetitanium dimethoxide as a yellow crystal (0.86 g, 95%).

$^1$H NMR (270 MHz, $C_6D_6$) δ 7.26 (m, 2H), 4.13 (s, 6H), 2.33 (s, 3H), 1.97 (s, 6H), 1.89 (s, 6H), 1.59 (s, 9H), 0.55 (s, 6H)

Example 2

Synthesis of (η5-tetramethylcyclopentadienyl)(3-tert-butyl-5-methyl-2-phenoxy) dimethylsilanetitanium dimethoxide In schloenk tube, 4.59 g (10.0 mmol) of (η5-tetramethylcyclopentadienyl)(3-tert-butyl-5-methyl-2-phenoxy)dimethylsilanetitanium dichloride was suspended in 42 ml of toluene, to this was added 28% sodium methylate methanol solution (4.05 g, 21.0 mmol) dropwise at −78° C., then, the mixture was allowed to warm to room temperature gradually. The reaction solution was concentrated, then, to this was added 50 ml of toluene, and insoluble components were filtrated. The filtrate was concentrated to obtain (η5-tetramethylcyclopentadienyl)(3-tert-butyl-5-methyl-2-phenoxy)dimethylsilanetitanium dimethoxide as a yellow crystal (4.33 g, 96%).

Example 3

Synthesis of (η5-tetramethylcyclopentadienyl)(3-tert-butyl-5-methyl-2-phenoxy) dimethylsilanetitanium dimethoxide In schloenk tube, 0.40 g (12.5 mmol) of methanol and 2.53 g (25.0 mmol) of triethylamine were dissolved in 30 ml of toluene, to this was added 2.30 g (5.0 mmol) of (η5-tetramethylcyclopentadienyl)(3-tert-butyl-5-methyl-2-phenoxy)dimethylsilanetitanium dichloride portionwise at −78° C. with stirring, then, the mixture was allowed to warm to room temperature and stirred for 10 hours. Insoluble components were filtrated, and the residue was washed with 20 ml of toluene. The filtrate was concentrated to obtain (η5-tetramethylcyclopentadienyl)(3-tert-butyl-5-methyl-2-phenoxy)dimethylsilanetitanium dimethoxide as a yellow crystal (1.74 g, 80%).

Example 4

Synthesis of (η5-tetramethylcyclopentadienyl)(3-tert-butyl-5-methyl-2-phenoxy) dimethylsilanetitanium diisopropoxide In schloenk tube, 0.246 g (4.1 mmol) of isopropanol was dissolved in 10 ml of anhydrous ether, and to this solution was added 1.05 M methyllithium ether solution (3.9 ml, 4.1 mmol) dropwise at −78° C. The mixture was heated to 20° C., production of lithium isopropoxide was confirmed by checking completion of gas evolution, and the mixture was cooled again to −78° C. A suspension of 0.919 g (2.0 mmol) of (η5-tetramethylcyclopentadienyl)(3-tert-butyl-5-methyl-2-phenoxy)dimethylsilanetitanium dichloride in 20 ml of anhydrous ether previously prepared in another schloenk tube was transferred into the above-described reaction solution, then, the mixture was allowed to warm to room temperature gradually. The reaction solution was concentrated, then, to this was added 20 ml of toluene, and insoluble components were filtrated. The filtrate was concentrated to obtain (η5-tetramethylcyclopentadienyl)(3-tert-butyl-5-methyl-2-phenoxy)dimethylsilanetitanium diisopropoxide as a yellow crystal (0.98 g, 96%).

$^1$H NMR (270 MHz, $C_6D_6$) δ 7.29 (m, 2H), 4.75 (m, 2H), 2.31 (s, 3H), 2.02 (s, 6H), 1.93 (s, 6H), 1.58 (s, 9H), 1.18 (m, 12H), 0.60 (s, 6H)

Example 5

Synthesis of (η5-tetramethylcyclopentadienyl)(3-tert-butyl-5-methyl-2-phenoxy) dimethylsilanetitanium di-t-butoxide In schloenk tube, 0.55 g (1.2 mmol) of (η5-tetramethylcyclopentadienyl)(3-tert-butyl-5-methyl-2-phenoxy)dimethylsilanetitanium dichloride was suspended in 3 ml of toluene, to this was added 0.24 g (2.5 mmol) of t-butoxysodium at 0° C. The mixture was heated to 20° C., stirred for 1 hour, then, refluxed for 8 hours. After completion of the reaction, the mixture was cooled to room temperature, and insoluble components were removed by filtration. The filtrate was concentrated to obtain (η5-tetramethylcyclopentadienyl)(3-tert-butyl-5-methyl-2-phenoxy)dimethylsilanetitanium di-t-butoxide as a yellow crystal (0.49 g, 77%).

$^1$H NMR (270 MHz, $C_6D_6$) δ 7.28 (d, 1H), 7.16 (d, 1H), 2.32 (s, 3H), 2.05 (s, 6H), 1.97 (s, 6H), 1.59 (s, 9H), 1.35 (s, 18H), 0.64 (s, 6H)

Example 6

Synthesis of (η5-tetramethylcyclopentadienyl)(3-tert-butyl-5-methyl-2-phenoxy) dimethylsilanetitanium (ethylene dioxide)

In schloenk tube, ethylene glycol (4.26 g, 68.6 mmol) was dissolved in 10 ml of anhydrous ether, and to this solution was added 1.05 M methyllithium ether solution (3.9 ml, 4.1 mmol) dropwise at −78° C. The mixture was heated to 20° C., production of dilithiumethylene dioxide was confirmed by checking completion of gas evolution, and the mixture was cooled again to −78° C. A suspension of (η5-tetramethylcyclopentadienyl)(3-tert-butyl-5-methyl-2-phenoxy)dimethylsilanetitanium dichloride (30.0 g, 65.3 mmol) in 100 ml of anhydrous ether previously prepared in another schloenk tube was transferred into the above-described reaction solution, then, the mixture was allowed to warm to room temperature gradually. The reaction solution was concentrated, then, to this was added 200 ml of toluene, the resulting mixture was stirred for 2 hours at 100° C., then insoluble components were filtrated. The filtrate was concentrated, and recrystallized from toluene to obtain (η5-tetramethylcyclopentadienyl)(3-tert-butyl-5-methyl-2-phenoxy)dimethylsilanetitanium (ethylene dioxide) as a yellow crystal (8.51 g, 28%).

$^1$H NMR (270 MHz, $C6D_6$) δ 7.31 (1H), 7.28 (1H), 4.54 (2H), 4.16 (2H), 2.35 (s, 3H), 2.25 (s, 3H), 2.08 (s, 3H), 1.85 (s, 3H), 1.75 (s, 3H), 1.63 (s, 9H), 0.78 (s, 3H), 0.55 (s, 3H)

Example 7

Synthesis of (η5-tetramethylcyclopentadienyl)(3-tert-butyl-5-methyl-2-phenoxy)dimethylsilanetitanium methoxyethoxide In schloenk tube, ethylene glycol monomethyl ether (1.56 g, 20.5 mmol) was dissolved in 50 ml of anhydrous ether, and to this solution was added 1.05 M methyllithium ether solution (19.5 ml, 20.5 mmol) dropwise at −78° C. The mixture was heated to 20° C., production of lithium methoxyethoxide was confirmed by checking completion of gas evolution, and the mixture was cooled again to −78° C. A suspension of (η5-tetramethylcyclopentadienyl)(3-tert-butyl-5-methyl-2-phenoxy)dimethylsilanetitanium dichloride (4.59 g, 10.0 mmol) in 30 ml of anhydrous ether previously prepared in another schloenk tube was transferred into the above-described reaction solution, then, the mixture was allowed to warm to room temperature gradually. The reaction solution was concentrated, then, to this was added 20 ml of toluene, and insoluble components were filtrated. The filtrate was concentrated, and recrystallized from hexane to obtain (η5-tetramethylcyclopentadienyl)(3-tert-butyl-5-methyl-2-phenoxy)dimethylsilanetitanium methoxyethoxide as a yellow crystal (2.18 g, 40%).

$^1$H NMR (270 MHz, $C_6D_6$) δ 7.28 (2H), 4.48 (4H), 3.36 (4H), 3.18 (s, 6H), 2.32 (s, 3H), 2.05 (s, 12H), 1.55 (s, 9H), 0.60 (s, 6H)

Example 8

Synthesis of (η5-tetramethylcyclopentadienyl)(3-tert-butyl-5-methyl-2-phenoxy)dimethylsilanetitanium ((+)-1,2-diphenylethylene-1,2-dioxide)

In schloenk tube, 0.64 g (3.0 mmol) of (+) -hydrobenzoin and 1.01 g (10.0 mmol) of triethylamine were dissolved in 30 ml of toluene, to this was added 1.38 g (3.0 mmol) of (η5-tetramethylcyclopentadienyl)(3-tert-butyl-5-methyl-2-phenoxy)dimethylsilanetitanium dichloride portionwise at −78° C. with stirring, then, the mixture was allowed to warm to room temperature and stirred for 10 hours. Insoluble components were filtrated, and the residue was washed with 20 ml of toluene. The filtrate was concentrated to obtain (η5-tetramethylcyclopentadienyl)(3-tert-butyl-5-methyl-2-phenoxy)dimethylsilanetitanium ((+) -1,2-diphenylethylene-1,2-dioxide) as a yellow crystal (1.60 g, 89%).

$^1$H NMR (270 MHz, $C_6D_6$) δ 7.45–7.03 (10H), 6.93 (1H), 6.45 (1H), 2.45 (s, 3H), 2.33 (s, 3H), 2.30 (s, 2H), 2.16 (2, 3H), 2.06 (s, 3H), 1.95 (s, 3H), 1.75 (s, 9H), 0.58 (s, 3H), 0.55 (s, 3H)

Example 9

Synthesis of (η5-tetramethylcyclopentadienyl)(3-tert-butyl-5-methyl-2-phenoxy)dimethylsilanetitanium diphenoxide In schloenk tube, 1.976 g (21 mmol) of phenol was dissolved in 30 ml of toluene, and to this solution was added 1.60 M n-butyllithium hexane solution (13.1 ml, 21 mmol) dropwise at −78° C. The mixture was heated to 20° C., production of lithium phenoxide was confirmed by checking completion of gas evolution, and the mixture was cooled again to −78° C. A suspension of 4.59 g (10.0 mmol) of (η5-tetramethylcyclopentadienyl)(3-tert-butyl-5-methyl-2-phenoxy)dimethylsilanetitanium dichloride in 20 ml of toluene previously prepared in another schloenk tube was transferred into the above-described reaction solution, then, the mixture was allowed to warm to room temperature gradually. Insoluble components were filtrated, then, the filtrate was concentrated to obtain (η5-tetramethylcyclopentadienyl)(3-tert-butyl-5-methyl-2-phenoxy)dimethylsilanetitanium diphenoxide as a yellow crystal (4.91 g, 85%).

$^1$H NMR (270 MHz, $C_6D_6$) δ 6.68–7.42 (m, 12H), 2.48 (s, 3H), 2.15 (s, 6H), 2.03 (s, 6H), 1.56 (s, 9H), 0.55 (s, 6H)

Example 10

Synthesis of (η5-tetramethylcyclopentadienyl)(3-tert-butyl-5-methyl-2-phenoxy)dimethylsilanetitanium ((+)-1,1'-binaphthyl-2,2'-oxide)

In schloenk tube, 0.859 g (3.0 mmol) of (+)-BINOL was dissolved in 20 ml of THF, and to this solution was added 1.60 M n-butyllithium hexane solution (4.38 ml, 7.0 mmol) dropwise at −78° C. The mixture was heated to 20° C., production of dilithium (+)-1,1'-binaphthyl-2,2'-oxide was confirmed by checking completion of gas evolution, and the mixture was cooled again to −78° C. A suspension of 1.38 g (3.0 mmol) of (η5-tetramethylcyclopentadienyl)(3-tert-butyl-5-methyl-2-phenoxy)dimethylsilanetitanium dichloride in 10 ml of toluene previously prepared in another schloenk tube was transferred into the above-described reaction solution, then, the mixture was allowed to warm to room temperature gradually. Insoluble components were filtrated, then, the filtrate was concentrated to obtain (η5-tetramethylcyclopentadienyl)(3-tert-butyl-5-methyl-2-phenoxy)dimethylsilanetitanium ((+)-1,1'-binaphthyl-2,2'-oxide) as a yellow crystal (1.49 g, 74%).

$^1$H NMR (270 MHz, $C_6D_6$) δ 6.85–7.85 (m, 14H), 2.28 (s, 3H), 2.24 (s, 3H), 2.08 (s, 3H), 1.96 (s, 3H), 1.52 (s, 3H), 0.90 (s, 9H), 0.75 (s, 3H), 0.62 (s, 3H)

Example 11

Synthesis of (η5-tetramethylcyclopentadienyl)(3-tert-butyl-5-methyl-2-phenoxy)dimethylsilanetitanium bisdiethylamide In schloenk tube, 0.300 g (4.1 mmol) of diethylamine was dissolved in 10 ml of ether, and to this solution was added 1.05 M methyllithium ether solution (3.9 ml, 4.1 mmol) dropwise at −78° C. The mixture was heated to 20° C., production of lithiumdiethylamide was confirmed by checking completion of gas evolution, and the mixture was cooled again to −78° C. A suspension of 0.919 g (2.0 mmol) of (η5-tetramethylcyclopentadienyl)(3-tert-butyl-5-methyl-2-phenoxy)dimethylsilanetitanium dichloride in 20 ml of ether previously prepared in another schloenk tube was transferred into the above-described reaction solution, then, the mixture was allowed to warm to room temperature gradually. The reaction solution was concentrated, then, to this was added 20 ml of toluene, and insoluble components were filtrated. The filtrate was concentrated to obtain (η5-tetramethylcyclopentadienyl)(3-tert-butyl-5-methyl-2-phenoxy)dimethylsilanetitanium bis(diethylamide) as a black violet oil (1.03 g, 97%).

$^1$H NMR (270 MHz, $C_6D_6$) δ 7.35 (m, 2H), 3.77 (m, 2H), 3.56 (m, 2H), 2.33 (s, 3H), 2.03 (s, 6H), 2.00 (s, 6H), 1.69 (s, 9H), 0.95 (m, 12H), 0.55 (s, 6H), 9H), 0.58 (s, 3H), 0.55 (s, 3H).

What is claimed is:

1. A method for producing an alkoxytitanium complex represented by the general formula (I),

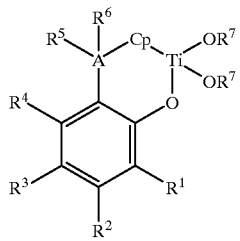

wherein Cp is a group having cyclopentadiene-type anion skeleton,

A represents a carbon atom or silicon atom, $R^1$, $R^2$, $R^3$ and $R^4$ each independently represent:
- a hydrogen atom;
- a halogen atom;
- an alkyl group having 1 to 10 carbon atoms which optionally may be substituted by fluorine,
- an alkoxy group having 1 to 10 carbon atoms which may be substituted by fluorine;
- an aryl group having 6 to 20 carbon atoms which may be substituted by fluorine;
- an aryloxy group having 6 to 20 carbon atoms which may be substituted by fluorine;
- an aralkyl group having 7 to 20 carbon atoms which may be substituted by fluorine;
- an aralkyloxy group having 7 to 20 carbon atoms which may be substituted by fluorine;
- a hydrocarbon-substituted silyl group having 1 to 20 carbon atoms; or
- a hydrocarbon-substituted amino group having 1 to 20 carbon atoms, $R^5$ and $R^6$ each independently represents:
- a hydrogen atom;
- an alkyl group having 1 to 10 carbon atoms which optionally may be substituted by fluorine;
- an alkoxy group having 1 to 10 carbon atoms which may be substituted by fluorine;
- an aryl group having 6 to 20 carbon atoms which may be substituted by fluorine,
- an aryloxy group having 6 to 20 carbon atoms which may be substituted by fluorine,
- an aralkyl group having 7 to 20 carbon atoms which may be substituted by fluorine;
- an aralkyloxy group having 7 to 20 carbon atoms which may be substituted by fluorine;
- a hydrocarbon-substituted silyl group having 1 to 20 carbon atoms; or
- a hydrocarbon-substituted amino group having 1 to 20 carbon atoms; and $R^7$ is the same or different and each independently represent:
- an alkyl group having 1 to 10 carbon atoms which may be substituted; or
- an aralkyl group having 7 to 20 carbon atoms which may be substituted; or
- $R^7$ groups may bond each other to form a ring, which comprises reacting:
- a halogenated titanium complex represented by the general formula (II)

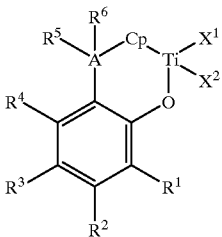

wherein Cp, A, $R^1$, $R^2$, $R^3$, $R^4$, $R^5$ and $R^6$ are the same as defined above, and $X^1$ and $X^2$ each independently represent a halogen atom;

with an alkali metal alkoxide of the formula (III):

$R^7OM$ wherein M and $R^7$ are as defined above.

2. The method according to claim 1, which comprises: reacting a halogenated titanium complex of the formula (II) with an alcohol of the formula (III'):

$R^7OH$ wherein $R^7$ is the same as defined in claim 1.

3. The production method according to claim 2, wherein the reaction is conducted in the co-existence of an amine.

4. A method for producing an aryloxytitanium complex represented by the general formula (IV):

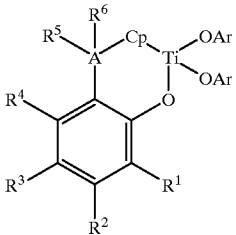

wherein Cp, A, $R^1$, $R^2$, $R^3$, $R^4$, $R^5$ and $R^6$ have respectively the same meanings as defined in claim 1, and Ar is the same or different and each represents an aryl group having 6 to 20 carbon atoms which may be substituted, or Ars may bond mutually to form a ring, which comprises reacting a halogenated titanium complex represented by the general formula (II) as defined in claim 1 with an alkali metal aryloxide represented by the general formula (V):

ArOM         (V)

wherein M represents an alkali metal atom, and Ar is the same as defined above.

5. A method for producing an aminotitanium complex represented by the general formula (VI):

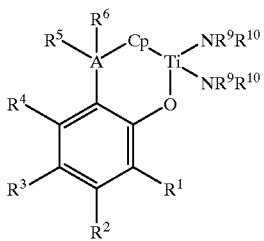

wherein Cp, A, $R^1$, $R^2$, $R^3$, $R^4$, $R^5$ and $R^6$ have respectively the same meanings as defined in claim 1, and $R^9$ and $R^{10}$ each independently represents an alkyl group having 1 to 10 carbon atoms which may be substituted, an aralkyl group having 7 to 20 carbon atoms which may be substituted or a silyl group having 1 to 20 carbon atoms which may be substituted, or $R^9$ and $R^{10}$ may bond each other to form a ring, which comprises reacting a halogenated titanium complex represented by the general formula (II) as defined in claim 1 with an alkali metal amide represented by the general formula (VII):

$R^9R^{10}NM$ wherein, M represents an alkali metal atom, and $R^9$ and $R^{10}$ are the same as defined above.

* * * * *

UNITED STATES PATENT AND TRADEMARK OFFICE
CERTIFICATE OF CORRECTION

PATENT NO. : 6,090,961
DATED : July 18, 2000
INVENTOR(S) : Hidenori Hanaoka et al.

It is certified that error appears in the above-identified patent and that said Letters Patent is hereby corrected as shown below:

Column 68,
Line 21, is changed to read -- wherein M represents an alkali metal, and $R^7$ is as defined above. --

Signed and Sealed this

Tenth Day of August, 2004

JON W. DUDAS
*Acting Director of the United States Patent and Trademark Office*